US010287578B2

(12) United States Patent
Carter et al.

(10) Patent No.: US 10,287,578 B2
(45) Date of Patent: May 14, 2019

(54) DNAZYME-NANOPARTICLE CONJUGATES AND METHODS OF USE THEREOF

(71) Applicant: THE UNIVERSITY OF NOTRE DAME, Notre Dame, IN (US)

(72) Inventors: James Carter, Mishawaka, IN (US); Malcolm J. Fraser, Jr., Granger, IN (US)

(73) Assignee: The University of Notre Dame, Notre Dame, IN (US)

( * ) Notice: Subject to any disclaimer, the term of this patent is extended or adjusted under 35 U.S.C. 154(b) by 0 days.

(21) Appl. No.: 14/757,293

(22) PCT Filed: Jun. 16, 2014

(86) PCT No.: PCT/US2014/042480
§ 371 (c)(1),
(2) Date: Dec. 14, 2015

(87) PCT Pub. No.: WO2014/201454
PCT Pub. Date: Dec. 18, 2014

(65) Prior Publication Data
US 2017/0166890 A1 Jun. 15, 2017
US 2017/0298346 A9 Oct. 19, 2017

Related U.S. Application Data

(60) Provisional application No. 61/835,758, filed on Jun. 17, 2013, provisional application No. 61/835,173, filed on Jun. 14, 2013.

(51) Int. Cl.
| C12N 15/11 | (2006.01) |
| G01N 33/569 | (2006.01) |
| C12N 15/113 | (2010.01) |
| G01N 33/53 | (2006.01) |
| G01N 33/58 | (2006.01) |
| C12Q 1/6816 | (2018.01) |
| C12Q 1/70 | (2006.01) |

(52) U.S. Cl.
CPC .......... *C12N 15/11* (2013.01); *C12N 15/1131* (2013.01); *C12Q 1/6816* (2013.01); *C12Q 1/701* (2013.01); *G01N 33/5308* (2013.01); *G01N 33/56983* (2013.01); *G01N 33/588* (2013.01); *C12N 2310/127* (2013.01); *C12N 2310/351* (2013.01); *C12N 2310/3517* (2013.01); *C12N 2320/10* (2013.01); *C12N 2770/24122* (2013.01); *G01N 2333/181* (2013.01); *G01N 2333/185* (2013.01); *Y02A 50/51* (2018.01); *Y02A 50/53* (2018.01); *Y02A 50/60* (2018.01)

(58) Field of Classification Search
None
See application file for complete search history.

(56) References Cited

U.S. PATENT DOCUMENTS

2010/0129437 A1 5/2010 Gaillard
2011/0229966 A1 9/2011 Han et al.

OTHER PUBLICATIONS

DeLong, et al. (2010) "Functionalized gold nanoparticles for the binding, stabilization, and delivery of therapeutic DNA, RNA, and other biological molecules", Neurotechnology Science and Applications, 3: 53-63.*
Stein, et al. (2011) "Inhibition of Dengue Virus Infections in Cell Cultures and in AG129 Mice by a Small Interfering RNA Targeting a Highly Conserved Sequence", Journal of Virology, 85(19): 10154-66.*
Dash, et al. (2008) "RNA interference mediated inhibition of Chikungunya virus replication in mammalian cells", Biochemical and Biophysical Research Communications, 376(4): 718-22.*
Carter, et al. (2013) "A novel dengue virus detection method that couples DNAzyme and gold nanoparticle approaches", Virology Journal, 10: 201 (E-Publication) (15 pages).*
Debouttiere, et al. (2006) "Design of Gold Nanoparticles for Magnetic Resonance Imaging", Advanced Functional Materials, 16: 2330-39.*
Seyhan, et al. (2007) "RNA Interference-Mediated Inhibition of Semiliki Forest Virus Replication in Mammalian Cells", Oligonucleotides, 17: 473-84.*
Ryoo et al. Functional delivery of DNAzyme with iron oxide nanoparticles for hepatitis C virus gene knockdown by Ryoo et al. Biomaterials Marct:i 2012 vol. 33 No. 9_pp. 2754-2761.
Xiang et al. Expanding DNAzyme Functionality through Enzyme Cascades with Applications in Single Nucleotide Repair and Tunable DNA-Directed Assembly of Nanomaterials. Jan. 1, 2013 vol. 4 No. 1 pp. 398-404.

(Continued)

*Primary Examiner* — Robert M Kelly

(74) *Attorney, Agent, or Firm* — The Intellectual Property Law Office of Verne A. Luckow, LLC

(57) ABSTRACT

The present invention relates to DNAzymes (also known as deoxyribozymes, DNA enzymes, catalytic DNA, or DZ), which are conjugated to nanoparticles (NP) to facilitate the detection of nucleic acids. One aspect of the invention relates to compounds comprising DNAzymes conjugated to nanoparticles (DZ-NP), such as metallic or gold nanoparticles, and methods for their synthesis. Another aspect of the invention relates to methods of using the conjugated compounds to detect nucleic acids, such as genomic material or transcripts of infectious agents, such as viruses, exemplified by applications demonstrating visual detection of Flavivirus RNA molecules, such as dengue virus, or Alphavirus RNA molecules, such as chikungunya virus, in short time periods, using compositions comprising stable components.

22 Claims, 20 Drawing Sheets

Specification includes a Sequence Listing.

(56) References Cited

OTHER PUBLICATIONS

Alvarez et al. Long-range RNA-RNA interactions circularize the dengue virus genome. J Virol Jun. 2005 vol. 79 No. 11 pp. 6631-6643.
Lee et al. Suppression of hepatitis C virus genome replication in cells with RNA-cleaving DNA enzymes and short-hairpin RNA. Oligoriucleotides. Dec. 2010 vol. 20 No. 6 pp. 285-296.
IDS_REF_ISR_90 Harris E, Roberts TG, Smith, L, Selle J, Kramer LD, Valle, S, Sandoval E, Balmaseda E Typing of Dengue Viruses in Clinical Specimens and Mosquitos by Single-Tube Miltiplex Reverse Transcriptase PCR. J. Clinical Microbiol vol. 36, No. 9, Sep. 1998, p. 2634-2639.
IDS_REF_ISR_91 International Search Report and Written Opinion for PCT/US14/42480, dated Jan. 16, 2015.
Aaskov J, Buzacott K, Thu HM, Lowry K, Holmes EC: Long-term transmission of defective RNA viruses in humans and Aedes mosquitoes. Science 2006, 311:236-238.
Adalja AA, Sell TK, Bouri N, Franco C: Lessons learned during dengue outbreaks in the United States, 2001-2011. Emerg Infect Dis 2012, 18:608-614.
Alvarez DE, Lodeiro MF, Luduena SJ, Pietrasanta LI, Gamarnik AV: Long-range RNA-RNA interactions circularize the dengue virus genome. J Virol 2005, 79:6631-6643.
Anez G, Heisey DA, Espina LM, Stramer SL, Rios M: Phylogenetic analysis of dengue virus types 1 and 4 circulating in Puerto Rico and Key west, Florida, during 2010 epidemics. AmJTrop Med Hyg 2012, 87:548-553.
Apte-Deshpande A, Paingankar M, Gokhale MD, Deobagkar DN: Serratia odorifera a midgut inhabitant of Aedes aegypti mosquito enhances its susceptibility to dengue-2 virus. PLoS One 2012, 7:e40401.
Auslander S, Ketzer P, Hartig JS: A ligand-dependent hammerhead ribozyme switch for controlling mammalian gene expression. Mol Biosyst 2010, 6:807-814.
Bai X, Shao C, Han X, Li Y, Guan Y, Deng Z: Visual detection of sub-femtomole DNA by a gold nanoparticle seeded homogeneous reduction assay: toward a generalized sensitivity-enhancing strategy. Biosens Bioelectron 2010, 25:1984-1988.
Baum DA, Silverman SK: Deoxyribozymes: useful DNA catalysts in vitro and in vivo. Cell Mol Life Sci 2008, 65:2156-2174.
Becker R, Helenius A, Simons K: Solubilization of the Semliki forest virus membrane with sodium dodecyl sulfate. Biochemistry 1975, 14:1835-1841.
Cairns MJ, King A, Sun LQ: Optimisation of the 10-23 DNAzyme-substrate pairing interactions enhanced RNA cleavage activity at purine-cytosine target sites. Nucleic Acids Res 2003, 31:2883-2889.
Cao X, Ye Y, Liu S: Gold nanoparticle-based signal amplification for biosensing. Anal Biochem 2010, 417:1-16.
Caron M, Paupy C, Grard G, Becquart P, Mombo I, Nso BB, Kassa Kassa F, Nkoghe D, Leroy EM: Recent introduction and rapid dissemination of chikungunya virus and dengue virus serotype 2 associated with human and mosquito coinfections in Gabon, central Africa. Clin Infect Dis 2012, 55:e45-e53.
Carter JR, Keith JH, Barde PV, Fraser TA, Fraser MJ JR: Targeting of highly conserved dengue virus sequences with anti-dengue virus trans-splicing group I introns. BMC Mol Biol 2010, 11:84.
Carter, J.R., Balaraman, V., Kucharski, C.A., Fraser, T.S., and Fraser, M.J., Jr. A novel dengue virus detection method that couples DNAzyme and gold nanoparticle approaches. Virol J 10, 201.
Chisenhall DM, Vitek CJ, Richards SL, Mores CN: A method to increase efficiency in testing pooled field-collected mosquitoes. J Am Mosq Control Assoc 2008, 24:311-314.
Cho S, Kim JE, Lee BR, Kim JH, Kim BG: Bis-aptazyme sensors for hepatitis C virus replicase and helicase without blank signal. Nucleic Acids Res 2005, 33:e177.
Cieslak M, Szymanski J, Adamiak RW, Cierniewski CS: Structural rearrangements of the 10-23 DNAzyme to beta 3 integrin subunit mRNA induced by cations and their relations to the catalytic activity. J Biol Chem 2003, 278:47987-47996.
Clyde K, Kyle JL, Harris E: Recent advances in deciphering viral and host determinants of dengue virus replication and pathogenesis. J Virol 2006, 80:11418-11431.
Cordel, H., Quatresous, I., Paquet, C., and Couturier, E. (2006). Imported cases of chikungunya in metropolitan France, Apr. 2005-Feb. 2006. Euro Surveill 11, E060420 060423.
De Oliveira PC, Pavoni DP, Queiroz MH, De Borba L, Goldenberg S, Dos Santos CN, Krieger MA: Dengue virus infections: comparison of methods for diagnosing the acute disease. J Clin Virol 2005, 32:272-277.
De Silva C, Walter NG: Leakage and slow allostery limit performance of single drug-sensing aptazyme molecules based on the hammerhead ribozyme. RNA 2009, 15:76-84.
Effler PV, Pang L, Kitsutani P, Vorndam V, Nakata M, Ayers T, Elm J, Tom T, Reiter P, Rigau-Perez JG, et al: Dengue fever, Hawaii, 2001-2002. Emerg Infect Dis 2005, 11:742-749.
Englebienne P: Use of colloidal gold surface plasmon resonance peak shift to infer affinity constants from the interactions between protein antigens and antibodies specific for single or multiple epitopes. Analyst 1998, 123:1599-1603.
Ferapontova EE, Gothelf KV: Effect of serum on an RNA aptamer-based electrochemical sensor for theophylline. Langmuir 2009, 25:4279-4283.
Figueiredo LT: Dengue in Brazil. Rev Soc Bras Med Trop 2012, 45:285.
Fronhoffs, S., Totzke, G., Stier, S., Wernert, N., Rothe, M., Bruning, T., Koch, B., Sachinidis, A., Vetter, H., and Ko, Y. (2002). A method for the rapid construction of cRNA standard curves in quantitative real-time reverse transcription polymerase chain reaction. Molecular and cellular probes 16, 99-110.
Geyer CR, Sen D: Evidence for the metal-cofactor independence of an RNA phosphodiester-cleaving DNA enzyme. Chem Biol 1997, 4:579-593.
Geyer CR, Sen D: Lanthanide probes for a phosphodiester-cleaving, lead-dependent, DNAzyme. J Mol Biol 1998, 275:483-489.
Goho, A: Gold quantum dots. Science News Sep. 11, 2004, 166(11): 174. (Preview Only).
Gubler DJ: Dengue and dengue hemorrhagic fever. Clin Microbial Rev 1998, 11:480-496.
Hall B, Hesselberth JR, Ellington AD: Computational selection of nucleic acid biosensors via a slip structure model. Biosens Bioelectron 2007, 22:1939-1947.
Higgs, S., and Ziegler, S.A. A nonhuman primate model of chikungunya disease. J Clin Invest (2010) 120, 657-660.
Jansen, C.C., Prow, N.A., Webb, C.E., Hall, R.A., Pyke, A.T., Harrower, B.J., Pritchard, I.L., Zborowski, P., Ritchie, S.A., Russell, R.C., et al. (2009). Arboviruses isolated from mosquitoes collected from urban and peri-urban areas of eastern Australia. J Am Mosq Control Assoc 25, 272-278.
Jeanmougin, F., Thompson, J.D., Gouy, M., Higgins, D.G., and Gibson, T.J. (1998). Multiple sequence alignment with Clustal X. Trends Biochem Sci 23, 403-405.
Li J, Lu Y: A Highly Sensitive and Selective Catalytic DNA Biosensor for Lead Ions. J Am Chem Soc 2006, 122:10466-10467.
Kabra SK, Jain Y, Singhal T, Ratageri VH: Dengue hemorrhagic fever: clinical manifestations and management. Indian J Pediatr 1999, 66:93-101.
Knudsen SM, Lee J, Ellington AD, Savran CA: Ribozyme-mediated signal augmentation on a mass-sensitive biosensor. J Am Chem Soc 2006, 128:15936-15937.
Kuwayama M, Ito M, Takao S, Shimazu Y, Fukuda S, Miyazaki K, Kurane I, Takasaki T: Japanese encephalitis virus in meningitis patients, Japan. Emerg Infect Dis 2005, 11:471-473.
Lanciotti RS, Calisher CH, Gubler DJ, Chang GJ, Vorndam AV: Rapid detection and typing of dengue viruses from clinical samples by using reverse transcriptase-polymerase chain reaction. J Clin Microbiol 1992, 30:545-551.
Li D, Lott WB, Lowry K, Jones A, Thu HM, Aaskov J: Defective interfering viral particles in acute dengue infections. PLoS One 2011, 6:e19447.
Liu J, Lu Y: Preparation of aptamer-linked gold nanoparticle purple aggregates for colorimetric sensing of analytes. Nat Protoc 2006, 1:246-252.

(56) References Cited

OTHER PUBLICATIONS

Liu Y, Wu Z, Zhou G, He Z, Zhou X, Shen A, Hu J: Simple, rapid, homogeneous oligonucleotides calorimetric detection based on non-aggregated gold nanoparticles. Chem Commun (Camb) 2012, 48:3164-3166.

Macnamara FN: Zika virus: a report on three cases of human infection during an epidemic of jaundice in Nigeria. Trans R Soc Trop Med Hyg 1954, 48:139-145.

Marchette NJ, Garcia R, Rudnick A: Isolation of Zika virus from Aedes aegypti mosquitoes in Malaysia. AmJTrop Med Hyg 1969, 18:411-415.

Marriott, A.C., and Dimmock, N.J. Defective interfering viruses and their potential as antiviral agents. Rev Med Virol 20, 51-62.

Nawtaisong P, Keith J, Fraser T, Balaraman V, Kolokoltsov A, Davey RA, Higgs S, Mohammed A, Rongsriyam Y, Komalamisra N, Fraser MJ JR: Effective suppression of dengue fever virus in mosquito cell cultures using retroviral transduction of hammerhead ribozymes targeting the viral genome. Virol J 2009, 6:73.

Nougairede, A., De Fabritus, L., Aubry, F., Gould, E.A., Holmes, E.G., and De Lamballerie, X. (2013). Random codon re-encoding induces stable reduction of replicative fitness of Chikungunya virus in primate and mosquito cells. PLoS Pathog 9, e1003172.

Ogawa A, Maeda M: Easy design of logic gates based on aptazymes and noncrosslinking gold nanoparticle aggregation. Chem Commun (Camb) 2009, 21:4666-4668.

Ogawa A, Maeda M: Simple and rapid colorimetric detection of cofactors of aptazymes using noncrosslinking gold nanoparticle aggregation. Bioorg Med Chem Lett 2008, 18:6517-6520.

Ogawa A: RNA aptazyme-tethered large gold nanoparticles for on-the-spot sensing of the aptazyme ligand. Bioorg Med Chem Lett 2011, 21:155-159.

Parida, M.M., Santhosh, S.R., Dash, P.K., Tripathi, N.K., Lakshmi, V., Mamidi, N., Shrivastva, A., Gupta, N., Saxena, P., Babu, J.P., et al. (2007). Rapid and real-time detection of Chikungunya virus by reverse transcription loop-mediated isothermal amplification assay. J Clin Microbiol 45, 351-357.

Peeling RW, Artsob H, Pelegrino JL, Buchy P, Cardosa MJ, Devi S, Enria DA, Farrar J, Gubler DJ, Guzman MG, et al: Evaluation of diagnostic tests: dengue. Nat Rev Microbiol 2010, 8:S30-S38.

Plante K, Wang E, Partidos CD, Weger J, Gorchakov R, Tsetsarkin K, Borland EM, Powers AM, Seymour R, Stinchcomb DT, et al: Novel chikungunya vaccine candidate with an IRES-based attenuation and host range alteration mechanism. PLoS Pathog 2011, 7:e1002142.

Qi RF, Zhang L, Chi CW: Biological characteristics of dengue virus and potential targets for drug design. Acta Biochim Biophys Sin (Shanghai) 2008, 40:91-101.

Rai MA: Epidemic: Control of dengue fever in Pakistan. Nature 2011, 479:41.

Ramos MM, Mohammed H, Zielinski-Gutierrez E, Hayden MH, Lopez JL, Fournier M, Trujillo AR, Burton R, Brunkard JM, Anaya-Lopez L, et al: Epidemic dengue and dengue hemorrhagic fever at the Texas-Mexico border: results of a household-based seroepidemiologic survey, Dec. 2005. AmJTrop Med Hyg 2008, 78:364-369.

Randolph SE, Rogers DJ: The arrival, establishment and spread of exotic diseases: patterns and predictions. Nat Rev Microbiol 2010, 8:361-371.

Reed W, Carroll J, Agramonte A, Lazear JW: The etiology of yellow fever—a preliminary note. Publ Health Pap Rep 1900, 26:37-53.

Reiskind, M.H., Westbrook, C.J., and Lounibos, L.P. Exposure to chikungunya virus and adult longevity in Aedes aegypti (L.) and Aedes albopictus (Skuse). (2010)J Vector Ecol 35, 61-68.

Rigau-Perez JG, Clark GG, Gubler DJ, Reiter P, Sanders EJ, Vorndam AV: Dengue and dengue haemorrhagic fever. Lancet 1998, 352:971-977.

Roberts L: Mosquitoes and disease. Science 2002, 298:82-83.

Rodenhuis-Zybert, I.A., Van Der Schaar, H.M., Da Silva Voorham, J.M., Van Der Ende-Metselaar, H., Lei, H.Y., Wilschut, J., and Smit, J.M. Immature dengue virus: a veiled pathogen? PLoS Pathog 6, e1000718.

Rueda D, Walter NG: Fluorescent energy transfer readout of an aptazyme-based biosensor. Meth Mol Biol 2006, 335:289-310.

Santoro SW, Joyce GF: A general purpose RNA-cleaving DNA enzyme. Proc Natl Acad Sci U S A 1997, 94:4262-4266.

Santoro SW, Joyce GF: Mechanism and utility of an RNA-cleaving DNA enzyme. Biochemistry 1998, 37:13330-13342.

Sato K, Hosokawa K, Maeda M: Non-cross-linking gold nanoparticle aggregation as a detection method for single-base substitutions. Nucleic Acids Res 2005, 33:e4.

Shu PY, Huang JH: Current advances in dengue diagnosis. Clin Diagn Lab Immunol 2004, 11:642-650.

Song KM, Cho M, Jo H, Min K, Jeon SH, Kim T, Han MS, Ku JK, Ban C: Gold nanoparticle-based colorimetric detection of kanamycin using a DNA aptamer. Anal Biochem 2011, 415:175-181.

Sun, LQ, Cairns, MJ, Gerlach, WL., Witherington, C, Wang, L, King, A: Suppression of smooth muscle cell proliferation by a c-myc RNA-cleaving deoxyribozyme. J Biol Chem 1999, 274:17236-17241.

Thiboutot, M.M., Kannan, S., Kawalekar, O.U., Shedlock, D.J., Khan, A.S., Sarangan, G., Srikanth, P., Weiner, D.B., and Muthumani, K. Chikungunya: a potentially emerging epidemic? PLoS Negl Trop Dis 4, e623.

Thompson KM, Syrett HA, Knudsen SM, Ellington AD: Group I aptazymes as genetic regulatory switches. BMC Biotechnol 2002, 2:21.

Tricou V, Vu HT, Quynh NV, Nguyen CV, Tran HT, Farrar J, Wills B, Simmons CP: Comparison of two dengue NS1 rapid tests for sensitivity, specificity and relationship to viraemia and antibody responses. BMC Infect Dis 2010, 10:142.

Tsetsarkin, K., Higgs, S., McGee, C.E., De Lamballerie, X., Charrel, R.N., and Vanlandingham, D.L. (2006). Infectious clones of Chikungunya virus (La Reunion isolate) for vector competence studies. Vector Borne Zoonotic Dis 6, 325-337.

Tsetsarkin, K.A., McGee, C.E., Volk, S.M., Vanlandingham, D.L., Weaver, S.C., and Higgs, S. (2009). Epistatic roles of E2 glycoprotein mutations in adaption of chikungunya virus to Aedes albopictus and Ae. aegypti mosquitoes. PLoS One 4, e6835.

Van Bortel, W., Dorleans, F., Rosine, J., Blateau, A., Rousset, D., Matheus, S., Leparc-Goffart, I., Flusin, O., Prat, C., Cesaire, R., et al. (2014). Chikungunya outbreak in the Caribbean region, Dec. 2013 to Mar. 2014, and the significance for Europe. Euro Surveill 19.

Van Den Hurk, A.F., Hall-Mendelin, S., Pyke, A.T., Smith, G.A., and Mackenzie, J.S. Vector competence of Australian mosquitoes for chikungunya virus. Vector Borne Zoonotic Dis 10, 489-495.

Van Der Schaar, H.M., Rust, M.J., Chen, C., Van Der Ende-Metselaar, H., Wilschut, J., Zhuang, X., and Smit, J.M. (2008). Dissecting the cell entry pathway of dengue virus by single-particle tracking in living cells. PLoS Pathog 4, e1000244.

Van Der Schaar, H.M., Rust, M.J., Waarts, B.L., Van Der Ende-Metselaar, H., Kuhn, R.J., Nilschut, J., Zhuang, X., and Smit, J.M. (2007). Characterization of the early events in dengue virus cell entry by biochemical assays and single-virus tracking. J Virol 81, 12019-12028.

Vaughn DW, Green S, Kalayanarooj S, Innis BL, Nimmannitya S, Suntayakorn S, Endy TP, Raengsakulrach B, Rothman AL, Ennis FA, Nisalak A: Dengue viremia titer, antibody response pattern, and virus serotype correlate with disease severity. J Infect Dis 2000, 181:2-9.

Wang, W.K., Lin, S.R., Lee, C.M., King, C.C., and Chang, S.C. (2002). Dengue type 3 virus in plasma is a population of closely related genomes: quasispecies. J Virol 76, 4662-4665.

Weill L, Louis D, Sargueil B: Selection and evolution of NTP-specific aptamers. Nucleic Acids Res 2004, 32:5045-5058.

Westbrook, C.J., Reiskind, M.H., Pesko, K.N., Greene, K.E., and Lounibos, L.P. Larval environmental temperature and the susceptibility of Aedes albopictus Skuse (Diptera: Culicidae) to Chikungunya virus. Vector Borne Zoonotic Dis 10, 241-247.

(56) References Cited

OTHER PUBLICATIONS

Who: Dengue and dengue haemorrhagic fever, Fact sheet N°117. Geneva, Switzerland: WHO: Dengue and dengue haemorrhagic fever; 2012.

Wieland M, Berschneider B, Erlacher MD, Hartig JS: Aptazyme-mediated regulation of 16S ribosomal RNA. Chem Biol 2010, 17:236-242.

Williams DH, Fleming I: Spectroscopic Methods in Organic Chemistry. 5th edition. Blacklick, Ohio, U.S.A: McGraw-Hill; 1995. (Table of Contents and Text Are Unavailable in Electronic Form) This book concentrates on the practical aspects of using spectroscopic techniques to solve structural problems. It is written at a level for an advanced undergraduate or graduate course in applied spectroscopy. It describes the uses of the four spectroscopic methods: UV, IR, NMR and Mass Spectra in organic chemistry.

* cited by examiner

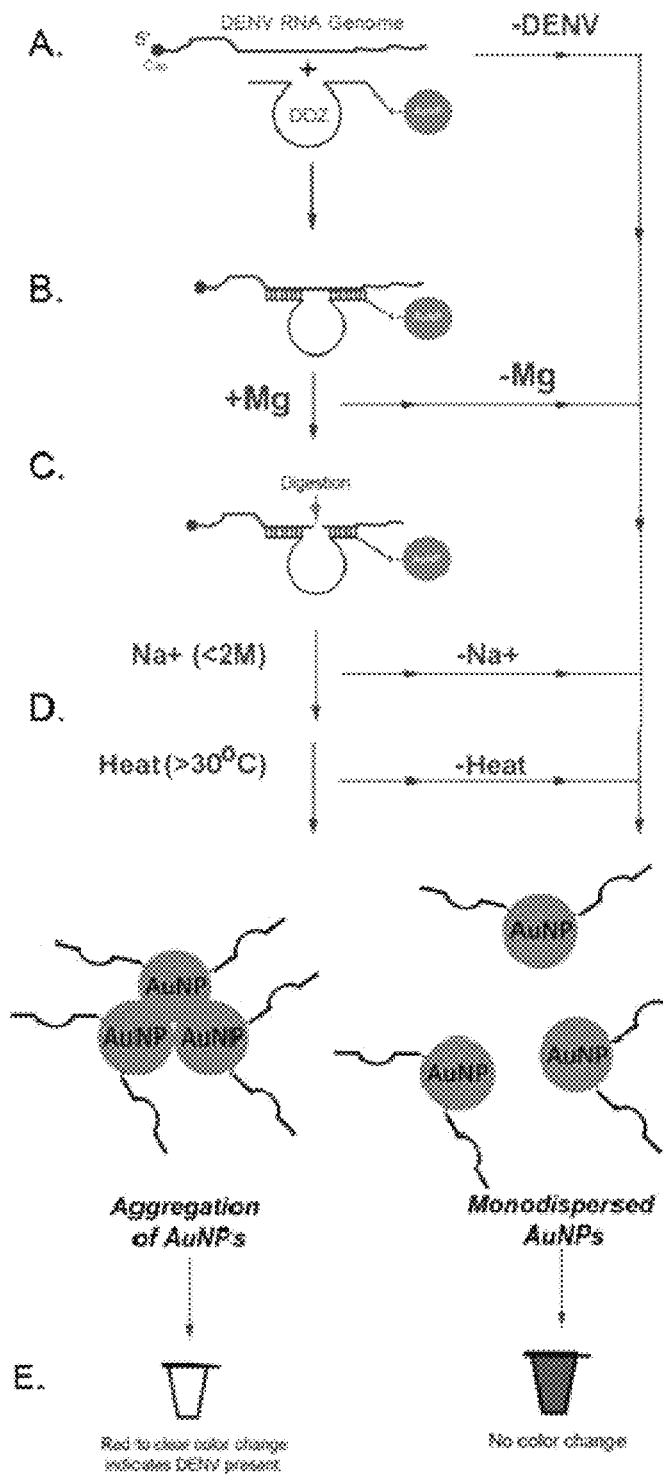
Fig. 1 (Panels 1A-1E)

Basic Design of the 10-23 Anti-DENV (DDZ) and Anti-CHIKV (CDZ) DNAzymes and
Schematic Diagram of the DENV and CHIKV Genomes
2A.
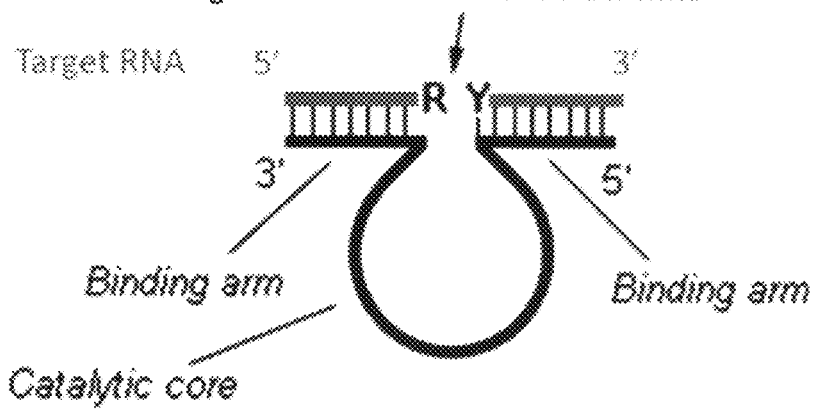
2B.
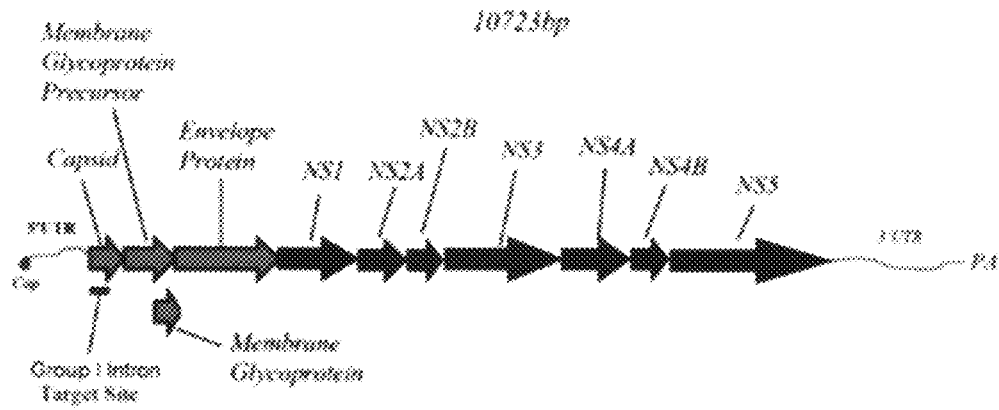
2C.
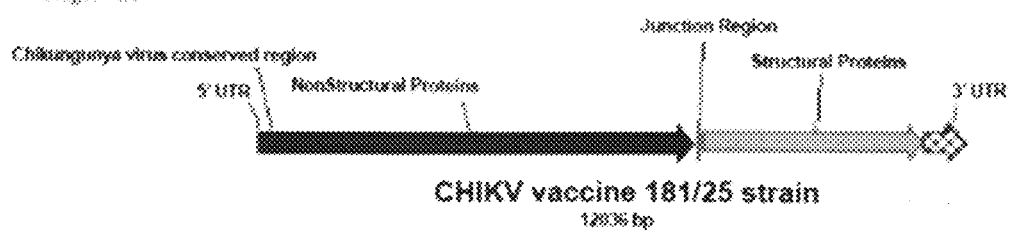
Fig. 2 (Panels 2A-2C)

Determination of Optimal NaCl and SDS Concentrations
A.
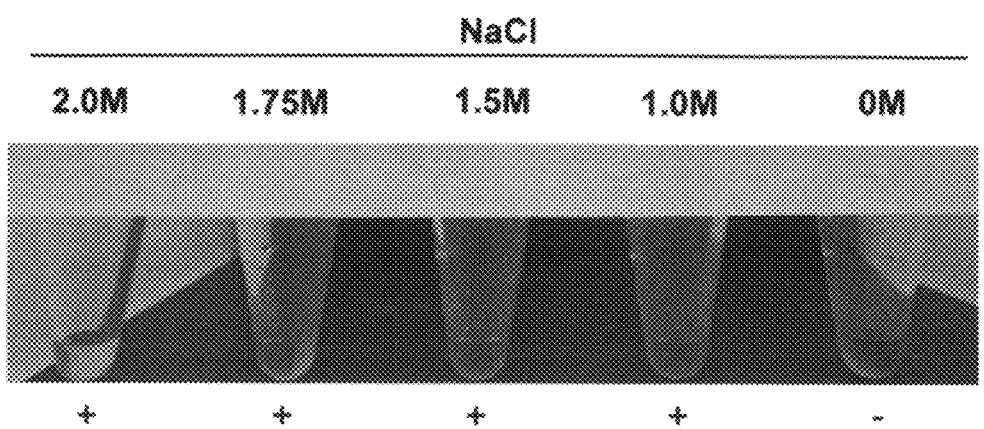
B.
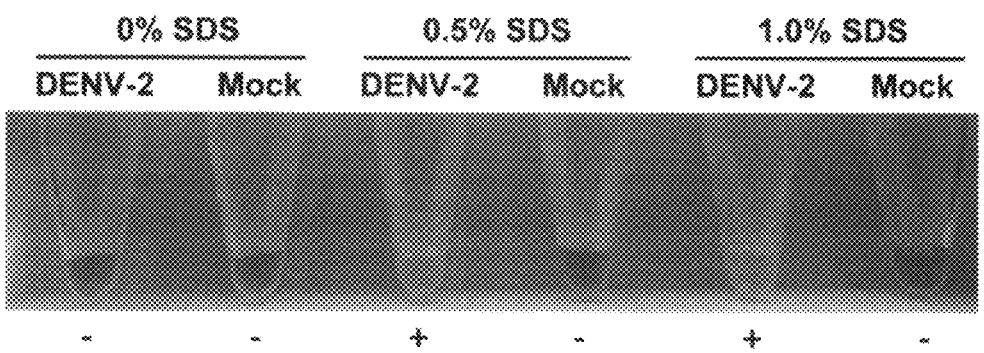
Fig. 5 (Panels 5A-5B)

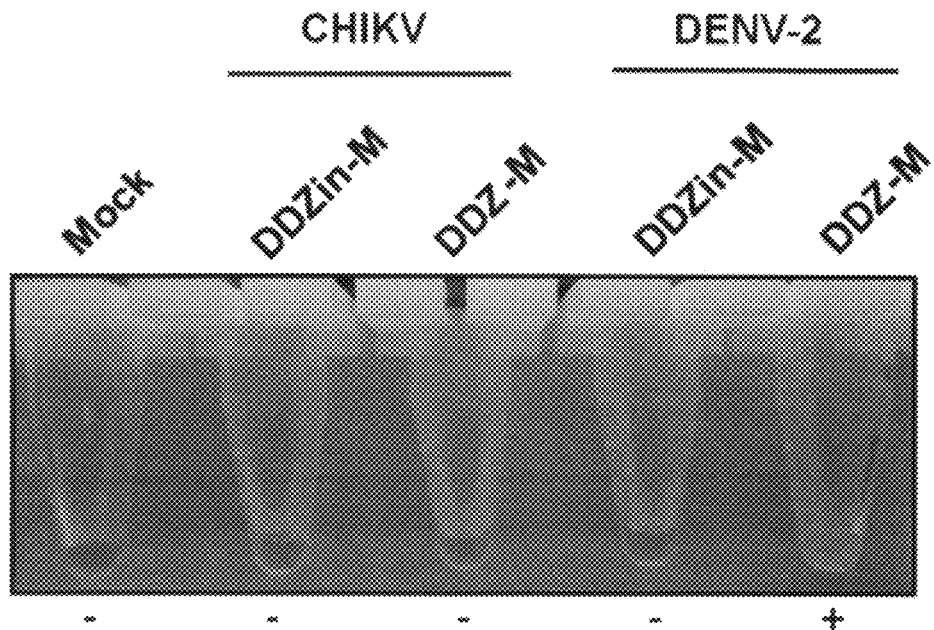
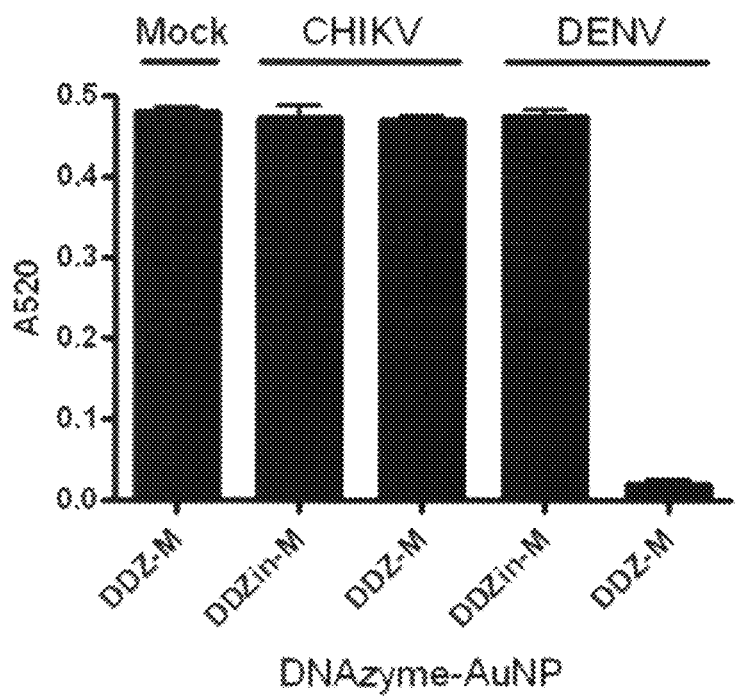
Fig. 7 (Panels 7A-7B)

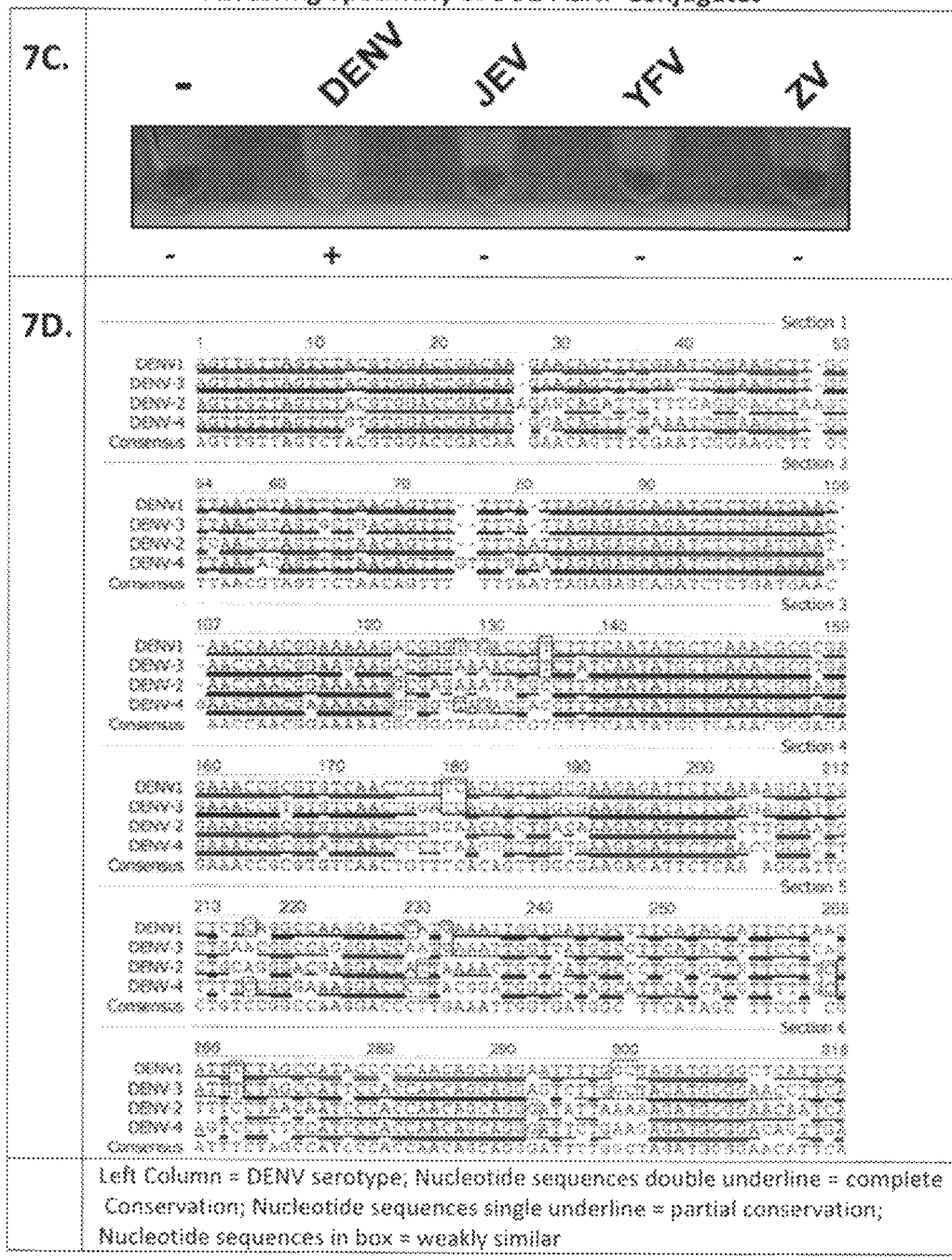
Fig. 7 (Panels 7C-7D)

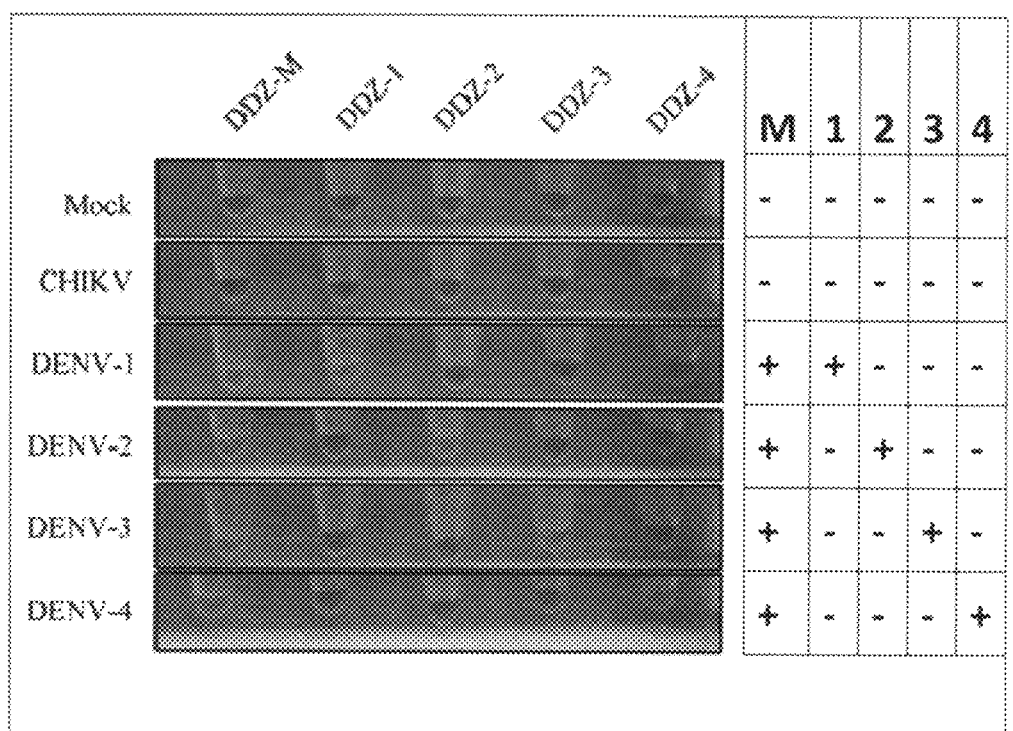
Fig. 7 (Panel 7E)

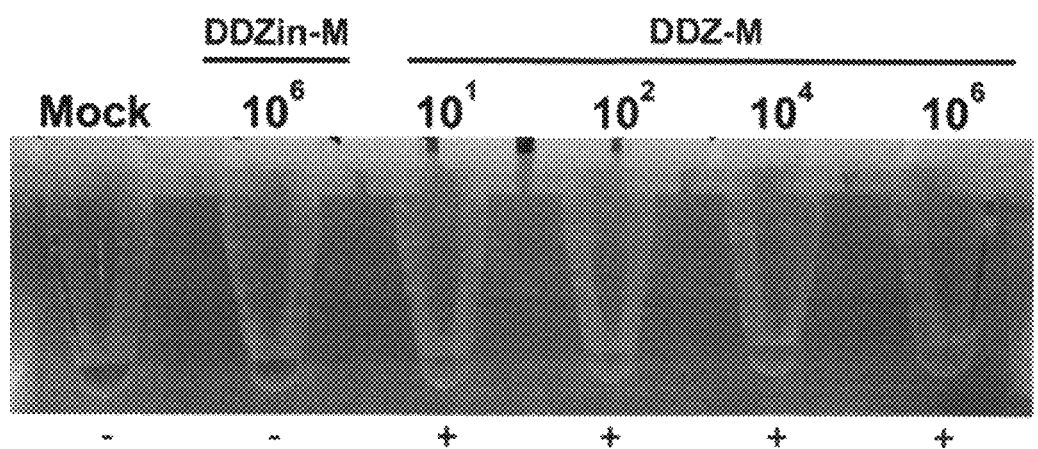
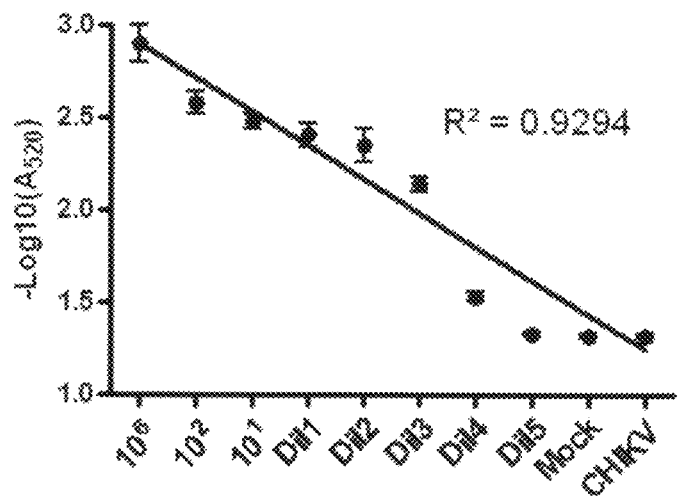
Fig. 8 (Panels 8A-8B)

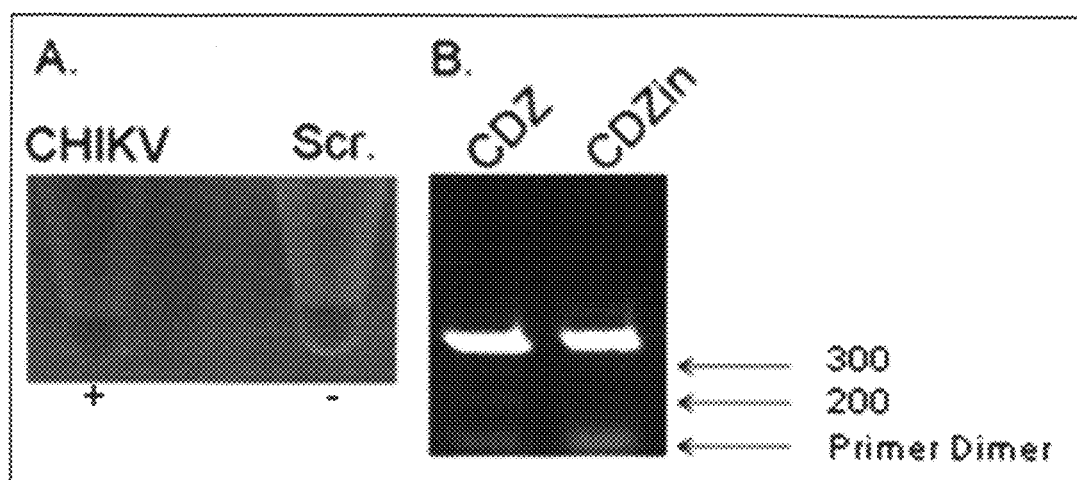
Fig. 9 (Panels 9A-9B)

Figure 9:
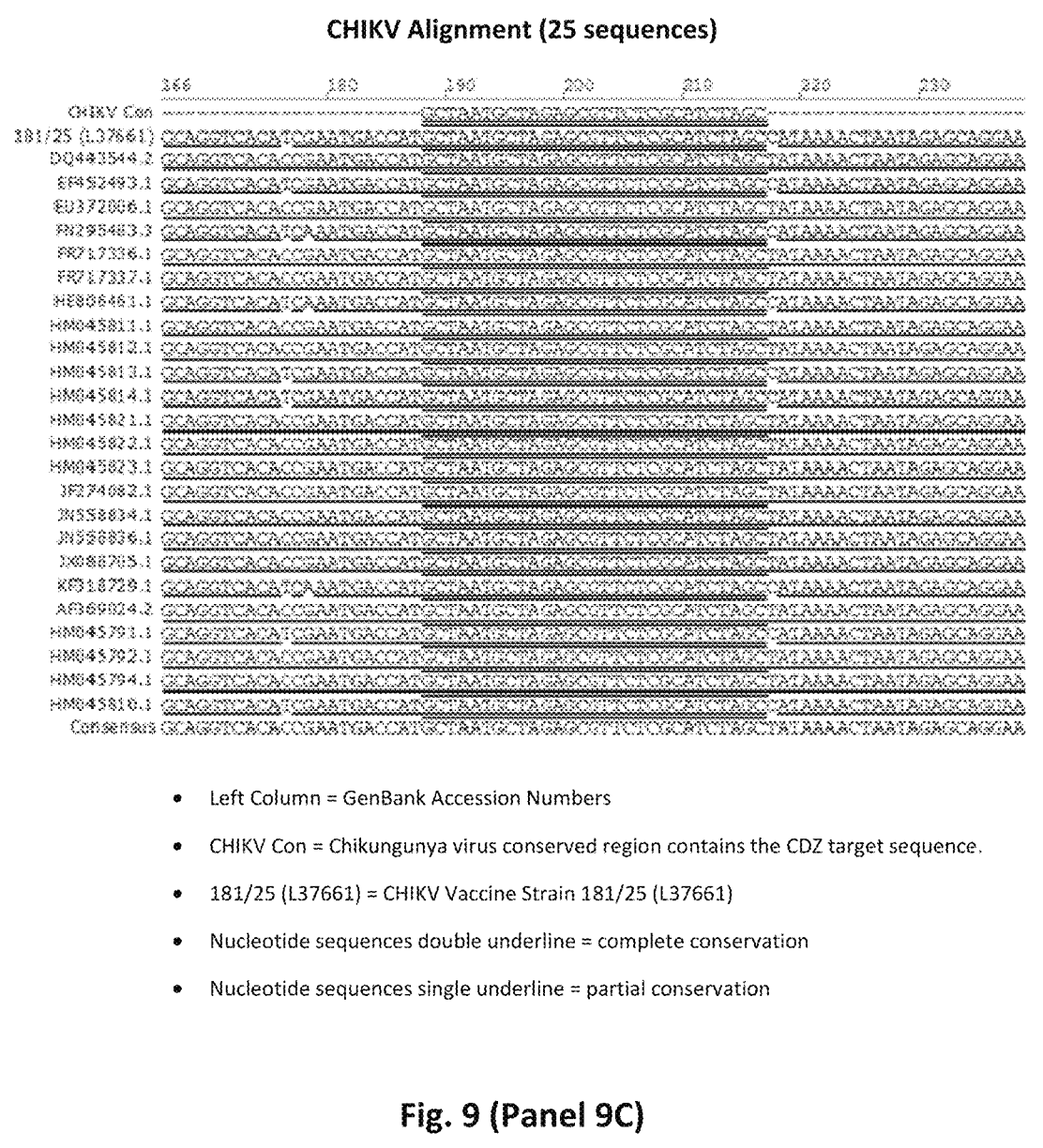

CHIKV Alignment (25 sequences)

- Left Column = GenBank Accession Numbers
- CHIKV Con = Chikungunya virus conserved region contains the CDZ target sequence.
- 181/25 (L37661) = CHIKV Vaccine Strain 181/25 (L37661)
- Nucleotide sequences double underline = complete conservation
- Nucleotide sequences single underline = partial conservation

Fig. 9 (Panel 9C)

Determination of optimal SDS concentrations for CHIKV detection.

| 0% SDS | | 0.5% SDS | | 1.0% SDS | |
|---|---|---|---|---|---|
| CHIKV | Mock | CHIKV | Mock | CHIKV | Mock |
| − | − | + | − | + | − |

Fig. 11

Assessment of CDZ-AuNP Specificity For CHIKV RNA

| Mock | CHIKV | | Sind | DENV |
|------|-------|-------|------|------|
|      | CDZ   | CDZin |      |      |
| −    | +     | −     | −    | −    |

Fig. 13

Analysis of CDZ-AuNP Limits of CHIKV Detection

14A

| Mock | CDZin $10^6$ | CDZ $10^5$ | $10^4$ | $10^2$ | $10^1$ |
|---|---|---|---|---|---|
| − | − | + | + | + | + |

Confirmation of CHIKV Titers of Samples Used for
Analysis of CDZ-AuNP Limits of CHIKV Detection

14B

Fig. 14 (Panels 14A and 14B)

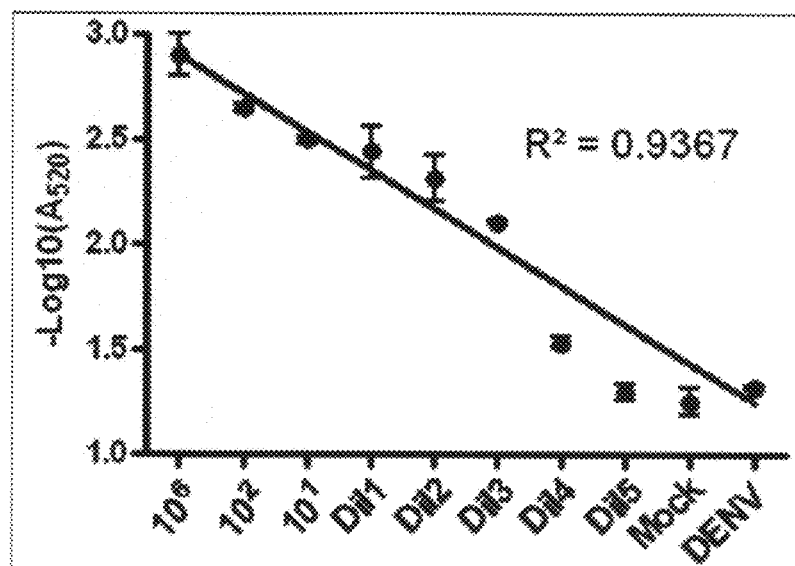
Fig. 15 (Panel 15A)

Confirmation of CHIKV Titers of Samples Used for Analysis of CDZ-AuNP sensitivity by UV/Vis spectrophotometry

15B

Fig. 15 (Panel 15B)

SEQUENCE LISTING

```
<160> NUMBER OF SEQ ID NOS: 32

<210> SEQ ID NO 1
<211> LENGTH: 9
<212> TYPE: DNA
<213> ORGANISM: Artificial Sequence
<220> FEATURE:
<223> OTHER INFORMATION: Synthetic sequence

<400> SEQUENCE: 1 tttctctcg                                                               9

<210> SEQ ID NO 2
<211> LENGTH: 9
<212> TYPE: DNA
<213> ORGANISM: Artificial Sequence
<220> FEATURE:
<223> OTHER INFORMATION: Synthetic

<400> SEQUENCE: 2 atcgctcca                                                               9
```

```
<210> SEQ ID NO 3
<211> LENGTH: 9
<212> TYPE: DNA
<213> ORGANISM: Artificial Sequence
<220> FEATURE:
<223> OTHER INFORMATION: Synthetic

<400> SEQUENCE: 3 aaaggcgta                                                                 9

<210> SEQ ID NO 4
<211> LENGTH: 9
<212> TYPE: DNA
<213> ORGANISM: Artificial Sequence
<220> FEATURE:
<223> OTHER INFORMATION: Synthetic

<400> SEQUENCE: 4 tagccaaga                                                                 9

<210> SEQ ID NO 5
<211> LENGTH: 9
<212> TYPE: DNA
<213> ORGANISM: Artificial Sequence
<220> FEATURE:
<223> OTHER INFORMATION: Synthetic

<400> SEQUENCE: 5 gttggttca                                                                 9

<210> SEQ ID NO 6
<211> LENGTH: 9
<212> TYPE: DNA
<213> ORGANISM: Artificial Sequence
<220> FEATURE:
<223> OTHER INFORMATION: Synthetic

<400> SEQUENCE: 6 tttctctcg                                                                 9

<210> SEQ ID NO 7
<211> LENGTH: 9
<212> TYPE: DNA
<213> ORGANISM: Artificial Sequence
<220> FEATURE:
<223> OTHER INFORMATION: Synthetic

<400> SEQUENCE: 7 gtttcagca                                                                 9

<210> SEQ ID NO 8
<211> LENGTH: 9
<212> TYPE: DNA
<213> ORGANISM: Artificial Sequence
<220> FEATURE:
<223> OTHER INFORMATION: Synthetic

<400> SEQUENCE: 8 tcttcttga                                                                 9

<210> SEQ ID NO 9
<211> LENGTH: 9
<212> TYPE: DNA
<213> ORGANISM: Artificial Sequence
<220> FEATURE:
<223> OTHER INFORMATION: Synthetic
```

```
<400> SEQUENCE: 9 ttctcgcct                                                                9

<210> SEQ ID NO 10
<211> LENGTH: 9
<212> TYPE: DNA
<213> ORGANISM: Artificial Sequence
<220> FEATURE:
<223> OTHER INFORMATION: Synthetic

<400> SEQUENCE: 10 tcctgctgt                                                                9

<210> SEQ ID NO 11
<211> LENGTH: 9
<212> TYPE: DNA
<213> ORGANISM: Artificial Sequence
<220> FEATURE:
<223> OTHER INFORMATION: Synthetic

<400> SEQUENCE: 11 ttttccaga                                                                9

<210> SEQ ID NO 12
<211> LENGTH: 9
<212> TYPE: DNA
<213> ORGANISM: Artificial Sequence
<220> FEATURE:
<223> OTHER INFORMATION: Synthetic

<400> SEQUENCE: 12 gtttcagca                                                                9

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
ggctagctac aacga                                                        15

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
agcaacatcg atcgg                                                        15

<210> SEQ ID NO 15
<211> LENGTH: 19
<212> TYPE: RNA
<213> ORGANISM: Artificial Sequence
<220> FEATURE:
<223> OTHER INFORMATION: Artificial Sequence

<400> SEQUENCE: 15
ugcugaaacg cgagagaaa                                                    19

<210> SEQ ID NO 16
<211> LENGTH: 19
```

```
<212> TYPE: RNA
<213> ORGANISM: Artificial Sequence
<220> FEATURE:
<223> OTHER INFORMATION: Artificial Sequence

<400> SEQUENCE: 16
ucaagaagaa uggagcgau                                                    19

<210> SEQ ID NO 17
<211> LENGTH: 19
<212> TYPE: RNA
<213> ORGANISM: Artificial sequence
<220> FEATURE:
<223> OTHER INFORMATION: Synthetic

<400> SEQUENCE: 17
aggcgagaaa uacgccuuu                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
acagcaggag ucuuggcua                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
ucuggaaaaa ugaaccaac                                                    19

<210> SEQ ID NO 20
<211> LENGTH: 17
<212> TYPE: RNA
<213> ORGANISM: Artificial Sequence
<220> FEATURE:
<223> OTHER INFORMATION: Synthetic

<400> SEQUENCE: 20
ugcugaaacg cgagaaa                                                      17

<210> SEQ ID NO 21
<211> LENGTH: 31
<212> TYPE: DNA
<213> ORGANISM: Artificial Sequence
<220> FEATURE:
<223> OTHER INFORMATION: Synthetic sequence conjugated to thiol linker
      at 5' end
<220> FEATURE:
<221> NAME/KEY: misc_structure
<222> LOCATION: (1)..(1)
<223> OTHER INFORMATION: A thiol linker HS-(CH2)6- is conjugated to the
      5' end of the DNAzyme sequences, residues 1-end.

<400> SEQUENCE: 21
agccaaaagg ctagctacaa cgatcctgct g                                      31

<210> SEQ ID NO 22
<211> LENGTH: 31
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_structure
<222> LOCATION: (1)..(1)
<223> OTHER INFORMATION: A thiol linker HS-(CH2)6- is conjugated to the
      5' end of the DNAzyme sequences, residues 1-end.

<400> SEQUENCE: 22
aaggcgtagg ctagctacaa cgattctcgc c                                31

<210> SEQ ID NO 23
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_structure
<222> LOCATION: (1)..(1)
<223> OTHER INFORMATION: A thiol linker HS-(CH2)6- is conjugated to the
      5' end of the DNAzyme sequences, residues 1-end.

<400> SEQUENCE: 23
agccaagagg ctagctacaa cgatcctgct g                                31

<210> SEQ ID NO 24
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_structure
<222> LOCATION: (1)..(1)
<223> OTHER INFORMATION: A thiol linker HS-(CH2)6- is conjugated to the
      5' end of the DNAzyme sequences, residues 1-end.

<400> SEQUENCE: 24
ttggttcggc tagctacaac gattttccag                                  30

<210> SEQ ID NO 25
<211> LENGTH: 21
<212> TYPE: DNA
<213> ORGANISM: Chikungunya virus
<220> FEATURE:
<221> NAME/KEY: misc_feature
<222> LOCATION: (1)..(21)
<223> OTHER INFORMATION: CDZ 5' arm target corresponds to nucleotides
      202 to 210 of the CHIKV genome

<400> SEQUENCE: 25
aatgctagag cgttctcgca t                                           21

<210> SEQ ID NO 26
<211> LENGTH: 9
<212> TYPE: DNA
<213> ORGANISM: Artificial Sequence
<220> FEATURE:
<223> OTHER INFORMATION: CDZ 5' Arm sequence

<400> SEQUENCE: 26 atgcgagaa                                                          9

<210> SEQ ID NO 27
<211> LENGTH: 9
<212> TYPE: DNA
<213> ORGANISM: Artificial Sequence
```

-continued

```
<220> FEATURE:
<223> OTHER INFORMATION: CDZ 3' Arm sequence

<400> SEQUENCE: 27 gctctagca                                                                  9

<210> SEQ ID NO 28
<211> LENGTH: 21
<212> TYPE: RNA
<213> ORGANISM: Chikungunya virus
<220> FEATURE:
<221> NAME/KEY: misc_feature
<222> LOCATION: (1)..(21)
<223> OTHER INFORMATION: CHIKV RNA Target sequence

<400> SEQUENCE: 28
aaugcuagag cguucucgca u                                                   21

<210> SEQ ID NO 29
<211> LENGTH: 33
<212> TYPE: DNA
<213> ORGANISM: Artificial Sequence
<220> FEATURE:
<223> OTHER INFORMATION: Nucleotide sequence portion of thiol-CDZ
      conjugate 5'-SH-(CH2)6-d(TTTCTCTCGGGCTAGCTACAACGAGTTTCAGCA)-3'

<400> SEQUENCE: 29
tttctctcgg gctagctaca acgagtttca gca                                      33

<210> SEQ ID NO 30
<211> LENGTH: 23
<212> TYPE: DNA
<213> ORGANISM: Artificial Sequence
<220> FEATURE:
<223> OTHER INFORMATION: Forward primer binds to nucleotide postions
      2631-2653 of the CHIKV genome.

<400> SEQUENCE: 30
tgaccgccat tgtgtcatcg ttg                                                 23

<210> SEQ ID NO 31
<211> LENGTH: 22
<212> TYPE: DNA
<213> ORGANISM: Artificial Sequence
<220> FEATURE:
<223> OTHER INFORMATION: Reverse primer binds to nucleotide postions
      2788-2809 of CHIKV genome.

<400> SEQUENCE: 31
gacctcgtat ccacgatagt ca                                                  22

<210> SEQ ID NO 32
<211> LENGTH: 19
<212> TYPE: DNA
<213> ORGANISM: Chikungunya virus
<220> FEATURE:
<221> NAME/KEY: misc_feature
<222> LOCATION: (1)..(19)
<223> OTHER INFORMATION: Corresponds to nucleotides 192 to 210 of the
      CHIKV NS1 gene

<400> SEQUENCE: 32
tgctagagcg ttctcgcat                                                      19
```

DNAZYME-NANOPARTICLE CONJUGATES AND METHODS OF USE THEREOF

CROSS REFERENCE TO RELATED APPLICATIONS

The pending application U.S. Ser. No. 14/757,293, claims priority under 35 U.S.C. § 371 to PCT/US14/42480, filed Monday, Jun. 16, 2014, which claims the benefit of provisional U.S. 61/835,758, filed on Monday, Jun. 17, 2013, and the benefit of provisional U.S. 61/835,173, filed on Friday, Jun. 14, 2013, the disclosures of which are incorporated herein by reference.

STATEMENT REGARDING FEDERALLY-SPONSORED RESEARCH OR DEVELOPMENT

This invention was made with U.S. Government Support under grant RO1-AI-048561 awarded by the NIH/NIAID to Malcolm J. Fraser, Jr. The U.S. Government has certain rights in the invention.

INCORPORATION-BY-REFERENCE OF A SEQUENCE LISTING

The sequence listing contained in the files "761_191_027_US_ST25.txt", created on 2015 Dec. 14, modified on 2015 Dec. 14, file size 7,457 bytes, provided on paper and on two compact discs, and "127191_0024_WO_ST25.txt", created on 2014 Jun. 13, modified on 2014 Jun. 13, file size (7,413 bytes, and "127191_0013_US_ST25.txt", created on 2013 Jun. 14, modified on 2013 Jun. 14, file size 5,586 bytes, and the file "127191_0014_US_ST25.txt", created on 2013 Jun. 17, modified on 2013 Jun. 17, file size 5,586 bytes, are all incorporated by reference in their entirety herein.

FIELD OF THE INVENTION

The present invention relates to DNAzymes (also known as deoxyribozymes, DNA enzymes, catalytic DNA, or DZ) which are conjugated to nanoparticles to facilitate the detection of nucleic acids. In particular, the invention relates to compounds comprising DNAzymes conjugated to nanoparticles, methods for their synthesis, and methods of using the conjugated compounds to detect nucleic acids, such as genomic material or transcripts of viruses and other infectious agents.

Recent epidemics of dengue viruses (DENV) coupled with new outbreaks on the horizon have renewed the demand for novel detection methods that have the ability to identify this viral pathogen prior to the manifestation of symptoms. The ability to detect DENV in a timely manner is essential for rapid recovery from disease symptoms. A modified DNAzyme of the 10-23 family of DNAzymes having RNA endonuclease activity, which is conjugated to gold nanoparticles by a linker, provides a powerful tool for the detection of viruses, such as DENV.

We examined the effectiveness of coupling the activation DNAzymes to the salt-induced aggregation of gold nanoparticles (AuNP) to detect dengue virus progeny in mosquito cells. A DNAzyme was designed to recognize the 5' cyclization sequence (5' CS) that is conserved among all DENV, and conjugated to AuNPs. We demonstrated that DDZ-AuNP conjugates have the ability to detect the genomic RNA of our model dengue strain, DENV-2 NGC, isolated from infected *Aedes albopictus* C6/36 cells. These targeting events lead to the rapid aggregation of AuNPs, resulting in a red to clear color transition of the reaction mixes, providing positive evidence for detection of the RNA genome of dengue virus. DENV could be detected directly from cell culture supernatants without additional sample processing, when SDS was included in the reaction mixture. Specificity assays demonstrated detection is DENV-specific, while sensitivity assays confirm detection at levels of $1\times10^1$ $TCID_{50}$ units. These results demonstrate DDZ-AuNP can be used to detect DENV genomes in a sequence specific manner and at concentrations that are practical for field use.

We have developed an effective detection assay using DNAzyme catalysis coupled with AuNP aggregation for the detection of DENV genomes in a sequence specific manner. Full development of our novel DDZ-AuNP detection method will provide a practical, rapid, and low cost alternative for the detection of DENV in mosquito cells and tissues, and possibly infected patient serum, in a matter of minutes with little to no specialized training required.

BACKGROUND OF THE INVENTION

Dengue viruses (DENV), members of the Flavivirus family of viruses, cause periodic explosive epidemics in many tropical and sub-tropical countries leading to 50-100 million infections per year [World Health Organization (2012)]. Approximately 500,000 of these are severe cases requiring hospitalization with a 2.5% fatality rate, most of which are children [Randolph et al. (2010)]. About half the world's population remains at risk for DENV infection making this pathogen one of the most dangerous viruses in the world [Clyde et al. (2006)]. In 2010 there were 1.6 million cases of dengue in the Americas alone, of which 49,000 were severe cases. Recent domestic outbreaks have occurred in the Hawaiian Islands in 2001, Brownsville, Tex. in 2005 [Ramos et al. (2008)], the Florida Keys in 2010, and other parts of southern Florida including Miami-Dade in 2011 [Anez et al. (2012); Adalja et al. (2012); Effler et al. (2005); World health Organization (2012)]. Devastating outbreaks continue to occur in Puerto Rico, Brazil, and Pakistan [Anez et al. (2012); Figueiredo et al. (2012); Rai (2011)].

CHIKV remained largely unknown until a series of large scale epidemics occurred on several islands in the Indian Ocean in 2005 and 2006 culminating in a catastrophic outbreak on the island of la Reunion, resulting in 265,000 infections and 237 deaths in a population of 775,000 [Tsetsarkin et al. (2006)]. CHIKV has since been imported into Europe by infected travelers returning from endemic areas as evidenced by a CHIKV introduction in the French Riviera [Cordel et al. (2006)]. Most recently, CHIKV outbreaks have occurred and are currently ongoing on multiple Caribbean Islands including St. Maarten, British Virgin Islands, Guadeloupe, Martinique, Saint Barthelemy, and French Guiana [Van Bortel et al. (2014)]. These statistics, coupled with the worldwide distribution of *Aedes aegypti* and *Aedes albopictus* mosquitoes, demonstrate a risk of importing CHIKV into new areas, including the United States[Thiboutot et al. (2010)], through infected travelers.

The CHIKV outbreaks on La Reunion Island are believed to have been primarily facilitated by an Ala to Val (E1 A226V) amino acid substitution in the CHIKV glycoprotein E1 [Tsetsarkin et al. (2009)]. This mutation allowed the virus to traverse the *A. albopictus* gut membrane barrier more efficiently, resulting in a greater degree of dissemination through local swarms [Tsetsarkin et al. (2006)]. This likely provided a selective advantage for *A. albopictus* over *Ae. aegypti* as the insect vector, which accelerated the transmission of CHIKV to an immunological naïve population on la Reunion Island [Tsetsarkin et al. (2009)].

DENV are maintained in a cycle that involves humans and the globally disseminated *Aedes aegypti* mosquito [Roberts et al. (2002)]. Infection with one of four antigenically-distinct, but genetically-related DENV serotypes (designated DENV-1, -2, -3, and -4) can result in dengue fever (DF), dengue hemorrhagic fever (DHF), which can be fatal, or both DF and DHF [Qi et al. (2008)]. These disease states are characterized by high fever, often with enlargement of the liver, and in severe cases, circulatory and respiratory failure [Rigau-Perez et al. (1998)].

While DF and DHF are endemic to tropical and subtropical regions of the world, collapse of effective vector control programs, rapid dispersal of viruses due to ease of global travel, and migration of humans from tropical to non-tropical regions has resulted in DENV outbreaks in regions that were once non-endemic to these viral pathogens.

The ability to detect DENV in a timely manner is essential to rapid recovery from disease symptoms. Detection of mosquito-borne viruses in infected humans is currently limited to plaque assays, antigen detection assays (e.g. NS1 antigen detection), or quantitation of viral production through PCR-based methods [Lanciotti et al. (1992); Gubler (1998)]. These assays are currently referred to as the "gold standards" for DENV detection [de Oliveira et al. (2005)]. Current methods of testing mosquito populations for arboviruses, particularly dengue and West Nile viruses, has been limited to RT-PCR assays on pools of mosquitos (approximately 50 insects) [Shu et al. (2004); Chisenhall et al. (2008)].

The approaches mentioned above are limited by a number of pitfalls including low-throughput, labor-intensiveness, low stability of assay components at or above room temperature, and lack of portability. The requirement for specialized training and equipment and the time consuming nature of these assays limits their widespread utility for virus detection. These limitations compromise rapid diagnosis of viral infections. These methods are not easily adapted to field environments where reliable and effective detection methods are needed. Rapid, low-tech virus detection methods that require no specialized training or education are sorely needed to provide remote areas of the world the ability to detect highly pathogenic viruses for both clinical diagnosis and epidemiological surveillance.

In this report, we describe the development and initial validation of a colorimetric method for detecting DENV that couples the RNA targeting ability of a DENV-specific DNAzyme (DDZ) with the aggregation properties of oligonucleotide-tethered, non-crosslinking gold nanoparticles (AuNPs). Our new DENV detection system, called DDZ-AuNP (FIG. 1), should be an invaluable tool for the detection of DENV since it solves many of the limitations of current virus detection assays. This assay and subsequent analysis is cost-effective, simple to perform, and the assay components are highly stable at temperatures above 30° C., enabling easy storage at room temperature. The use of DNAzymes in the assay increases the specificity and versatility of detection permitting the design and incorporation of additional virus or strain-specific DNAzymes and probes.

Full development of this detection assay would greatly enhance virus diagnostics and epidemiology by providing an assay that is more rapid, easier to use, has greater portability, and is more cost effective than current DENV detection methods.

BRIEF SUMMARY OF THE INVENTION

One aspect of the invention relates to a compound comprising a DNAzyme (DZ) conjugated to a nanoparticle (NP) by a linker (L), designated DZ-NP, wherein said DNAzyme comprises: a deoxyribonucleic acid (DNA) sequence comprising a 5' Binding Arm (5' BA), a Catalytic Core (CC), and a 3' Binding Arm (3' BA); wherein said 5' and 3' Binding Arms are complementary to two target sequences on a target region of a ribonucleic acid (target RNA) comprising at least one purine-pyrimidine dinucleotide motif.

The invention is also directed to a method wherein said NP is an AuNP, and said aggregation is measured by absorbance or by visual inspection.

The invention is also directed to a kit for detecting the presence, absence, or relative amount of a target nucleic acid in a sample comprising one or more types of DZ-NP conjugates described above.

A better understanding of the invention will be obtained from the following detailed descriptions and accompanying drawings, which set forth illustrative embodiments that are indicative of the various ways in which the principals of the invention may be employed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 sets forth an illustration showing an overview of the DDZ-AuNP assay for dengue virus detection. Schematic of the DENV detection system using DENV-specific DNAzyme (DDZ) catalysis coupled with gold nanoparticle (AuNP) aggregation. AuNPs are conjugated with the sulfide-linked anti-DENV DNAzyme, DDZ, which is complimentary to the DENV RNA genome (shown in orange). Black vertical lines indicate complimentary base pairing between DDZ and the target RNA. In the presence of DENV RNA (A), the 5' and 3' arms of the anti-DENV DNAzyme, DDZ, bind to the 3' and 5' ends of the targeted 5'-3' CS region, respectively (B). When $Mg^{2+}$ and heat (37° C.) are introduced, the DDZ digests the viral RNA (C). The digestion results in deshielding of the AuNP, leading to aggregation of AuNPs in the presence of NaCl and heat (D), allowing a rapid and visually-detectable color transition from red to clear (E). The color transition indicates successful detection of DENV, which can be detected visually or quantified by UV/Vis spectrophotometry at 520 nm AuNPs=red, tethered DNA probe=orange, DENV genome=purple.

FIG. 2 sets forth an illustration showing the basic design of the 10-23 Anti-DENV (DDZ) and Anti-CHIKV (CDZ) DNAzymes and schematic diagram of the DENV and CHICKV genomes. A) DDZ was designed and produced as previously described [Cairns et al. (2003)]]. R=Purine. Y=Pyrimidine. The target RNA is in green with the anti-DENV DNAzyme 10-23 shown in black. The 5' and 3' ends of target RNA and DNAzymes are as indicated. Thin black vertical lines show complimentary base pairing. Arrows indicate cleavage site of the target RNA. B) A representation of the 10,723 base DENV-2 NGC GC capped and polyadenylated genome is shown to illustrate the position of the region targeted by the anti-DENV DNAzyme, DDZ. Non-structural (NS) genes 1 through 5 are shown in green. Structural genes encoding capsid, membrane glycoprotein precursor, and envelope proteins are shown in red. UTR=untranslated region, PA=polyadenylation. C) A representation of the 12036 base CHICKV vaccine 181/25 strain, with its conserved region near its 5'Untranslated Region (UTR), and the junction region separating segments encoding nonstructural proteins from structural proteins, plus its 3'UTR.

FIG. 5 sets forth an illustration showing determination of optimal NaCl and SDS concentrations. A) The optimal concentration of sodium, in the form of NaCl, for aggregation of DDZ-M-AuNP following interaction with the DENV-2 RNA genome was determined. DENV-2 NGC strain genomic RNAs were isolated using the RNeasy Mini Kit (Qiagen) and 0.6 µM was incubated in a reaction mix containing DDZ-M-AuNP ($1 \times 10^5$ particles/mL), 10 mM $MgCl_2$, and increasing concentrations of NaCl (0 to 2 M) for 30 minutes at 37° C. A representative photograph of the reaction tubes is shown. The concentration of NaCl is indicated above each reaction tube. A full red to clear color transition indicates the optimum detection of the DENV-2 NGC genome. 1.5 M NaCl was determined to be the minimal optimum concentration of NaCl to use in our DENV detection reactions. B) The optimal concentration of SDS was determined in the presence of DENV-2 NGC virions. C6/36 cells were infected with DENV-2-NGC (MOI=0.1). At 6 dpi, 10 µl of cell supernatants containing $1 \times 10^6$ DENV-2 NGC/mL, as determined by $TCID_{50}$-IFA, were added to a reaction mix containing 10 mM $MgCl_2$, $1 \times 10^5$ DDZ-M-AuNP particles/mL, 1.5 M NaCl, and 0% (w/v) to 1% (w/v) SDS detergent. Samples were incubated at 37° C. for 30 minutes and photographs were taken. Results demonstrate that the DDZ-M-AuNP colorimetric method for DENV detection occurs optimally in 0.5% SDS. The percent SDS used is indicated above each microcentrifuge tube. SDS=sodium dodecyl sulfate.

FIG. 7 sets forth an illustration showing an assessment of DDZ-AuNP specificity. A) DENV-2 and CHIKV ($1 \times 10^6$/mL each) were placed in a buffered solution containing 10 mM $MgCl_2$, $1 \times 10^5$ DDZ-AuNP particles/mL, 1.5 M NaCl, and 0.5% (w/v) SDS. Microcentrifuge tubes containing these mixes were incubated at 37° C. for 30 minutes and photographed. CHIKV=chikungunya virus. DENV-2=dengue virus serotype 2, DDZ-M=anti-dengue virus DNAzyme, DDZin-M=inactive anti-dengue virus DNAzyme. B) Analysis of DENV detection by UV/Vis Spectrophotometry. Samples were assembled as was performed for in A., mixed, incubated at 37° C. for 5 minutes, and spectrophotometric analysis was performed using the ND-1000 spectrophotometer. C) Detection of DENV by DDZ-M-AuNP in comparison to several other flaviviruses. The specificity of our DDZ-M-AuNP conjugate to detect DENV and no other fellow Flavivirus members YFV, JEV or ZV was determined as described earlier (see FIG. 4). D) An alignment was performed on consensus sequences of each of the four DENV serotypes to determine the most optimal regions for the design of serotype specific DDZ-AuNP devices by determining the region of least conservation one serotype has with the other DENV serotypes. E) Colorimetric serotype-specific detection of DENV. Cell culture supernatants from C6/36 cells mock infected (Mock), or from cells infected with either DENV serotypes 1 through 4 or CHIKV ($1 \times 10^6$/mL each) were placed in buffered solutions containing the necessary cofactors and AuNPs tethered with our all-purpose DENV serotype specific DNAzyme, DDZ-M, or one of the serotype-specific DDZs (designated DDZ-1 through-4) designed to specifically target the corresponding DENV serotype (Table E-3). Microcentrifuge tubes containing these mixes were incubated at 37° C. for 5 minutes and photographed.

FIG. 8 sets forth an illustration showing an analysis of DDZ-AuNP Sensitivity. A) DDZ-M-AuNP colorimetric assays were performed on DENV-2 NGC titers of $1 \times 10^1$, $1 \times 10^2$, $1 \times 10^4$, and $1 \times 10^6$ to determine the limits of detection. Samples were assembled as described earlier (see FIG. 7), incubated at 37° C. for 30 minutes and photographed. Results show that the DDZ-M-AuNP colorimetric assay is capable of detecting DENV-2 at a titer as low as $1 \times 10^1$. DDZ-M=anti-dengue virus DNAzyme, DDZin-M=inactive anti-dengue virus DNAzyme. B) Analysis of DDZ-AuNP sensitivity by UV/Vis spectrophotometry. Ten microliters (10 µL) of cell culture fluid from Mock, DENV-2 NGC (titers of $1 \times 10^1$, $1 \times 10^2$, $1 \times 10^6$/mL), or CHIKV vaccine strain 181/25 ($1 \times 10^6$/mL) infected C6/36 cells, or DENV serially diluted from $1 \times 10^1$ (Dil1 through Dil5) or were added to separate mixtures as described in A). UV/Vis spectrophotometric analysis was performed using the ND-1000 spectrophotometer at an absorbance of 520 nm. Absorbance measurements were graphed in log scale to illustrate sensitivity and accuracy of the colorimetric DENV detection method.

FIG. 9, panels A-C set forth illustrations showing alignment of CHIKV genomic sequences to identify appropriate target regions and vitro analysis of CDZ-AuNP detection of CHIKV RNA targets. Panel 9A. A synthetic stretch of ribonucleotides corresponding to the target site of the CHIKV RNA genome of each serotype were added to a buffered mixture containing 10 mM $MgCl_2$, $2 \times 10^8$ CDZ-AuNP particles, and 1.0 M NaCl. Samples were incubated at 37° C. for 5 minutes and photographs were taken. Control samples were treated the same as the experimental samples, except that inactive versions of the DNAzymes were used in lieu of the active forms. Aggregation of CDZ-tethered AuNPs only occurred in the presence of synthetic CHIKV RNA. Results indicate that CDZ-AuNPs have the ability to detect CHIKV. CDZ=anti-CHIKV DNAzyme. CDZin=inactive anti-CHIKV DNAzyme. Panel 9B. CDZ-AuNPs ($2\times10^8$ particles/mL) were placed in a buffered solution containing 10 mM $MgCl_2$, CHIKV RNAs (0.6 μM) isolated from *Ae. albopictus* C6/36. Following incubation at 37° C. for 30 minutes, RT-PCR was performed as described in Methods to amplify digestion products. Fragments were then separated on a 1.75% TAE agarose gel in the presence of ethidium bromide and photographed under UV light. Arrows indicate digestion products of approximately 200 and 300 bases and the primer dimer, respectively. Results demonstrate CDZ digestion of full length CHIKV genome in spite of AuNP conjugation. CDZ=anti-dengue virus DNAzyme, CDZin=inactive anti-dengue virus DNAzyme. Panel 9C. An alignment was performed of twenty five (25) CHIKV genomic sequences to determine the most optimal regions for the design of the chikungunya virus specific CDZ-AuNP device by determining the region of the greatest conservation within the CHIKV serotypes. CHIKV Con=Chikungunya virus conserved region. Contains the CDZ target sequence. Nucleotide sequences in yellow indicate complete conservation. Nucleotide sequences in blue indicate partial conservation. Nucleotide sequence position is indicated at the top of the figure. GenBank Accession Numbers at the left of the figure indicate the CHIKV sequence aligned.

FIG. 11 sets forth an illustration showing determination of optimal SDS concentrations for CHIKV detection. The optimal SDS concentration was determined in the presence of CHIKV virions. C6/36 cells were infected with CHIKV (MOI=0.1). At 2 dpi, 10 μl of cell supernatants containing $1\times10^6$ CHIKV/mL, as determined by $TCID_{50}$-IFA, were added to a reaction mix containing 10 mM $MgCl_2$, $2\times10^8$ CDz-AuNP particles, 1.5 M NaCl, and 0% (w/v) to 1% (w/v) SDS detergent. Samples were incubated at 37° C. for 30 minutes and photographs were taken. CDz-AuNP colorimetric method for CHIKV detection occurs optimally in 0.5% SDS. The percent SDS used is indicated above each microcentrifuge tube. SDS=sodium dodecyl sulfate.

FIG. 13 sets forth an illustration showing an assessment of CDZ-AuNP specificity. CHIKV and DENV-2 NGC ($1\times10^6$/mL each) were placed in separate reaction tubes possessing a buffered solution containing 10 mM $MgCl_2$, $2\times10^8$ CDZ-AuNP particles, 1.5 M NaCl, and 0.5% (w/v) SOS. Microcentrifuge tubes containing these mixes were incubated at 37° C. for 30 minutes and photographed. CDZin refers to the anti-CHIKV DNAzyme that has been rendered inactive through inversion of the oligonucleotides encompassing the catalytic domain. The inversion mutation of the catalytic domain is designed to knock out cleavage function, providing a negative control. CDZ-AuNP demonstrated CHIKV specificity in this assay since AuNP aggregation is only evident in the sample tube inoculated with CHIKV. CHIKV=chikungunya virus. DENV-2=dengue virus serotype 2, CDZ=anti-dengue virus DNAzyme, CDZin=inactive anti-dengue virus DNAzyme.

FIG. 14 sets forth an illustration showing an analysis of the CDZ-AuNP Limits of CHIKV Detection. A. CDZ-AuNP colorimetric assays were performed on CHIKV titers of $1\times10^1$, $1\times10^2$, $1\times10^4$, and $1\times10^6$ to determine the limits of detection. Samples were assembled for CHIKV detection as described in EXAMPLE 1, incubated at 37° C. for 30 minutes and photographed. Results show that the CDZ-AuNP colorimetric assay is capable of detecting CHIKV at a titer as low as $1\times10^1$. CDZ=anti-dengue virus DNAzyme, CDZin=inactive anti-dengue virus DNAzyme. B. Titers of CHIKV containing samples were confirmed by $TCID_{50}$-immunofluorescence assays (IFA). We used immunofluorescence detection of cell surface expressed CHIKV E protein in C6/36 cultures infected with serial 10 fold dilutions to assess CHIKV titer as previously described [Nawtaisong et al. (2009)]. 10 fold serial dilutions of infected C6/36 cell culture supernatants were harvested at 48 hpi and used as inoculum for 96 well plate cultures of naïve C6/36 cells. Plates were incubated for 4 days at 28° C. without $CO_2$, washed, fixed with acetone:DPBS (3:1), and stained with a primary CHIKV envelope (E) antibody (1:200) [Henchal et al. (1985)], followed by a biotinylated-streptavidin detection system conjugated with FITC (Amersham Biosciences, Piscataway, N.J.). Wells displaying cellular fluorescence were scored as positive for CHIKVV infection. The number of positive wells were counted and the virus titers calculated according to Karber's method [Karber (1931)].

FIG. 15 sets forth an analysis of CDZ-AuNP sensitivity by UV/Vis spectrophotometry at 520 nm. Cell culture fluids (10 μl) from mock, CHIKV vaccine strain 181/25 (titers of $1\times10^1$, $1\times10^2$ and $1\times10^6$/mL), or DENV-2 NGC ($1\times10^6$/mL) infected C6/36 cells, or CHIKV serially diluted from $1\times10^1$ (Dil1 through Dil5) or were added to separate mixtures. UV/Vis spectrophotometric analysis was performed using the ND-1000 spectrophotometer at an absorbance of 520 nm. Absorbance measurements were graphed in log scale to illustrate sensitivity and accuracy of the colorimetric CHIKV detection method. A. Positive detection of CHIKV can be determined by the color change of the sample tubes, although the desired full red to clear/colorless color change was not evident for $10^1$/ml or $10^2$/ml, but rather a red to pale purple color change was achieved. Though this color change signifies positive detection of CHIKV, further assessment of the sensitivity of our colorimetric CHIKV detection assay was performed by UV /Vis spectrophotometry using standardized titers of CHIKV. B. Titers of CHIKV containing samples were confirmed by $TCID_{50}$-immunofluorescence assays (IFA). We used immunofluorescence detection of cell surface expressed CHIKV E protein in C6/36 cultures infected with serial 10 fold dilutions to assess CHIKV titer as previously described [Nawtaisong et al. (2009)]. 10 fold serial dilutions of infected C6/36 cell culture supernatants were harvested at 48 hours post infection (hpi) and used as inoculum for 96 well plate cultures of naïve C6/36 cells.

Plates were incubated for 4 days at 28° C. without $CO_2$, washed, fixed with acetone:DPBS (3:1), and stained with a primary CHIKV envelope (E) antibody (1:200) [Henchal et al. (1985)], followed by a biotinylated-streptavidin detection system conjugated with FITC (Amersham Biosciences, Piscataway, N.J.). Wells displaying cellular fluorescence were scored as positive for CHIKVV infection. The number of positive wells were counted and the virus titers calculated according to Karber's method [Karber (1931)].

Figure 16:
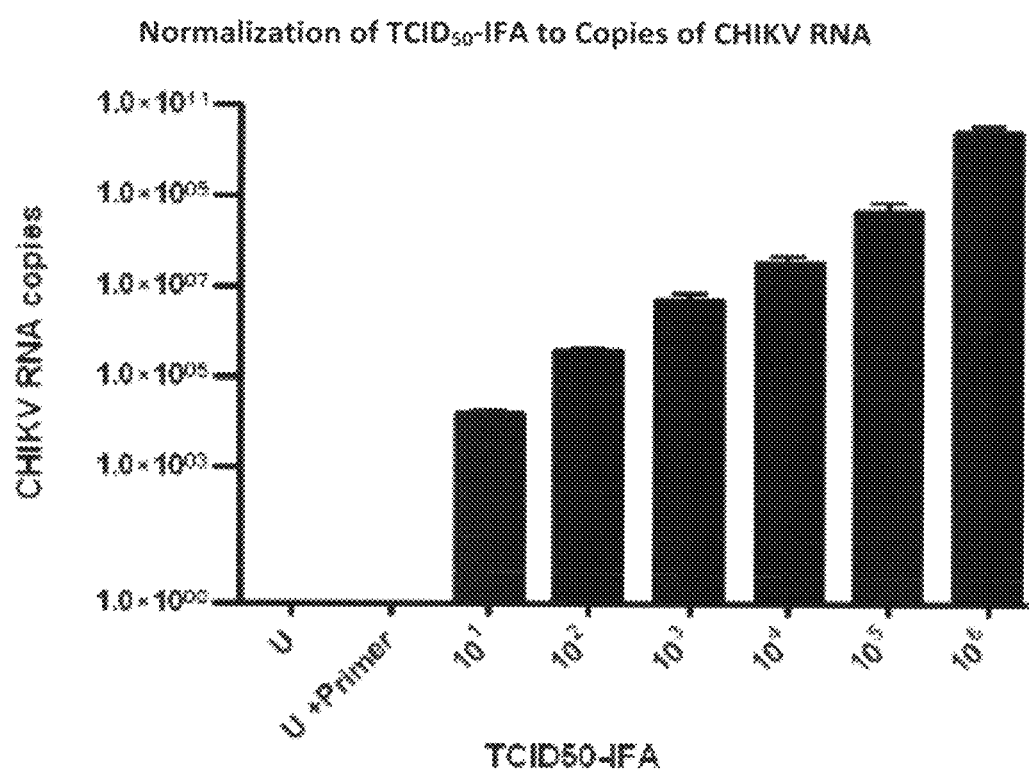

FIG. 16 sets forth an illustration showing normalization of $TCID_{50}$-IFA to copies of CHIKV RNA. C6/36 cells in T-25 flasks were infected with CHIKV vaccine strain 181/25 (MOI=0.001). At 4 dpi cell supernatants were collected, ten-fold serial dilutions were produced and analyzed by $TCID_{50}$-IFA and RT-PCR for the relation of infectious units to RNA copies, respectively, as described in Materials and Methods and in the text. Results were expressed as titers of $10^1$ through $10^6$ $TCID_{50}$ units/ml against RNA copy number ($\times 10^n$). Negative control samples consisted of samples containing RNA from uninfected C6/36 cells without primers (designated on the graph as "U") and samples containing RNA from uninfected C6/36 cells with CHIKV-specific primers (designated on the graph as "U+ primers").

The following is a list of terms and their definitions used throughout the specification and the claims:

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as a transgenic organism.

The term "isolated" when used with respect to a polynucleotide (e.g., single- or double-stranded RNA or DNA), an enzyme, or more generally a protein, means a polynucleotide, an enzyme, or a protein that is substantially free from the cellular components that are associated with the polynucleotide, enzyme, or protein as it is found in nature. In this context, "substantially free from cellular components" means that the polynucleotide, enzyme, or protein is purified to a level of greater than 80% (such as greater than 90%, greater than 95%, or greater than 99%).

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; ug, μg=micro gram(s); ul, μl=micro liter(s); uM, μM=micromolar.

Specific abbreviations and their corresponding meanings include: NP=nanoparticle; AuNP=gold nanoparticle; DDZ=dengue virus targeting DNAzyme; L=linker; DDZ-M=universal dengue virus targeting DNAzyme; DDZ-1=DNAzyme targeting dengue virus serotype 1; DDZ-2=DNAzyme targeting dengue virus serotype 2; DDZ-3=DNAzyme targeting dengue virus serotype 3; DDZ-4=DNAzyme targeting dengue virus serotype 4. CDZ=CHIKV targeting DNAzyme.

DETAILED DESCRIPTION OF THE INVENTION

The present invention relates to compounds comprising DNAzyme (DZ) conjugated to a nanoparticle (NP) by a linker (L), designated DZ-NP, methods of detecting nucleic acids having specific target sites using the DZ-NP conjugates, and stable compositions comprising the DZ-NP conjugates. The conjugates encompass virus-specific DNAzymes, such as dengue virus-specific DNAzymes (DDZ), and chikungunya virus-specific DNAzymes (CDZ). Other types of virus-specific DNAzymes are also encompassed by the invention.

One aspect of the invention relates to a compound comprising a DNAzyme (DZ) conjugated to a nanoparticle (NP) by a linker (L), designated DZ-NP, wherein said DNAzyme comprises: a deoxyribonucleic acid (DNA) sequence comprising a 5' Binding Arm (5' BA), a Catalytic Core (CC), and a 3' Binding Arm (3' BA); wherein said 5' and 3' Binding Arms are complementary to two target sequences on a target region of a ribonucleic acid (target RNA) comprising at least one purine-pyrimidine dinucleotide motif.

Related aspects are directed to a DZ-NP wherein said DNAzyme is an RNA-Cleaving DNAzyme selected from the group consisting of a 10-23 DNAzyme and a 8-17 DNAzyme. Other aspects are directed to a DZ-NP wherein said DNAzyme is selected from $UO_2^{2+}$-dependent and $Mg^{2+}$-independent DNAzymes.

The nanoparticles used in the invention may be different shapes, typically a sphere, but also including shapes selected from a rod, a polygonal rod, rectangular block, cube, tetrapod, and pyramid.

Related aspects are directed to a DZ-NP wherein nanoparticle is a quantum dot. Quantum dots are tiny particles, or 'nanoparticles', of a semiconductor material, traditionally chalcogenides, such as selenides or sulfides, of metals like cadmium or zinc (e.g., CdSe or ZnS), ranging in size from 2 nm to 10 nm in diameter. Quantum dots have unique optical and electrical properties that are often different in character from those observed in the corresponding bulk material. One prominent difference is the emission of photons under excitation, which are visible to the human eye as light. The wavelength of photon emissions depend on the size, and not on the material, from which the quantum dot is made. Gold quantum dots can also be produced by a variety of methods [Goho (2004)].

The nanoparticles may be comprised of different substances, which may be homogeneous, or pure, such as a metal (designated a metallic nanoparticle, mNP), or a non-metallic substance (designated a non-metallic nanoparticle, nmNP), or they may be made of composite materials (designated a composite nanoparticle, cNP) comprised of two or more substances, such as a metallic and a non-metallic substance. Non-metallic nanoparticles may comprise one or more substances selected from the group consisting of carbon, dextrose, solid lipid nanoparticles, dextran, chitosan. A composite nanoparticle comprises a composite material comprising a metallic and a non-metallic substance. The nanoparticles may also comprise one or more substances selected from the group consisting of: gold, silver, iron, titanium, platinum, cerium, silicon, palladium, transition metals, and oxides thereof. Nanoparticles that comprise two or more metallic substances, or oxides thereof, are designated multi-metallic nanoparticles (mmNP). Nanoparticles that comprise metal are designated metallic nanoparticles (mNP). One aspect of the invention is directed to gold nanoparticles (AuNP), which are typically spherical, ranging in size from about 1 nm to about 400 nm in diameter. The range of sizes in a population of particles may vary, with a narrow or broad distribution of sizes in a sample, based on the source of the particles, and the process used to manufacture or purify particles of different shapes and sizes.

Related aspects are directed to DZ-NP conjugates wherein the DZ is linked to said nanoparticle by a linker through two or more covalent bonds, designated a covalent linker (cL). In one aspect, the covalent linker comprises —SH—$(CH_2)_6$—. In other aspects, said covalent linker comprises Streptavidin fluorescent conjugates, acridine and Azobenzene fluorescent conjugates, Biotin, Biotin Diol Linker, Biotin TEG, Biotin BB, Desthiobiotin TEG, DOTA (1,4,7,10-Tetraazacyclodo-decane-1,4,7,10-tetraacetic acid), Dual Biotin, Photocleavable (PC) Biotin, Psoralen C2, Psoralen C6, Fluorescein, FITC, TRITC, fluorescent proteins (e.g. GFP, YFP, and RFP), 2 modified NTPs (e.g. 2' fluoro dC (fC), 2' amino and 2' OMe analogs), polyethylene glycol (PEG) transport molecules, acetyl-PEG-amine, Carboxy-PEG-Amine. In other aspects, the DDZ is linked to said nanoparticle by a linker through one or more high-affinity noncovalent bonds, designated a high affinity noncovalent linker (hancL), such as a linker that comprises biotin.

The DZ-NP conjugates can be configured to target different nucleic acids. One aspect is directed to a target nucleic acid which is an RNA, such as a viral RNA. In one aspect, the viral RNA is a genomic viral RNA, and in another aspect the viral RNA is a viral RNA transcript. Different types of viral RNAs may be targeted.

In one aspect the DZ-NP conjugate is designed to target a viral RNA is a Flavivirus RNA, such as a Flavivirus selected from a group consisting of in a mammalian tick-borne flaviviruses, mosquito-borne viruses, and viruses with no known arthropod vectors. In one aspect the Flavivirus is a mosquito-borne virus selected from the group consisting of Avian tembusu-related virus, Calbertado virus, Chaoyang virus, Aroa virus, dengue virus, Japanese encephalitis virus, Kokobera virus, Ntaya virus, Spondweni virus, Zika virus, and Yellow fever virus group. Another aspect is directed to a viral RNA wherein said virus is a Flavivirus, exemplified by dengue virus, and said dengue virus RNA is a dengue virus genomic RNA.

In one aspect the DZ-NP conjugate is designed to target a viral RNA is an Alphavirus RNA, such as an RNA from Alphavirus that is in a complex selected from the group consisting of Barmah Forest virus, Eastern equine encephalitis, Middleburg virus, Ndumu virus, Semliki Forest virus, Sindbis virus, Venezuelan equine encephalitis, Western equine encephalitis, unclassified Alphaviruses, and recombinant viruses within each complex. In another aspect, the DDZ-NP conjugate targets an Alphavirus is in the Semliki Forest Virus complex, such as chikungunya virus.

The DZ-NP conjugate may be designed to target specific residues within a target RNA. In one aspect the target region of a ribonucleic acid (target RNA) comprises at least one purine-pyrimidine dinucleotide motif within a coding sequence which encodes a polypeptide. In another aspect, the target region of a ribonucleic acid (target RNA) comprises at least one purine-pyrimidine dinucleotide motif within a noncoding sequence. In another aspect, the target region is a viral 5'-3' Cyclization Sequence (CS). The target region of the conjugates designated DDZ-M or DDZin-M is a viral 5'-3' Cyclization Sequence (CS), exemplified by the dengue virus

```
                                         (SEQ ID NO: 15)
    5'-3' CS UGCTGAAACGCGAGAGAAA.
```

In other aspects, the target region of conjugates designated DDZ-1, DDZ-2, DDZ-3, and DDZ-4 is a conserved region, specific to each virus serotype, exemplified by

```
DDZ-1
                                         (SEQ ID NO: 16)
    UCAAGAAGAAUGGAGCGAU;
```

```
DDZ-2
                                         (SEQ ID NO: 17)
    AGGCGAGAAAUACGCCUUU;

DDZ-3
                                         (SEQ ID NO: 18)
    ACAGCAGGAGUCUUGGCUA;
and DDZ-4
                                         (SEQ ID NO: 19)
    UCUGGAAAAUGAACCAAC,
``` respectively.

The DDZ-NP conjugate has a catalytic core, which may vary depending on the class of DNAzyme. One aspect of the invention is directed to a DDZ-NP conjugate wherein said catalytic core (CC) is

```
                                         (SEQ ID NO: 13)
    GGCTAGCTACAACGA.
```

The DDZ-NP conjugate also comprise a pair of specific sequences, designated arms that facilitate the binding of the conjugate to a target nucleic acid sequence. In one aspect, the DDZ-NP comprises a 5' Arm and a 3' Arm that are a pair of sequences selected from the group consisting of:

```
                                         (SEQ ID NO: 1)
    TTTCTCTCG
and
                                         (SEQ ID NO: 7)
    GTTTCAGCA;

(SEQ ID NO: 2)
    ATCGCTCCA
and
                                         (SEQ ID NO: 8)
    TCTTCTTGA;

(SEQ ID NO: 3)
    AAAGGCGTA
and
                                         (SEQ ID NO: 9)
    TTCTCGCCT;

(SEQ ID NO: 4)
    TAGCCAAGA
and
                                         (SEQ ID NO: 10)
    TCCTGCTGT;
and
                                         (SEQ ID NO: 5)
    GTTGGTTCA
and
                                         (SEQ ID NO: 11)
    TTTTCCAGA.
```

Another aspect of the invention is directed to intermediate products, comprising a nucleic acid targeting sequence conjugated to a linker, which can be activated under appropriate chemical conditions to facilitate attachment of the intermediate to a nanoparticle. One aspect of the invention is directed to a conjugate, or an intermediate, wherein said linker and said DNAzyme designated DDZ-1, DDZ-2, DDZ-3, DDZ-4, DDZ-in-M, are selected from the group consisting of:

thiol-DDZ-1 (SH-DDZ-1)

(SEQ ID NO: 22)
5'-SH-(CH$_2$)$_6$-d(ATCGCTCCAGGCTAGCTACAACGATCTTCTTGA)-3';

thiol-DDZ-2 (SH-DDZ-2)

(SEQ ID NO: 23)
5'-SH-(CH$_2$)$_6$-d(AAAGGCGTAGGCTAGCTACAACGATTCTCGCCT)-3';

thiol-DDZ-3 (SH-DDZ-3)

(SEQ ID NO: 24)
5'-SH-(CH$_2$)$_6$-d(TAGCCAAGAGGCTAGCTACAACGATCCTGCTGT)-3';

thiol DDZ-4 (SH-DDZ-4)

(SEQ ID NO: 25)
5'-SH-(CH$_2$)$_6$-d(GTTGGTTCAGGCTAGCTACAACGAGTTTCAGCA)-3';
and thiol-DDZin-M (SH-DDZin-M)

(SEQ ID NO: 26)
5'-SH-(CH$_2$)$_6$-d(TTTCTCTCGAGCAACATCGATCGGGTTTCAGCA)-3', respectively.

Another aspect is directed to a conjugate wherein DNAzyme and linker are conjugated to a metallic nanoparticle, such as a metallic gold nanoparticle (DNAzyme-AuNP).

The invention is also directed a method of detecting a viral nucleic acid in a sample, comprising the steps of (a) adding the DNAzyme-NP conjugate to a sample comprising nucleic acid in a form which can react with a complementary nucleic acid; (b) heating said sample under conditions which permit the 5' and 3' Binding Arms to bind to the target region in said viral nucleic acid and said catalytic core to cleave at least one purine-pyrimidine dinucleotide motif in said target region; and (c) measuring the increase in aggregation of said nanoparticle conjugates compared to a sample comprising unreacted DNAzyme-NP conjugates in a dispersed form.

One aspect of the invention is directed to a method wherein said NP is an AuNP, and said aggregation is measured by absorbance. Another aspect relates to a method wherein said aggregation is detected by visual inspection. The reaction may be carried out under different conditions, depending on the nature of the components, and the desired degree of sensitivity or speed of reaction. For convenience, the reaction may be carried out in volume of less than 50 µl, in small tubes, for example, or in larger or smaller amounts depending on the number and format of samples being tested, and the instrument used, if required, to monitor the progress of the reaction. In one aspect, the reaction is carried out in the presence of sodium ion in an amount of about 0 to about 2 Moles/Liter, with magnesium ion in an amount of about 5 mM to about 20 mM.

The reaction may be supplemented with a variety of other compounds that facilitate the detection or exposure of nucleic acids in complex mixtures of cellular substances. One aspect of the invention is directed to a method wherein the reaction is carried in the presence of a chaotropic agent or a detergent, such as sodium dodecyl sulfate (SDS), guanidine isothiocyanate, guanidinium chloride, lithium perchlorate, lithium acetate, urea, thiourea, Triton X-100, Triton X-114, Tween 20, Tween 80, NP 40, Brij 35, Brij 80, Octyl glucoside, Octyl thioglucoside, and a zwitterionic detergent selected from CHAPS and CHAPSO. One aspect is directed to a reaction carried out in the presence of the detergent SDS, which may be present in an amount of about 0% to about 1% weight/volume.

The reactions may be carried out at different temperatures. It is convenient to carry out the reaction at room temperature (about 20° C.), but it may also be carried out at higher temperatures, such as from about 20° C. to about 80° C., depending on the stability of the conjugate at higher or lower temperatures, and the availability of thermal regulating equipment, to accelerate or decelerate the reaction as needed.

DZ-NP conjugates that are stable for long periods are desirable, to facilitate transport and storage of key components to diagnostic laboratories, or field locations, where the testing is performed. One aspect of the invention is directed to a conjugate which is stable for a period of at least a year, although shorter or longer periods, one week, one month, one year, two or more years, may be adequate for particular applications, depending on the sensitivity of the assay and the ability of a supplier to produce and ship a conjugate to local or remote locations across the globe.

The invention is also directed to a kit for detecting the presence, absence, or relative amount of a target nucleic acid in a sample comprising one or more types of DZ-NP conjugates described above. One aspect is direct to a kit, wherein the sample is obtained from mammalian tissue, cells, or extracellular fluid. The sample may be blood, for example, or a sample is obtained from a virus-infected cell. Another aspect is directed to a kit wherein the sample is obtained from insect tissue, cells, or extracellular fluid, such as a sample obtained from a virus-infected mosquito, or pool of mosquitos. A further aspect is a kit, wherein the sample comprises nucleic acid from one or more viruses that are co-endemic with dengue virus.

The invention is also directed to DZ-NP conjugates wherein the target region of a chikungunya-specific DNAzyme (CDZ), is a conserved region, specific to each virus serotype. One aspect is directed to a compound designated CDZ, wherein said target region is

SEQ ID NO (28)
AAUGCUAGAGCGUUCUCGCAU.

Another aspect is a compound wherein catalytic core (CC) is (SEQ ID NO: 13)
GGCTAGCTACAACGA.

Another aspect is a compound wherein said 5' Arm and said 3' Arm are a pair of sequences selected from the group consisting of:

(SEQ ID NO: 26)
ATGCGAGAA;
and (SEQ ID NO: 27)
GCTCTAGCA.

Another aspect is a compound wherein said linker and said DNAzyme designated CDZ is thiol-CDZ(SH-CDZ)

(SEQ ID NO: 29)
5'-SH-(CH2)6-d(TTTCTCTCGGCTAGCTACAACGAGTTTCAGCA)-3'.

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

of limitation. Various other examples will be apparent to the person skilled in the art after reading the present disclosure without departing from the spirit and scope of the invention. It is intended that all such other examples be included within the scope of the appended claims.

EXAMPLES

The foregoing discussion may be better understood in connection with the following representative examples which are presented for purposes of illustrating the principle methods and compositions of the invention, and not by way General Materials and Methods Sources of Materials All parts are by weight (e.g., % w/w), and temperatures are in degrees centigrade (° C.), unless otherwise indicated. Table E-1 presents a summary of the nucleotide and amino acid sequences described in this application.

TABLE E-1

Table of Sequences and Conjugated Compounds for DENV Targets

| Name | Description | Length | Type | SEQ ID NO: |
|---|---|---|---|---|
| DDZ-M 5' Arm | tttctctcg | 9 | DNA | 1 |
| DDZ-1 5' Arm | atcgctcca | 9 | DNA | 2 |
| DDZ-2 5' Arm | aaaggcgta | 9 | DNA | 3 |
| DDZ-3 5' Arm | tagccaaga | 9 | DNA | 4 |
| DDZ-4 5' Arm | gttggttca | 9 | DNA | 5 |
| DDZin-M 5' Arm | tttctctcg | 9 | DNA | 6 |
| DDZ-M 3' Arm | gtttcagca | 9 | DNA | 7 |
| DDZ-1 3' Arm | tcttcttga | 9 | DNA | 8 |
| DDZ-2 3' Arm | ttctcgcct | 9 | DNA | 9 |
| DDZ-3 3' Arm | tcctgctgt | 9 | DNA | 10 |
| DDZ-4 3' Arm | ttttccaga | 9 | DNA | 11 |
| DDZin-M 3' Arm | gtttcagca | 9 | DNA | 12 |
| DDZ TABLE E-1-continued Table of Sequences and Conjugated Compounds for DENV Targets

| Name | Description | Length | Type | SEQ ID NO: |
|---|---|---|---|---|
| SH-DDZ-3 | (n) tagccaaga ggctagctac aacga tcctgctgt where Thiol linker HS-(CH$_2$)$_6$- represented by (n) at position 1 is conjugated to DNAzyme sequence, residues 2-end | 33+ | Linker-DNA | 24 |
| SH-DDZ-4 | (n) gttggttca ggctagctac aacga gtttcagca where Thiol linker HS-(CH$_2$)$_6$- represented by (n) at position 1 is conjugated to DNAzyme sequence, residues 2-end | 33+ | Linker-DNA | 25 |
| SH-DDZin-M | (n) tttctctcg agcaacatcg atcgg gtttcagca where Thiol linker HS-(CH$_2$)$_6$- represented by (n) at position 1 is conjugated to DNAzyme sequence, residues 2-end | 33+ | Linker-DNA | 26 |

DNAzyme, RNA Probes, and AuNP

Thiol-modified and unmodified DNAzymes were synthesized and desalted by Life Science Technologies (Grand Island, N.Y., USA). The oligoribonucleotide target was synthesized and HPLC-purified by Life Science Technologies. Quantification of these oligonucleotides was performed with the ND-1000 spectrophotometer from NanoDrop (Wilmington, Del.). Gold colloidal solutions containing 1.6× $10^{12}$ particles/mL gold nanoparticles (AuNPs) with a diameter of 15 nm were purchased from Cytodiagnostics (Burlington, ON, CA).

Cells, Virus and Antibody

*Ae. albopictus* C6/36 cells were obtained from ATCC, and maintained in Leibovitz's L-15 media (Atlanta Biologicals) supplemented with 10% FBS (Atlanta Biologicals), 10% TPB (triptose phosphate broth; Invitrogen/GIBCO), penicillin G (100 U/ml; Invitrogen/GIBCO) and streptomycin (100 µU/ml; Invitrogen/GIBCO). The C6/36 cells used in this study were maintained in a 28° C. incubator and passaged every 4 days. Viral stocks were prepared as previously described [Li et al. (2012)].

The DENV strains and GenBank GenInfo identifiers for the four serotypes used in this study are as follows: DENV type 1 Hawaii: DQ672564.1, DENV type 2 strain New Guinea C (NGC): AF038403.1, DENV type 3 strain ThD3 0010 87 (strain H87): AY676352.1, DENV 4 strain DENV-4/SG/06K2270DK1/2005 (strain H241): GQ398256.1.

Design of the Anti-DENV DNAzyme (DDZ) and Catalytically-Inactive Form (DDZin)

DENV sequence data was obtained from the National Center of Biotechnology Information (NCBI). Sequences representative of all four serotypes of dengue were aligned using ClustalX [Jeanmougin et al. (1998)]. The aligned sequences comprise the following GenBank GenInfo identifiers: 12018173, 12018169, 12018171, 12659201, 2909798, 2909788, 2909786, 2909796, 6841603, 6841595, 6841605, 6841591, 6841601, 6841597, 6841593, 6841599, 6841587, 6841585, 6841589, 1000740, 1000738, 2909784, 1000736, 4926937, 4926935, 4926927, 4926929, 4926931, 2909794, 2909792, 1000742, 4926933, 2155257, 2723944, 323447, 6581076, 6581078, 2723942, 323449, 323650; 18644123, 1864412, 11119731, 19744844, 18644125, 18644127, 18643733, 4337012, 13386495, 1881708, 19071809, 13926152, 9280544, 14585842, 4926947, 4926939, 323654, 4926945, 4926943, 7329983, 7329981, 13540386, 14328931, 14485523, 323660, 17129645, 22901065, 22901063, 22901061, 1854040, 1854038, 1854036, 17129647, 24417519, 24417517, 24417515, 27656962, 24417513, 19071807, 14195698, 8927332, 14328929, 12711599, 323468, 25992053, 25992047, 25992041, 25992029, 25992025, 25992055, 25992033, 19071811, 25992043, 25992039, 25992037, 25992051, 25992031, and 25992057.

The 5' arms of DDZ-M and DDZin-M (Table E-2) were designed to bind to nucleotides 150 to 158 of the DENV genome. The 3' arms were designed to bind to the 5' end of the target region of the DENV genome that corresponds to nucleotides 140 to 148. These 5' and 3' arms of facilitated DDZ cleavage of the substrate DENV RNA between the purine-pyrimidine dinucleotide motifs G149 and C150.

The 5' arm of DDZ-1 was designed to bind nucleotides 319 to 327 of the DENV-1 genome. The 3' arm was designed to bind to the 5' end of the target region of the DENV genome that corresponds to nucleotides 309 to 317. These 5' and 3' arms facilitated DDZ cleavage of the substrate DENV RNA between the purine-pyrimidine dinucleotide motifs A318 and A319. The 5' arm of DDZ-1 was designed to bind nucleotides 319 to 327 of the DENV-1 genome. The 3' arm was designed to bind the 5' end of the target region of the DENV-1 genome that corresponds to nucleotides 309 to 317. These 5' and 3' arms facilitated DDZ-1 cleavage of the substrate DENV-1 RNA between the purine-pyrimidine dinucleotide motifs A318 and A319.

The 5' arm of DDZ-2 was designed to bind nucleotides 126 to 134 of the DENV-2 genome. The 3' arm was designed to bind the 5' end of the target region of the DENV-2 genome that corresponds to nucleotides 116 to 124. These 5' and 3' arms facilitated DDZ-2 cleavage of the substrate DENV-2 RNA between the purine-pyrimidine dinucleotide motifs A124 and A125.

The 5' arm of DDZ-3 was designed to bind nucleotides 288 to 296 of the DENV-3 genome. The 3' arm was designed to bind the 5' end of the target region of the DENV-2 genome that corresponds to nucleotides 278 to 286. These 5' and 3' arms facilitated DDZ-3 cleavage of the substrate DENV-3 RNA between the purine-pyrimidine dinucleotide motifs A287 and G288.

The 5' arm of DDZ-4 was designed to bind nucleotides 95 to 103 of the DENV-4 genome. The 3' arm was designed to bind the 5' end of the target region of the DENV-4 genome that corresponds to nucleotides 85 to 93. These 5' and 3' arms facilitated DDZ-4 cleavage of the substrate DENV-4 RNA between the purine-pyrimidine dinucleotide motifs A94 and A95.

TABLE E-2

Nucleotide sequences of active and negative control DNAzymes and corresponding DENV targets

| DNAzyme | 5'Arm (5'->3') | 3'Arm (5'->3') | Catalytic Core | RNA Target |
|---|---|---|---|---|
| DDZ-M | TTTCTCTCG (SEQ ID NO: 1) | GTTTCAGCA (SEQ ID NO: 7) | GGCTAGCTACAACGA (SEQ ID NO: 13) | UGCUGAAACGCGAGAGAAA (SEQ ID NO: 15) |
| DDZ-1 | ATCGCTCCA (SEQ ID NO: 2) | TCTTCTTGA (SEQ ID NO: 8) | GGCTAGCTACAACGA (SEQ ID NO: 13) | UCAAGAAGAAUGGAGCGAU (SEQ ID NO: 16) |
| DDZ-2 | AAAGGCGTA (SEQ ID NO: 3) | TTCTCGCCT (SEQ ID NO: 9) | GGCTAGCTACAACGA (SEQ ID NO: 13) | AGGCGAGAAAUACGCCUUU (SEQ ID NO: 17) |
| DDZ-3 | TAGCCAAGA (SEQ ID NO: 4) | TCCTGCTGT (SEQ ID NO: 10) | GGCTAGCTACAACGA (SEQ ID NO: 13) | ACAGCAGGAGUCUUGGCUA (SEQ ID NO: 18) |
| DDZ-4 | GTTGGTTCA (SEQ ID NO: 5) | TTTTCCAGA (SEQ ID NO: 11) | GGCTAGCTACAACGA (SEQ ID NO: 13) | UCUGGAAAAAUGAACCAAC (SEQ ID NO: 19) |
| NEGATIVE CONTROL | | | | |
| DDZin-M | TTTCTCTCG (SEQ ID NO: 6) | GTTTCAGCA (SEQ ID NO: 12) | AGCAACATCGATCGG (SEQ ID NO: 14) | UGCUGAAACGCGAGAAA (SEQ ID NO: 20) |

The left column in Table E-2 lists the active (DDZ-M) and inactive (DDZin-M) DNAzymes used in this Example. The second and third columns list the sequences of the 5' and 3' binding arms of the catalytically active DNAzymes and the inactive DDZin-M, respectively. Also shown are the sequences of the catalytic cores of each DNAzyme. The right column lists the nucleotide sequence each binding arm binds to where applicable. All sequences are displayed in a 5' to 3' direction. See the methods section for a description of DNAzyme design.

The DDZ-M target site was selected by scanning the 5' CS domain for one of the purine-pyrimidine dinucleotide motifs required for DNAzyme catalysis [Cairns et al. (2003)]. An alignment of all four known DENV serotypes was performed to determine the ideal target sites for the serotype specific DNAzymes in our DDZ-AuNP detection method (FIG. 7d). Each serotype specific DNAzyme was designed to target each serotype independently of the others. The primary criterion for selection was that a purine-pyrimidine motif located within the target site must be present in all strains of a given DENV serotype. Another important criterion for selecting suitable sites for DDZ cleavage was that the length of conserved flanking arms be long enough to insure specificity of the DNAzyme for the target site. The 5' and 3' arms of each DDZ were 9 bases in length since this was determined to be optimal for DNAzyme catalysis and provides a sufficient level of specificity to insure minimal off-target effects [Cairns et al. (2003)].

Preparation of DDZ-tethered AuNP (DDZ-AuNP)

Preparation of DDZ-M-AuNP was performed as previously described with a few modifications [Liu and Lu (2006)]. The DTT-reduced thiol-DDZ-M
(SEQ ID NO: 21)
5'-SH-(CH2)6-d(TTTCTCTCGGGCTAGCTACAACGAGTTTCAGC A)-3' (SH-DDZ-M)

was purified by ethanol precipitation. 3 ml of AuNP and 5 mM acetate buffer (pH 5.2) were transferred to a glass scintillation vial, capped and incubated for 24 hours at room temperature. Following incubation 5 mM Tris acetate (pH 8.2) buffer and 100 mM NaCl were added and the resulting mixture was incubated at room temperature for an additional 24 hours. These functionalized particles (500 µl) were transferred into 1.7-ml microcentrifuge tubes and centrifuged at 16,110×g at room temperature for 15 min to remove unreacted SH-DDZ-M. The nanoparticles were redispersed in 1 mL of buffer containing 100 mM NaCl, 25 mM Tris acetate, (pH 8.2) and 0.01% SDS, centrifuged again at 16,110×g at room temperature for 15 min. The supernatant was removed and the nanoparticles were dispersed in 500 µl of buffer containing 300 mM NaCl and 25 mM Tris acetate (pH 8.2), and re-centrifuged for 15 min to remove the remaining unreacted SH-DDZ-M. The cleaned DDZ-M-AuNP were redispersed into 200 µL of buffer containing 100 mM NaCl, 25 mM Tris acetate, (pH 8.2) and 0.05% SDS. This same procedure was followed for the coupling of DENV serotype-specific DTT-reduced DNAzymes:

thiol-DDZ-1 (SH-DDZ-1)
(SEQ ID NO: 22)
5'-SH-(CH$_2$)$_6$-d(ATCGCTCCAGGCTAGCTACAACGATCTTCTTG A)-3';

thiol-DDZ-2 (SH-DDZ-2)
(SEQ ID NO: 23)
5'-SH-(CH$_2$)$_6$-d(AAAGGCGTAGGCTAGCTACAACGATTCTCGCC T)-3';

thiol-DDZ-3 (SH-DDZ-3)
(SEQ ID NO: 24)
5'-SH-(CH$_2$)$_6$-d(TAGCCAAGAGGCTAGCTACAACGATCCTGCTG T)-3';

thiol DDZ-4 (SH-DDZ-4)
(SEQ ID NO: 25)
5'-SH-(CH$_2$)$_6$-d(GTTGGTTCAGGCTAGCTACAACGAGTTTCAGC A)-3';
and thiol-DDZin-M (SH-DDZin-M)
(SEQ ID NO: 26)
5'-SH-(CH$_2$)$_6$-d(TTTCTCTCGAGCAACATCGATCGGGTTTCAGC A)-3', Analysis of DDZ-Tethered AuNPs in Detecting a Synthetic DENV-2 Artificial Target DDZ-AuNPs ($1\times10^5$/mL) were combined in a 1.5 mL microcentrifuge tube with 10 mM $MgCl_2$ for optimal DNAzyme activity, 1.0 M NaCl to drive aggregation of AuNPs, and synthetic DENV-2 RNA target (7.5 nM) corresponding to the 5' 170 nucleotides of the virus genome was added [Cairns et al. (2003); Ogawa et al. (2008)]. Reaction mixes were incubated at 37° C. and inspected every 5 minutes over a 30 minute period. Photographs were taken with a Nikon CoolPix S3300 camera (Nikon USA, Melville, N.Y.).

Measurement of $Mg^{2+}$ Resistance of Oligonucleotide-tethered AuNPs

This analysis was performed as previously described [Ogawa et al. (2008)]. A mixture composed of 1 µL of DDZ-tethered AuNPs, 50 mM Tris-HCl (pH 7.5), and increasing concentrations of $MgCl_2$ (5 mM to 20 mM) 10 µl were incubated at room temperature for 0 to ~30 min. Photos of these AuNPs at each incubation time were taken with a Nikon CoolPix S3300 camera, and absorbance units were measured with a ND-1000 spectrophotometer.

In Vitro Analysis of DDZ-tethered AuNPs

DENV RNA was isolated from DENV infected *Ae. albopictus* C6/36 cells using the QiaAmp viral RNA Mini Kit (Qiagen) according to the manufacturer's protocol. 10 µM of eluted DENV RNA was incubated with $1\times10^5$ DDZ-AuNP/ml for 30 min at 37° C. 15 ul of this reaction mixture was added to an RT-PCR mix (Life Science Technologies) containing heterologous and random hexameric primers to amplify the digested fragments. These RT-PCR fragments were then separated on 1.75% agarose gels.

Sodium Dodecyl Sulfate (SDS) Titration Analysis

Ten microliters (10 µl) of cell suspension containing $1\times10^6$ DENV-2 NGC/mL, as determined by $TCID_{50}$-IFA, was added to a mixture containing 150 mM Tris-HCl (pH 7.5), 10 mM $MgCl_2$, $1\times10^5$ DDZ-AuNP particles/mL, 1.5 M NaCl and SDS at concentrations ranging from 0% to 1% (w/v). Samples were incubated at 37° C. for 30 minutes and analyzed every 5 min by visual inspection for aggregation of AuNPs, an indicator of positive detection of in cell culture DENV-2. Photographs were taken with a Nikon CoolPix S3300 camera.

NaCl Titration Assay

DENV-2 NGC RNA were isolated from *Aedes albopictus* C6/36 cells using the QiaAmp Viral RNA mini kit, and added at a concentration of 0.6 µM (~10 µL) to a reaction mixture containing 150 mM Tris-HCl (pH 7.5), 10 mM $MgCl_2$, $1\times10^5$ DDZ-AuNP particles/mL, 0.5% (w/v) SDS, and NaCl (0 M to 2 M). Mixes were incubated at 37° C. for 30 minutes and analyzed every 5 min by visual inspection for aggregation of AuNPs. Samples were analyzed by visual inspection, and photographs taken. Positive detection of DENV-2 NGC RNAs was evident with a complete red to clear color transition occurring with the addition of 1.5 M NaCl.

Determination of DDZ-AuNP Specificity

Ten microliters (10 µL) of cell culture fluid containing $1\times10^6$/mL DENV-2 NGC or, as a negative control, CHIKV vaccine strain 181/25 [Plante et al. (2011)] was added to a mixture containing 150 mM Tris-HCl (pH 7.5), 10 mM $MgCl_2$, $1\times10^5$ DDZ-M-AuNP, DDZin-M-AuNP or any of the serotype-specific DDZ tethered AuNPs/mL, 0.5% (w/v) SDS, and 1.5 M NaCl. Samples were mixed and incubated at 37° C. for 5 minutes, photographs were taken using the Nikon CoolPix S3300 camera, and spectrophotometric analysis was performed using the ND-1000 spectrophotometer.

Analysis of DDZ-AuNP Limits of DENV Detection

DENV-2 NGC of the titers indicated (FIG. 8) were produced as follows. A titer of $1\times10^6$/mL was obtained following inoculation of *Ae. albopictus* C6/36 cells with 0.1 MOI and incubated at 28° C. for 6 dpi. DENV-2 NGC were grown to titers of $1\times10^4$/mL and $1\times10^2$/mL at 3 dpi and 6 dpi, respectively, following inoculation of Vero cells with MOI of 0.1. DENV-2 NGC at a titer of $1\times10^1$/mL were produced by serial dilution of the $1\times10^2$/mL stock. Titers were determined by $TCID_{50}$-IFA as described [Carter et al. (2010)].

The DENV-2 NGC titers described above served as substrates for DDZ-AuNP colorimetric assays to determine their limits of DENV detection. Ten microliters (10 µl) of each dilution stock was added to a buffered reaction mix containing 150 mM Tris-HCl (pH 7.5), 10 mM $MgCl_2$, $1\times10^5$ DDZ-M-AuNP particles/mL, 1.5 M NaCl, and 0.5% (w/v) SDS. Samples were mixed and incubated at 37° C. for 5 minutes and photographs were taken Nikon CoolPix S3300 camera. UV/Vis spectrophotometric analysis was performed using the ND-1000 spectrophotometer.

Example 1

Method of Detecting Dengue Virus with DNAzyme Nanoparticle Conjugates

Results

Overview of the Colorimetric Detection of DENV by DNAzyme Activity Coupled with Non-crosslinking AuNP Aggregation (DDZ-AuNP)

The dengue virus detection method described below (see FIG. 1) is based upon RNA aptazyme-mediated detection of small molecules, such as theophylline [Ferapontova and Gothelf (2009)]. A key limitation of using RNAzymes and aptazymes for virus detection is the inherent instability these catalytic RNAs, increasing the attractiveness of DNAzymes for use in detection assays.

The colorimetric detection of DENV by DDZ-AuNP can be divided into three phases: targeting/cleavage of the DENV RNA genome by DDZ, activation of AuNPs, and aggregation of AuNPs and detection (FIG. 1). In the presence of DENV the 5' and 3' arms of DDZ bind to the 3' and 5' ends of a fully conserved segment that includes the 5'-3' CS region, respectively, and in the presence of $Mg^{2+}$ and heat (37° C.) the viral RNA is cleaved at G149. This cleavage results in deshielding and aggregation of the AuNPs in the presence of NaCl and heat [Ogawa and Maeda (2008)], causing a visually detectable red to clear color transition [Song et al. (2011)] that can be quantified by UV/Vis spectrophotometry at 520 nm [32Song et al. (2011)]. If DENV are not present in the sample, the DNAzyme-tethered AuNPs remain in a dispersed state and no color loss should occur [Song et al. (2011)]. Likewise, if any of the essential components such as magnesium or sodium are not present in the reaction mixture, no aggregation is possible.

Design and in vitro cleavage assessment of the DENV detection system DDZAuNP DNAzymes are lab-derived, auto catalytic DNAs consisting of three intimately connected domains (FIG. 2a): A catalytic core that is activated by binding a cofactor (e.g., $Pb^{2+}$ or $Mg^{2+}$) (though a few DNAzymes do not require a cofactor), and 5' and 3' binding arms that bind to the 3' and 5' regions of the target sequence, respectively [Cieslak et al. (2003); Geyer and Sen (1997)]. DNAzymes have demonstrated impressive sensitivity in detecting metal ions or RNA [Jing et al. (2006); Sun et al. 1999].

The 10-23 DNAzyme is capable of cleaving RNA with high sequence specificity at target sites containing purine-pyrimidine (R-Y) junctions [Santoro and Joyce (1997)]. We chose the 10-23 DNAzyme for use in our DENV detection system, because this DNAzyme is less dependent on secondary structure formation for its activity than other types of DNAzymes, and would be expected to perform better in our in vitro assays where biomolecular folding would be quite variable [Baum and Silverman (2008)]. The design of the anti-DENV 10-23 DNAzyme, DDZ-M (FIG. 2a), was based on a 10-23 DNAzyme clone that was discovered through SELEX (Systematic Evolution of Ligands by Exponential Enrichment). We designed the 5' and 3' arms to target the highly conserved region that includes the 5'-3' cyclization sequence (CS) that is present in all DENV serotypes, and is required for replication of genomic RNA (FIG. 2b; [Alvarez et al. (2005)]).

Gold nanoparticles (AuNPs) ranging from 15 nm to 100 nm in diameter have been used in a number of detection assays [Cao et al. (2010)]. We chose to conjugate DDZ to 15 nm AuNPs, since fewer copies of single-stranded DNA are required to cover the surface of a 15 nm AuNP than any AuNP of larger size [Sato et al. (2005)], and interaction of only 7.5% of DNAs conjugated to the 15 nm AuNPs with the substrate RNA is required to initiate aggregation of the AuNPs [Ogawa and Maeda (2008)].

Figure 3:
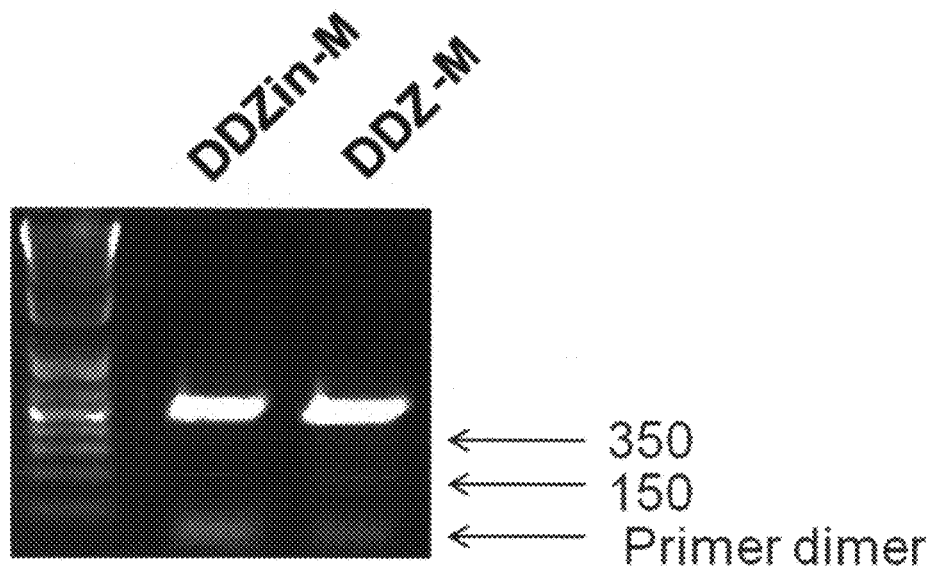
FIG. 3 sets forth an illustration showing in vitro DDZ activity assay. DDZ-M-AuNPs ($1 \times 10^5$ particles/mL) were placed in a buffered solution containing 10 mM $MgCl_2$, DENV-2 NGC RNAs (0.6 µM) isolated from *Ae. albopictus* C6/36. Following incubation at 37° C. for 30 minutes, RT-PCR was performed as described in EXAMPLE 1 to amplify digestion products. Fragments were then separated on a 1.75% TAE agarose gel in the presence of ethidium bromide and photographed under UV light. Arrows indicate digestion products of approximately 150 and 350 bases and the primer dimer, respectively. The results demonstrate digestion of full length DENV-2 genome by DDZ-M in spite of AuNP conjugation. DDZ=anti-dengue virus DNAzyme, DDZin=inactive anti-dengue virus DNAzyme.

AuNP-conjugated DDZs were analyzed for their ability to cleave the DENV-2 NGC RNA in vitro. DENV-2 NGC viral RNAs were isolated from infected *Ae. albopictus* C6/36 cells, and incubated in a buffered solution containing $1\times10^5$ DDZ-M-tethered AuNPs/mL for 30 minutes at 37° C. Digestion products were then amplified by RT-PCR using heterologous and hexamer primers designed to aid in the amplification of DDZ digestion products. Successful digestion of the DENV-2 NGC RNA genome by DDZ-M was demonstrated by the positive detection of 2 fragments of approximately 150 and 350 bases in size, indicative of DDZ-M catalysis (FIG. 3). DNAzyme catalytic activity against the DENV-2 RNA genome was validated by the inclusion of an inactive DNAzyme negative control, DDZin-M, that was created by inverting the catalytic domain which has been previously shown to render the DNAzyme catalytically inactive [Carter et al. (2013)]. As expected, the catalytically inactive DDZin-M did not digest the DENV-2 NGC genome due to this alteration in the catalytic domain.

Addition of an Artificial DENV-2 RNA Target Initiates Aggregation of DDZ Tethered AuNPs As an initial test of the utility of our colorimetric detection method, a synthetic target was designed and synthesized that corresponds to the 5' 170 bases of the DENV-2 NGC genome. This stretch of nucleotides included the highly conserved 5' CS domain and the initial 74 bases of the capsid gene [Alvarez et al. (2005)]. Synthetic target (7.5 nM) was added to a buffered mixture containing $1\times10^5$ DDZAuNPs/mL, 10 mM $MgCl_2$ and 1.0 M NaCl (FIG. 4) as previously described [Song et al. (2011)]. The control mix contained the same components except 50 mM Tris HCl was substituted for the synthetic DENV-2 target. Reaction mixes were incubated at 37° C. to initiate the detection reaction. Aggregation of the DDZ-M-tethered AuNPs, observed by a red to clear color transition, was evident within the first 5 minutes of incubation. This aggregation event occurred only in the presence of the synthetic DENV-2 RNA, and therefore demonstrated a positive test for the presence of DENV-2 RNA.

Optimization of NaCl Concentration

Sodium, in the form of NaCl, is an essential component of AuNP colorimetric detection assays because this monovalent salt drives aggregation of oligonucleotide-conjugated AuNPs following the interaction of the AuNP conjugated probes with complimentary oligonucleotide targets [Ogawa and Maeda (2008); Ogawa (2011)]. NaCl concentrations greater than 2 M have been reported to cause instability of conjugated AuNPs [Ogawa and Maeda (2008)]. Published reports also indicate that NaCl concentrations for effective AuNP aggregation can vary from 1.0 M to 1.5 M [Ogawa and Maeda (2009); Weil et al. (2004)]. In light of these observations, we evaluated the optimal NaCl concentration necessary to initiate aggregation of DDZ-M-AuNP following interaction with the DENV-2 genome.

DENV genomic RNAs (~0.6 µM), isolated from infected C6/36 cell supernatants, were added to a buffered reaction mixture containing DDZ-M-AuNP (~$1\times10^5$ particles/mL), 10 mM $MgCl_2$ and NaCl at concentrations ranging from 0 M to 2 M (FIG. 5A). Samples were incubated at 37° C. for 30 min. A red to clear color transition confirming optimal detection of the DENV genome was observed in as little as 5 minutes in the presence of 1.5 M NaCl. The 0 M NaCl control provided confirmation that the red to clear color transitions observed were not the result of destabilization of aggregates from DNAzyme activity against the AuNPs, nor were they caused by non-specific interaction of the DNAzymes with cell derived oligonucleotides. Our results also demonstrate the high stability and utility of our DDZ-AuNP assay at temperatures greater than 30° C., a critical criterion for any DENV detection assay [Peeling et al. 2010].

Determination of the Optimal SDS Concentration for Colorimetric DDZ-AuNP Detection of DENV Our DDZ-AuNP assay system demonstrated utility in detecting purified DENV-2 RNAs. However, to improve this assay for field use we needed a protocol that has speed, efficacy, and simplicity in detecting DENV RNA directly from virions. Liberating the DENV RNA genome from virion particles using a low cost, non-toxic RNA extraction reagent that is stable in the reaction buffer and does not interfere with the assay would be ideal. Sodium dodecyl sulfate (SDS) is an effective non-ionic detergent for lysing virus particles [Becker et al. (1975)]. SDS may be considered an ideal component for our colorimetric detection assays because it is non-toxic, stable in the reaction buffer, and does not require additional manipulation during lysis.

The optimal concentration of SDS was determined by adding cellular supernatants containing $1\times10^6$ DENV-2/mL to buffered reaction mixes containing DDZ-tethered AuNPs (DDZ-AuNP), 10 mM $MgCl_2$ and SDS at concentrations of 0% (w/v), 0.5% (w/v) or 1.0% (w/v) (FIG. 5B). Detection of DENV-2 NGC RNAs from cell culture fluid was not possible in the absence of SDS following incubation at 37° C. for 30 min. Similarly, controls involving mock infected cell supernatants with or without SDS showed no red to clear color change distinctive of AuNP aggregation. However, infected cell culture supernatants displayed positive detection in as little as 5 minutes, and only in the presence of SDS and DENV-2 NGC. AuNP aggregation in the presence of 0.5% SDS and absence of DENV-2 virus particles was undetectable.

Measurement of $Mg^{2+}$ Resistance of Oligonucleotide-tethered AuNPs

Since DDZ is activated by 10 mM $MgCl_2$, we needed to confirm that the positive detection of DENV-2 was due to specific recognition of the viral genome by DDZ-M-AuNP and not the result of a false positive from $Mg^{2+}$ ion destabilization of DDZ-AuNPs [Ogawa and Maeda (2008)]. The stability of DDZ-M-AuNP was tested against increasing concentrations of $MgCl_2$ (0 mM to 20 mM) at room temperature every 5 minutes for up to 30 minutes (FIG. 6), and absorbencies were measured with a NanoDrop spectrophotometer at 520 nm. As expected, concentrations equal to or less than 10 mM $MgCl_2$ did not display a detectable effect on the stability of the oligonucleotides-tethered AuNPs as evidenced by a lack of aggregation and absorbance, while those above 10 mM resulted in rapid instability of DDZ-AuNP, leading to aggregation of the nanoparticles as evidenced by the rapid decrease in absorbance.

Specificity of DDZ-AuNP for DENV

Because chikungunya virus (CHIKV) and DENV co-infections have become more prevalent in South Asia and Africa [Caron et al. (2012)], we tested our DDZ-AuNP detection method for its specificity for DENV in the presence of CHIKV (FIG. 7a). Cellular supernatants containing $1 \times 10^6$ DENV-2 or $1 \times 10^6$ CHIKV/mL, as determined by $TCID_{50}$-IFA [Carter et al. (2010)] (1 $TCID_{50}$ unit=0.7 virus plaque forming units (pfu)) were added to a buffered reaction mixture containing $1 \times 10^6$ DDZ-M or DDZin-M tethered AuNP/mL, 10 mM $MgCl_2$, 1.5 M NaCl and 0.5% (w/v) SDS. As expected when gold nanoparticles tethered with DDZ-M DNAzymes were incubated with either mock infected or CHIKV infected cell supernatants, AuNP aggregation did not occur. Furthermore, the substitution of DDZ-M-AuNP with the negative control DDZin-M-AuNPs also resulted in negative detection of DENV. However, positive detection of DENV-2 NGC was observed in as little as 5 minutes, when DDZ-M-AuNP was incubated with DENV infected C6/36 cell derived supernatants. These results demonstrated DDZ-M-AuNP could specifically detect DENV in these mixed virus samples.

An important feature of using gold nanoparticles in colorimetric detection schemes is that the aggregation of AuNPs can be detected by UV/Vis spectroscopy. Since the absorption maximum of the 15 nm AuNPs used in this detection method is 520 nm, a decrease in absorbance at 520 nm can also be used to detect and quantitate aggregation. This was tested using reaction mixtures containing cell culture supernatants from DENV infected cells (FIG. 7b). UV/Vis spectrophotometric analysis at $A_{520}$ showed a decrease in absorbance when DDZ-M-AuNP positively detected DENV-2, suggesting the ability to quantitate these aggregation events. Mock or CHIKV infected cell culture fluids, or AuNPs tethered with the catalytically inactive DDZin-M do not elicit a detectible change in absorbance. These results show that our colorimetric DDZ-AuNP method for DENV detection possesses utility in a UV/Vis spectrophotometric platform.

DENV shares similar symptoms with other closely related mosquito-borne flaviviruses, such as Yellow Fever (YFV; [Reed et al. (1900)]), Japanese Encephalitis (JEV; Kuwayama et al. (2005)), and Zika (ZV; [Macnamara (1954)]) viruses. These viruses also co-circulate with DENV and are often misdiagnosed as dengue. Therefore, a DENV detection method must demonstrate the ability to distinguish DENV, from other mosquito-borne flaviviruses. Although the 5'-3' CS domains are largely (but not fully) conserved among flaviviruses, the entire DDZ-M binding site is not conserved among all these flaviviruses as demonstrated by a sequence alignment of our DDZ-M binding site with corresponding regions in YFV, JEV, and ZV viruses. We also performed a experimental analysis of our DDZ-M-AuNP assay to verify its ability to distinguish DENV over other flaviviruses. Separate reaction mixtures were assembled as previously described (see FIG. 4), except that artificial RNA substrates comprised of the 5' 220 nucleotides of the YFV, JEV, ZV, and DENV genomes were used as targets (FIG. 7c.). This stretch of nucleotides included the highly conserved 5' CS domain and the initial 74 bases of the capsid genes of each flavivirus. Aggregation of the DDZ-M-tethered AuNPs was evident only in the presence of the artificial DENV-2 RNA substrates and not YFV, JEV, or ZV. AuNPs tethered with the catalytically inactive DDZin-M did not aggregate in the presence of any flavivirus RNA substrate tested illustrating that mere binding of an RNA substrate is not enough to elicit an aggregation response by AuNPs. These results further validated the specificity of our DENV detection method.

Lastly, to be effective in epidemiological surveillance efforts, a DENV detection method must demonstrate the ability to detect each serotype independently of the other. An alignment of all four known DENV serotypes was performed to determine the ideal target sites for the design of serotype specific DNAzymes (FIG. 7d) and appropriate targeting sequences were assembled (Table E-3). Serotype-DNAzyme-tethered AuNPs were tested for their ability to detect viral genomic RNAs of DENV serotypes 1 through 4 (FIG. 7e). AuNPs-tethered with either a serotype-specific DDZ or the multiple serotype detecting DDZ-M were placed in separate mixtures containing the DENV serotype indicated, 0.1% SDS to lyse virus particles, and 1.5 M NaCl (FIG. 7e). Mixes were incubated at 37° C. for 5 min.

TABLE E-3

Summary of active and negative control DDZ-AuNP devices

| | | Serotype detected | | | |
|---|---|---|---|---|---|
| Devices | Designed to detect | DENV-1 | DENV-2 | DENV-3 | DENV-4 |
| DDZ-M-AuNP | All Serotypes | + | + | + | + |
| DDZ-1-AuNP | DENV-1 | + | − | − | − |
| DDZ-2-AuNP | DENV-2 | − | + | − | − |
| DDZ-3-AuNP | DENV-3 | − | − | + | − |
| DDZ-4-AuNP | DENV-4 | − | − | − | + |
| Negative Control | | | | | |
| DDZin-M-AuNP | None | − | − | − | − |

The left column lists the active (DDZ-M-AuNP and DDZ-1-AuNP through DDZ-4-AuNP) and inactive negative control (DDZin-M-AuNP) devices used in this report. The second column lists the serotype each device was designed to detect. The right column summarizes the results of the DENV detection devices and the negative control DDZin-M-AuNP.

The DENV-1 serotype-specific DDZ-1-AuNP positively detected the DENV-1 serotype as signified by a distinctive red to clear/colorless color transition. As expected, DDZ-1-AuNP did not detect DENV-2, -3, or -4, illustrating the serotype-specific nature of this approach (FIG. 7e). Likewise, each of the other serotype specific DNAzyme tethered AuNPs detected only the corresponding DENV serotype (FIG. 7e and Table E-3). These results demonstrated a DENV detection method that couples DNAzyme activity with AuNP aggregation to identify DENV in a serotype-specific manner. Cell culture supernatants containing the negative control CHIKV were added in lieu of DENV to further demonstrate the specificity of the serotype specific AuNPs and overall feasibility of our DENV detection assay. As expected, neither mock infected nor CHIKV infected cell culture supernatants yielded the red to clear color transition typically observed for the positive detection of DENV, showing our conjugated AuNPs were not influenced by cell or CHIKV derived oligonucleotides.

The Limits of DDZ-AuNP Colorimetric Detection of DENV-2

The sensitivity of our DENV detection system was assessed using standardized titers of DENV-2 (FIG. 8). Titers of $10^1$, $10^2$, $10^4$ and $10^6$ viruses/ml, as determined by $TCID_{50}$-IFA (data not shown), were assayed using our colorimetric DDZ-M-AuNP detection method as described above. The negative controls consisted of the same reaction mixture as the experimental samples lacking DENV-2 (mock), or with the catalytically inactive DDZin-M substituted for DDZ-M. Following the addition of 1.5 M NaCl and incubation at 37° C. for 5 minutes samples were analyzed by visual inspection.

Positive DENV-2 detection was evident after only 5 minutes at 37° C., and demonstrated as little as $10^1$ DENV/ml could cause a color transition, although the samples containing $10^1$ and $10^2$ transitioned to a very pale purple rather than completely clear. In addition, we calculated the amount of DENV RNA corresponds to approximately 0.6 μM (for $10^6$/ml), 6 nm (for $10^4$/ml), 0.6 nM (for $10^2$/ml), or 0.06 nM (for $10^1$/ml) of DENV RNA per reaction.

Further assessment of the sensitivity of our colorimetric DENV detection assay was further assessed by UV/Vis spectrophotometry using standardized titers of DENV-2 (FIG. 8b). Titers of $10^1$, $10^2$, and $10^6$, viruses/ml, as determined by $TCID_{50}$-IFA (data not shown) and five serial dilutions originating from $10^1$ (Dil1 through Dil5) were assayed using our colorimetric DDZ-M-AuNP assay and analyzed by UV/Vis spectrophotometry at an absorbance of 520. Positive detection of DENV-2 was evident with each sample that contained DENV-2 RNA, as demonstrated by a decrease in $A_{520}$. This result is displayed as a greater $-\log_{10}(520)$ value than the negative control Mock or CHIKV infected samples. Logarithmic interpretation of the resulting spectrophotometric measurements was performed to derive detection assay sensitivity. A linear relationship ($R^2$=0.92; FIG. 8b) demonstrates this assay is both sensitive and accurate. Spectrophotometric results also demonstrate our colorimetric DENV detection assay possesses the sensitivity to detect the presence of the DENV genome, even in very dilute samples (Dil4) which is of no surprise since researchers have previously detected colorimetric change associated with AuNP aggregation, by spectrophotometry, in samples containing only femtomole amounts of substrate [Bai et al. (2010)].

Discussion

Simple and rapid diagnostic methods to screen mosquito and patient samples for the presence of viral pathogens can significantly facilitate diagnosis and treatment of virus borne diseases in field environments where sophisticated methods of virus detection are impractical. An ideal virus detection method must distinguish the target pathogen from other diseases exhibiting similar symptoms (such as malaria, leptospirosis, typhoid, typhus and chikungunya), be highly sensitive during the acute stage of infection, provide rapid results, be inexpensive, easy to use, and stable at temperatures greater than 30*C for use in a field environment [Peeling et al. (2010)]. Furthermore, DENV detection methods must show utility in epidemiological surveillance and outbreak monitoring by allowing independent detection of each serotype, and must have the ability to distinguish between primary and secondary infection [Peeling et al. (2010)].

In light of the caveats and pitfalls of the virus detection methods currently in use, the aim of this research was to explore the utility of a multiple DENV serotype targeting DNAzyme, called DDZ-M, and DENV-serotype specific DNAzymes, coupled to AuNPs for detecting DENV. DDZ was designed to target the most conserved region of the DENV genome that includes the 5'-3' CS (FIGS. 2A and 2B). DENV serotype-specific DNAzymes (designated DDZ-1 through DDZ-4) were engineered to bind regions of DENV that are conserved within each serotype. The demonstrated ability of DNAzymes to successfully target small stretches of RNA makes these catalytic oligonucleotides highly useful for targeting conserved regions of virus genomes. Our results suggest that DNAzyme targeting coupled with non-crosslinking AuNP aggregation satisfies many of the criteria required to have an ideal method for DENV detection.

While our DDZ-AuNP colorimetric detection system demonstrates the capacity to target the highly conserved DENV 5' CS region, the utility of these molecules as detection agents requires a minimal subset of anti-DENV DNAzymes (DDZs) to be occupied for aggregation of AuNPs to occur. The high tolerance of DNAzymes to mismatched binding of the target oligonucleotides [Santoro and Joyce (1998)] makes DNAzymes ideal for detection of viruses because they will be able to detect many closely related variants. Prior studies have demonstrated aptazymes can detect synthetically produced segments of virus genomes [Cho et al. (2005)]. We have demonstrated that under optimal reaction conditions the full length genome of DENV-2 can also be detected through the aggregation of DDZ-tethered AuNPs following the interaction of the DDZ component with the DENV-2 RNA genome.

Figure 4:
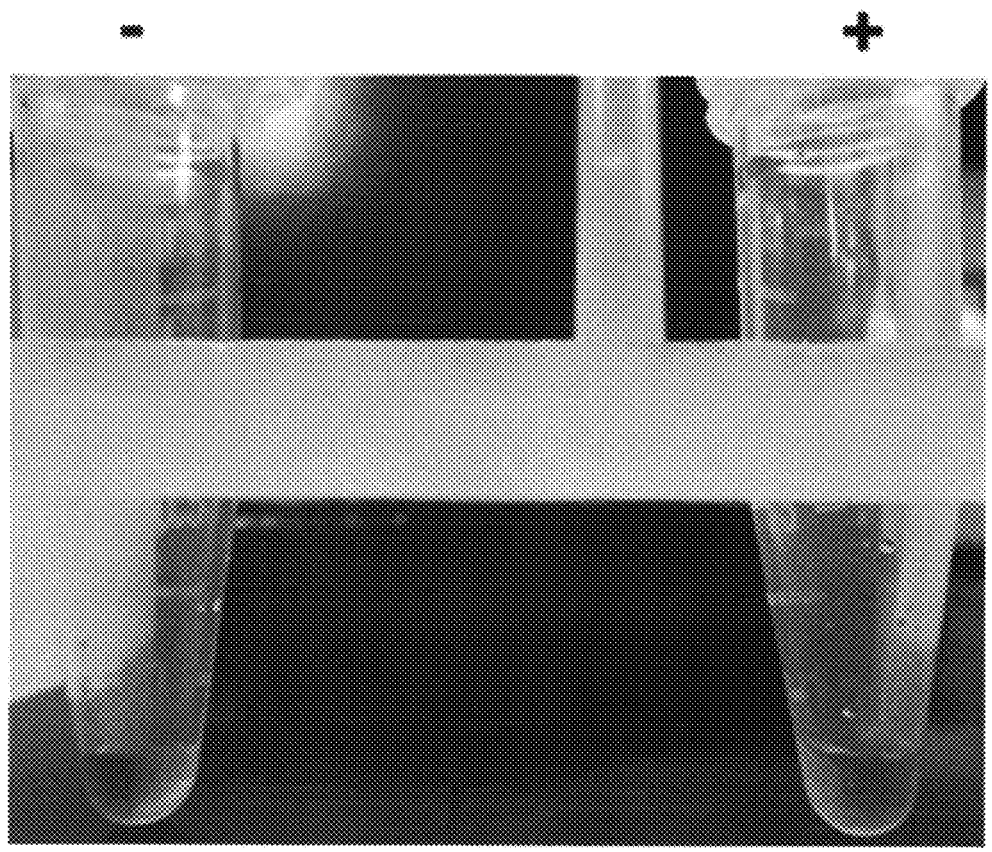
FIG. 4 sets forth an illustration showing colorimetric DDZ-AuNP detection of a synthetic DENV-2 NGC RNA target. A synthetic stretch of ribonucleotides corresponding to the 5' 170 bases of the DENV-2 RNA genome was added to a buffered mixture containing 10 mM $MgCl_2$, $1 \times 10^5$ DDZ-M-AuNP particles/mL, and 1.0 M NaCl. Samples were incubated at 37° C. for 5 minutes and photographs were taken. Control samples were treated the same as experimental except 50 mM Tris-HCl was added in lieu of the synthetic DENV-2 RNA. Aggregation of DDZ-M tethered AuNPs only occurred in the presence of synthetic DENV RNA. The results indicate that DDZ-AuNPs have the ability to detect DENV.

Our anti-DENV DNAzyme (DDZ), when conjugated with AuNPs, readily detects its cognate target sequence within a synthetic 170 base segment of the DENV-2 NGC RNA corresponding to the 5' UTR, 5' CS and the 5' 74 bases of the capsid open reading frame (FIG. 4). Aggregation events result from deshielding AuNPs from sodium ions following DDZ binding to the synthesized DENV-2 target [Williams (1995)]. The DDZ-AuNP conjugate also detects purified viral RNAs or genomic RNA liberated from cell culture derived DENV-2 NGC virions. In our analyses we utilized cell culture supernatants instead of patient blood sample or infected mosquitoes because it is more convenient to determine optimal experimentation parameters (e.g. SDS and NaCl concentrations (FIGS. 5A and 5B, respectively) and limits of detection (FIG. 8)) using a less complex cell culture system. These results provide the first confirmation of effective DENV detection using our DDZ-AuNP assay, and represent for the first time a catalytic nucleotide-based method can be used to detect DENV in fluid. Subsequent analyses will be required to optimize procedures for applications with infected patient serum or mosquito tissues.

Previous studies using oligonucleotide-tethered AuNPs have determined optimal aggregation occurs with NaCl concentrations from 1.0 M to 1.5 M, while concentrations 2.0 M destabilized conjugated AuNPs [Carter et al. 2013]. In our hands, a NaCl concentration of 1.5 M allows full aggregation of DDZ-AuNP in the presence of 0.6 µM DENV-2 RNA (FIG. 5A). We may infer that the color transition observed in samples containing DENV was not due to DNAzyme activity against the AuNP or non-specific interaction with cell derived oligonucleotides since the control solution containing 0 M NaCl did not yield a false positive result.

Figure 6:
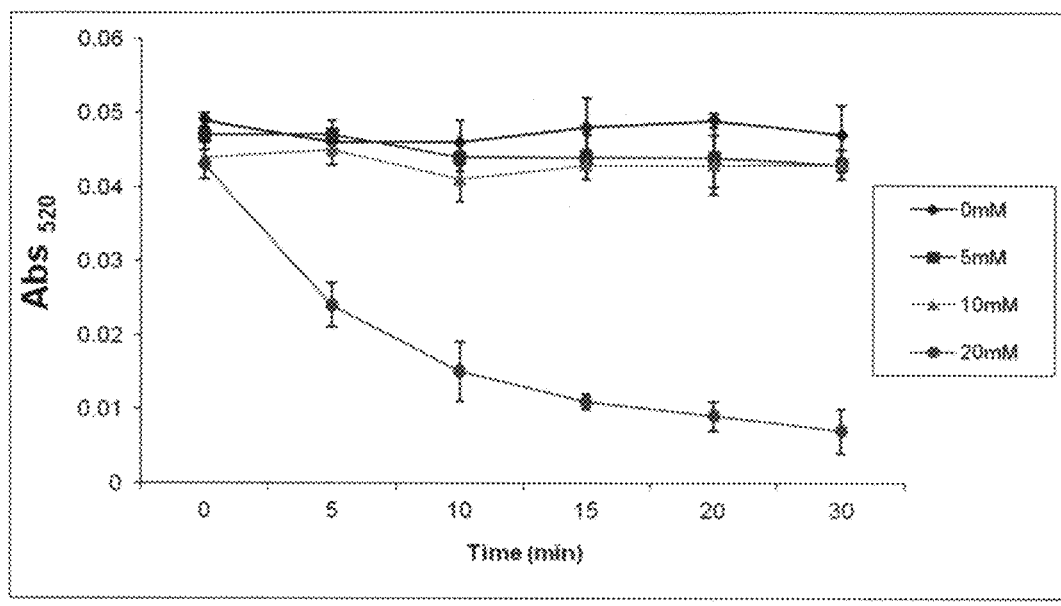
FIG. 6 sets forth an illustration showing assessment of $Mg^{2+}$ Resistance of DDZ-tethered AuNPs. DDZ-M tethered AuNPs were incubated with increasing concentrations of $MgCl_2$ (0 to 20 mM). Following a 30 minute incubation period at room temperature (~25° C.), UV/Vis spectrophotometry and photography were performed. These results demonstrate that DNAzyme conjugated AuNP aggregation is not driven by 10 mM $MgCl_2$, which is used in all detection assays described in this report.

DDZ-AuNP aggregation in our DENV detection assays was not driven by the loss of AuNP stability in the presence of 10 mM $MgCl_2$ (FIG. 6). This was not a surprising result since resistance of DNA-probe-tethered AuNPs to $MgCl_2$ concentrations ≤10 mM have been reported [Ogawa and Maeda (2009)].

Sodium dodecyl sulfate (SDS) proved to be an effective, low cost, detergent for directly lysing virus particles in our assay [Becker et al. (1975)]. SDS titration experiments on cell culture fluids containing DENV-2 NGC (FIG. 5A.) demonstrated a concentration of 0.5% (w/v) was sufficient to completely lyse DENV-2 particles without interfering with AuNP aggregation reactions. Addition of this detergent to the assay components has no effect on the cleavage or aggregation reactions.

Our DDZ-AuNP colorimetric assay is capable of distinguishing between DENV-2 NGC and CHIKV (FIG. 7), two symptomatically related viral pathogens, and indicates the utility of this detection approach in regions of the world that are endemic to both DENV and CHIKV [Caron et al. (2012)]. This increases the attractiveness and utility of the assay in epidemiological surveillance of dengue viruses in regions that are endemic to multiple pathogens that display similar symptoms. UV/Vis spectrophotometric analysis of these samples showed a fifty fold decrease in absorbance at 520 nm in the presence of DENV, demonstrating our DENV detection method has the sensitivity required for use with a spectrophotometer.

This DDZ-AuNP system allows for visual detection of DENV at titers as low as $10^1$/mL, which translates to a concentration of 0.06 nM DENV RNA (FIG. 8a). This compares quite favorably to a previously reported RNA aptazyme-AuNP system that exhibits a sensitivity of 7.5 nM [Becker et al. (1975)]. Further assessment of the limits of DENV detection by UV/Vis spectrophotometric analysis (FIG. 8b) demonstrates this assay displays sensitivity that is consistent with previous reports of RNA detection at sub-femtomole levels using gold nanoparticle detection systems [Liu et al. (2012)]. Though detection of DENV RNAs at this low concentration is not physiologically relevant to what is present in mosquitoes or humans, our ability to detect at this level demonstrates the power of AuNPs in detection schemes.

Despite the fact that we are detecting $1 \times 10^6$ $TCID_{50}$ units, there are substantially more inactive virus particles present in a given sample [Aaskov et al (2006); Li et al. (2011)]. Adding SDS to lyse DENV particles enhanced the sensitivity of our DDZ-AuNP detection method for real world applications. DENV-infected patients exhibit titers of $10^7$ to $10^{8.5}$ $TCID_{50}$ units [Vaughn (2000)]. Since we can detect approximately 6 to 7 orders of magnitude or more below this, our assay could potentially allow detection of DENV in infected patients prior to the manifestation of symptoms. Current methods for the detection of DENV lack consistent bedside detection of DENV prior to the manifestation of symptoms, a drawback of NS-1 antigen detection methods [Kabra et al. (1999); Tricou et al. (2010)]. Individual *Ae. aegypti* mosquitoes are typically infected at a titer of $10^1$ to $10^2$ $TCID_{50}$ units [Apte et al. (2012)], well within the limits of detection for this assay, making it potentially ideal for surveillance of DENV in mosquito populations.

We have demonstrated that our multi-DENV serotype detecting DDZ-M-AuNP device can detect all four DENV serotypes directly from cell culture fluid without sample processing (FIG. 7e). Serotype-specific DDZ-tethered AuNPs have demonstrated utility in detecting each of the corresponding four DENV serotypes in a serotype-specific manner (FIG. 7e). For example, DDZ-1 tethered AuNPs detected the presence of DENV-1, and only the DENV-1 serotype, due to the designed specificity of the DDZ-1 DNAzyme to a region in the DENV-1 Capsid gene that is fully conserved solely among the DENV-1 serotype. The other serotype specific DDZ-tethered AuNPs possess this same feature in the detection of their corresponding DENV serotype (FIG. 7e, see results summarized in Table E-3). Full development of this system will provide a valuable method for the detection of DENV in a serotype-specific manner in mosquito populations leading to enhanced speed and accuracy of epidemiological surveillance.

The simplicity of the DDZ-AuNP disclosed herein, provides distinct advantages over other virus detection methods. The assay can be packaged as a pre-mixed reaction solution in microcentrifuge tubes, and may be performed without any specialized equipment or training. This assay is also inexpensive, costing about $0.80 per sample, compared to serological testing or PCR-based methods which can cost $2 per sample or more to perform. Key assay components are stable for months at room temperature [Liu and Lu (2006)], and exhibit stability at temperatures greater than 30° C.

Further development of this assay will enable sensitive detection and discrimination of individual DENV serotypes in mosquito populations and patient derived samples as well as other virus derived RNAs. Detection prior to the onset of symptoms could allow more effective diagnosis and treatment of infected patients, and more rapid recovery from the disease. The simplicity of the assay makes it ideal as a means of early surveillance to target locations for more effective mosquito suppression strategies.

The DNAzyme-Nanoparticle Technology can be Applied to Facilitate the Detection of Other Viruses or Nucleic Acids DNAzymes coupled to nanoparticles, such as AuNP can be used as a highly versatile tool to facilitate the detection of oligonucleotides, and not just viral RNAs, such as DENV and CHIKV (chikungunya virus) exemplified in the Examples, noted above. In the examples, aggregation of AuNP provides a visual, colorimetric readout of the nucleic acid detected, regardless of the catalytic oligonucleotide appended. The effectiveness of our method in using DNAzyme-nanoparticle conjugates to detect other types of viral genomes (whether RNA or DNA) or other oligonucleotide molecules, whether originating from a pathogenic agent or a host cell lies in the design of the DNAzyme. Host cells, for example, can be prokaryotic or eukaryotic, particularly non-human animal, and human cells.

The successful use of DDZ-AuNPs to facilitate the detection of nucleic acids obtained from any pathogen or cell requires: (1) that the nucleic acid composition of the 5' and 3' binding arms of the DDZ must be modified to complimentary to and base pair with the 3' and 5' ends of the target sequence of interest, respectively, such that the only nucleotide on the target sequence that is not bound by the DNAzyme binding arms is the purine of the purine-pyrimidine dinucleotide motif on the target sequence; and (2) the target sequence in question must contain a purine-pyrimidine dinucleotide motif to activate the corresponding DNAzyme. These criteria apply to any RNA or DNA segment of interest one wishes to detect using methods involving DNAzymes.

The DNAzyme-Nanoparticle Technology can be Performed in Other Test Formats

Other test formats can also be used to facilitate the detection of nucleic acids with DNAzyme-nanoparticle conjugates. Use of a handheld spectrophotometer, for example, could increase speed of diagnosis, as well as the overall sensitivity and accuracy of the method. Our results show that a spectrophotometer can detect aggregation of AuNPs resulting from DDZ interaction with virus genomes at levels that would not be detected visually. The use of a handheld spectrophotometer would enable the administration of treatments prior to the onset of symptoms since the concentration of pathogen derived RNA detected would be too low to display any definitive pathology. Dipstick formats based on DNAzyme-nanoparticle conjugates, that are less sensitive, or even slower, could be used in field locations, where sample tubes or handheld equipment are not available, or are inconvenient or expensive to use.

Conclusions

The results presented here show that the DDZ-M-AuNP, designed to be active against all forms of dengue virus, is capable of effectively detecting the DENV 2-NGC genome in a sequence specific manner. Serotype specific DNAzymes tethered to AuNPs demonstrate utility in the independent identification of DENV serotypes. Coupling DNAzyme catalysis with gold nanoparticle aggregation provides an attractive alternative to other DENV detection approaches for the identification of DENV in transformed mosquito cells and tissues.

Example 2

Method of Detecting Chikungunya Virus with DNAzyme Nanoparticle Conjugates

Introduction

Chikungunya virus (CHIKV) was first detected in Tanzania in 1952, and is an emerging human pathogen responsible for significant disease outbreaks annually [Higgs and Ziegler (2010)]. *Aedes aegypti*, *Ae. albopictus*, and *Ae. vigilax* serve as the principle mosquito vectors for CHIKV, while also playing a role in dengue virus dissemination [van den Hurk (2009); Jansen et al. (2009)].

The increasing incidence of this emerging pathogen necessitate the need for a rapid and cost effective CHIKV detection method that can facilitate surveillance of mosquito populations. In Example 1, we described a simple, rapid, and cost effective gold nanoparticle coupled DNAzyme-based detection assay for dengue viruses (later published as Carter et al, 2013). In this example, we adapted this technology for the rapid, sensitive, and cost effective detection method for CHIKV, that couples the robust catalysis of a CHIKV-specific DNAzyme (CDz) with the salt-induced aggregation of gold nanoparticles (AuNPs). The limits of sensitivity for this assay in terms of molar RNA concentrations, or as infectious units of virus, are described below.

Materials and Methods

AuNPs and DNAzymes

Gold colloidal solutions containing $1.6 \times 10^{12}$ gold nanoparticles (AuNPs)/mL with a diameter of 15 nm were purchased from Cytodiagnostics (Burlington, ON, CA). Synthesized and desalted thiol-modified and unmodified DNAzymes and oligoribonucleotide CHIKV target molecules were purchased from Life Science Technologies (Grand Island, N.Y., USA). Quantification was performed with the ND-1000 spectrophotometer from NanoDrop (Wilmington, Del.).

Design of the Anti-CHIKV DNAzyme (CDZ) and Catalytically Inactive Form (CDZin)

CDZ and CDZin 5' arms were designed to bind to nucleotides 202 to 210 of the CHIKV genome:

```
                                            SEQ ID NO (25)
         (5'-AATGCTAGAGCGTTCTCGCAT-3').
```

The 3' arms were designed to complimentarily base pair to the 5' end of the target region of the CHIKV genome that corresponds to nucleotides 192 to 200. These 5' and 3' arms of CDZ facilitated cleavage of the substrate CHIKV RNA between the purine-pyrimidine dinucleotide motifs at 201 and 202.

CHIKV sequence data was obtained from the National Center of Biotechnology Information (NCBI). Sequences representative of twenty five chikungunya viruses were aligned using ClustalX [Jeanmougin et al. (1998)] (FIG. 9C). The aligned sequences comprise the following GenBank GenInfo identifiers: FN295483.3, HE806461.1, FR717336, FR717337.1, JF274082.1, L37661, EF452493.1, DQ443544.2, JN558836.1, JN558835.1, JN558834.1, JX088705.1, EU372006.1, HM045823.1, HM045822.1, HM045821.1, HM045814.1, HM045813.1, HM045812.1, HM045811.1, HM045794.1, HM045792.1, HM045791.1, HM045810.1, AF369024.2.

The CDZ target site was selected by scanning the NS1 region for one of the purine-pyrimidine dinucleotide motifs required for DNAzyme catalysis [Cairns et al. (2003); Jeanmougin et al. (1998); Larkin et al. (2007)]. The primary criterion for selection was that a purine-pyrimidine motif located within the target site must be present in all CHIKV sequences analyzed. Another important criterion for selecting suitable sites for CDZ cleavage, was that the length of conserved flanking arms be long enough to insure specificity of the DNAzyme for the target site. The optimal length for the 5' and 3' arms of CDZ was previously determined to be 9 bases for effective DNAzyme catalysis, which provides a high level of specificity, with minimal off-target effects [Cairns et al., (2003)].

nanoparticles were resuspended in 1 mL of redispersal buffer 1 [100 mM NaCl, 25 mM Tris acetate, (pH 8.2) and 0.01% SDS], centrifuged again at 16,110×g at room temperature for 15 min. The supernatant was removed and the nanoparticles

TABLE E-4

Table of Sequences and Conjugated Compounds for CHIKV targets

| Name | Description | Length | Type | SEQ ID NO: |
|---|---|---|---|---|
| CDZ and CDZin 5' arm target | 5'-AATGCTAGAGCGTTCTCGCAT-3' Corresponding to nucleotides 202 to 210 of the CHIKV genome | 21 | DNA | 25 |
| 5'Arm (5'->3') | ATGCGAGAA | 9 | DNA | 26 |
| 3'Arm (5'->3') | GCTCTAGCA | 9 | DNA | 27 |
| CDZ catalytic core | GGCTAGCTACAACGA Same as the DDZ catalytic core | 15 | DNA | 13 |
| CHIKV RNA Target | AAUGCUAGAGCGUUCUCGCAU | 21 | RNA | 28 |
| thiol-CDZ | 5'-SH-(CH$_2$)$_6$-d(TTTCTCTCGGGCTAGCTACAACGAGTTTCAGCA)-3' | 33 | | 29 |
| forward primers | TGACCGCCATTGTGTCATCGTTG binds to nucleotide positions 2631-2653 | 23 | DNA | 30 |
| reverse primers | GACCTCGTATCCACGATAGTCA binds to nucleotide position 2788-2809 | 22 | DNA | 31 |
| CHIKV Cognate target sequence | TGCTAGAGCGTTCTCGCAT corresponding to nucleotides 192 to 210 of the NS1 gene | 19 | DNA | 32 |

TABLE E-5

Nucleotide sequences of active and negative control DNAzymes and corresponding targets for CHIKV

| DNAzyme | 5'Arm (5'--->3') | 3'Arm (5'--->3') | Catalytic Core | RNA Target |
|---|---|---|---|---|
| CDZ | ATGCGAGAA (SEQ ID NO: 26) | GCTCTAGCA (SEQ ID NO: 27) | GGCTAGCTACAACGA (SEQ ID NO: 13) | AAUGCUAGAGCGUUCUCGCAU (SEQ ID NO: 28) |

CDZ-tethered AuNP Preparation (CDZ-AuNP)

Preparation of CDZ-AuNP was performed as previously described [Carter et al. 2013]. Briefly, the DTT-reduced thiol-CDZ (SH-CDZ)
(SEQ ID NO: 29)
5'-SH-(CH$^2$)$^6$-d(TTTCTCTCGGGCTAGCTACAACGAGTTTCAGCA)-3' was purified by ethanol precipitation. A volume of 3 ml of AuNP and 5 mM acetate buffer (pH 5.2) were transferred to a NaOH-washed glass scintillation vial, capped and incubated for 24 hours at room temperature. Following incubation, 5 mM Tris acetate (pH 8.2) buffer and 100 mM NaCl were added and the resulting mixture was incubated once again at room temperature for an additional 24 hours. These functionalized particles (500 µl) were transferred into 1.7-ml microcentrifuge tubes and centrifuged at 16,110×g at room temperature for 15 min to remove unreacted SH-CDZ. The were resuspended in 500 µl of redispersal buffer 2 [300 mM NaCl and 25 mM Tris acetate (pH 8.2)], and re-centrifuged for 15 min to remove the remaining unreacted SH-CDZ. The cleaned CDZ-AuNP were redispersed into 200 µL redispersal buffer 3 [100 mM NaCl, 25 mM Tris acetate, (pH 8.2) and 0.05% SDS] and stored at room temperature.

Detection of a Synthetic CHIKV RNA Target

CDZ-AuNPs (2×10$^8$/mL) were combined in a 1.5 mL microcentrifuge tube with 10 mM MgCl$_2$ for optimal DNAzyme activity [Liu et al. (2006)], 1.0M NaCl to drive aggregation of AuNPs, and synthetic CHIKV RNA target (7.5 nM) corresponding to the 5' 200 nucleotides of the CHIKV RNA genome was added [Ogawa and Maeda (2008)]. Reaction mixes were incubated at 37° C. and inspected every 5 minutes over a 30 minute period. Photographs were taken with a Nikon CoolPix S3300 camera (Nikon USA, Melville, N.Y.).

In Vitro Digestion Analysis of CDZ-tethered AuNPs

This analysis was performed as described in Example 1. Briefly, CHIKV RNA was isolated from CHIKV infected Ae. albopictus C6/36 cells using the QiaAmp viral RNA Mini Kit (Qiagen) according to the manufacturer's protocol. A volume of 10 µM of eluted CHIKV RNA was incubated with 2×10$^8$ DDZ-AuNP/ml for 30 min at 37° C. A volume of 15 ul of this reaction mixture was added to a RT-PCR mix (Super Script III, Life Science Technologies) containing heterologous and random hexametric primers to amplify the digested fragments. These RT-PCR fragments were then separated on 1.75% agarose gels.

Mg$^{2+}$ Resistance of CDZ-Tethered AuNPs

This analysis was performed as previously described [Carter et al. (2013)]. A mixture composed of 1 µl CDZ-tethered AuNPs, 50 mM Tris-HCl (pH 7.5), and increasing concentrations of MgCl$_2$ (5 mM to 20 mM) 10 µL were incubated at room temperature for 0 to ~30 min. Absorbance units were measured with a ND-1000 spectrophotometer.

Transmission Electron Microscopy (TEM)

TEM of CDZ conjugated and unconjugated AuNPs was performed using the JEOL 1220 transmission electron microscope fitted with a tungsten electron source. Samples for TEM (2 µl) were placed on TEM grids coated with a thin carbon support film, air dried, and images were taken. For AuNP applications, images were captured at 80 kV using 80,000× magnification.

Determination of Optimal Sodium Dodecyl Sulfate (SDS) Concentration

This was performed as previously described (Carter et al. 2013). Ten microliters (10 µl) of cell suspension containing 1×10$^6$ CHIKV TCID$_{50}$ units/mL was added to a mixture containing 150 mM Tris-HCl (pH 7.5), 10 mM MgCl$_2$, 2×10$^8$ CDZ-AuNP particles, 1.5M NaCl and SDS at concentrations ranging from 0% to 1% (w/v). Samples were incubated at 37° C. for 30 minutes, and analyzed every 5 min by visual inspection for aggregation of AuNPs, an indicator of positive CHIKV detection in cell culture. Photographs were taken with a Nikon CoolPix S3300 camera.

CDZ-AuNP Specificity Determination

CDZ-AuNP specificity assays were performed as previously described for DENV detection with the anti-DENV DNAzyme (DDZ) conjugated AuNPs [Carter et al. 2013]. Ten microliters (10 uL) of cell culture fluid containing 1×10$^6$/mL CHIKV vaccine strain 181/25 [Plante et al. (2011)], or DENV-2 NGC as a negative control, were added to a mixture containing 150 mM Tris-HCl (pH 7.5), 10 mM MgCl$_2$, 2×10$^8$ CDZ-AuNP or CDZin-AuNP particles, 0.5% (w/v) SDS, and 1.5M NaCl. Following incubated at 37° C. for 5 minutes, photographs were taken using the Nikon CoolPix S3300 camera, and spectrophotometric analysis was performed using the ND-1000 spectrophotometer.

Limits of CHIKV Detection with CDZ Conjugated AuNPs

CHIKV samples (FIGS. 14, 15 and 16) were produced as follows. A titer of 1×10$^8$/mL was obtained following inoculation of *Ae. albopictus* C6/36 cells with 0.1 MOI and incubated at 28° C. for 2 dpi. Serial dilutions were produced to obtain titers of 1×10$^4$/mL, 1×10$^2$/mL, and 1×10$^1$/mL. Titers were determined by TCID$_{50}$-IFA as described [Carter et al. (2011)].

The CHIKV samples described above served as substrates for CDZ-AuNP colorimetric assays to determine their limits of CHIKV detection. Ten microliters (10 µl) of each dilution stock was added to a buffered reaction mix containing 150 mM Tris-HCl (pH 7.5), 10 mM MgCl$_2$, 2×10$^8$ CDZ-AuNP particles, 1.5M NaCl, and 0.5% (w/v) SOS. Samples were mixed and incubated at 37° C. for 5 minutes, and photographs were taken with a Nikon CoolPix S3300 camera.

Real-time RT-PCR Assays

The reaction mixture (final volume of 25 ul) contained 2×SYBR green qRT-PCR Mastermix with Superscript III RT/Platinum Taq, 10 pmol of each primer, and 5 ul of extracted RNA from C6/36 cells infected with CHIKV vaccine strain 181/25, or uninfected C6/36 cells as a negative control. An additional negative control reaction was assembled that included RNA from uninfected C6/36 cells, but without CHIKV specific primers. Amplification of a fragment from the CHIKV RNA genome of 168 nt in length was performed using the following two primers:

A forward primer of the sequence

SEQ ID NO: (30)
TGACCGCCATTGTGTCATCGTTG (which binds to nucleotide position 2631-2653), and a reverse primer of the sequence

SEQ ID NO: (31)
GACCTCGTATCCACGATAGTCA (which binds to nucleotide position 2788-2809).

qRT-PCR amplification assays were performed on the 7500 Real-Time PCR System (Applied Biosystems) with the following settings: 50° C. for 15 min, 95° C. for 2 min, followed by 45 cycles of 95° C. for 15 s, 60° C. for 40 s. Data was collected at the 60° C. step.

The amount of viral RNA was calculated from a standard curve using a synthetic RNA transcript (Gene Script). The values of the quantity of CHIKV RNA/ml for each standard used was obtained using the in vitro transcript as a standard. The coefficient of determination for the standard curve that was generated had a value of (R$^2$)>0.97.

Results

Design of Anti-CHIKV 10-23 DNAzyme Conjugated Gold Nanoparticles

DNAzymes (i.e., catalytic DNAs) have demonstrated utility and impressive sensitivity in detecting metal ions or RNA [Cairns et al. (2003); Geyer and Sen (1998)]. DNAzymes possess a catalytic core that is activated by binding a cofactor (e.g., Pb$^{2+}$ or Mg$^{2+}$) Cairns et al. (2003); Geyer and Sen (1998). Some DNAzymes, however, do not require cofactors for catalysis [Geyer et al. (1997)].

The 10-23 DNAzyme [Cairns et al (2003)] is capable of cleaving substrate RNAs with high sequence specificity at sites containing purine-pyrimidine (R-Y) junctions [Santoro and Joyce (1997)]. We chose this particular DNAzyme for use in our CHIKV detection system because of its decreased dependence on secondary structure for its activity versus other DNAzymes [Carter et al. (2013)], which was predicted to increase catalysis in our in vitro assays where biomolecular folding would be very erratic. The anti-CHIKV 10-23 DNAzyme, CDZ (FIG. 2A), was designed with 5' and 3' arms that target a highly conserved sequence present in all CHIKV that were identified through ClustalX alignments. This DNAzyme construct was conjugated to 15 nm AuNPs which we previously determined were effective for the positive detection of dengue viruses [Carter et al. (2013)].

Assessment of CDZ-AuNP Targeting Using in vitro Cleavage Assays

The colorimetric detection of CHIKV by CDZ-AuNP can be divided into three phases: targeting/cleavage, activation of AuNPs, and aggregation/detection (FIG. 9B). In the presence of CHIKV RNA, the 5' and 3' arms of the AuNP-conjugated anti-CHIKV DNAzyme (CDZ) bind to the 3' and 5' ends of the targeted region, respectively. In the presence of the $Mg^{2+}$, DDZ digests the viral RNA. During the catalysis, and in the presence of NaCl and heat, these AuNPs aggregate; leading to a rapid and visually detectable red to clear/colorless color transition [Ogawa and Maeda (2008); Song et al. (2011)]. This color transition, detected visually with ease, signifies the successful detection of CHIKV. As an added benefit, this color transition is quantifiable by spectrophotometry at 520 nm [Englebienne, (1998); Song et al. (2011)].

Initial examination of the utility of our CDZ-AuNP colorimetric detection method was performed against a synthetic 19 base CHIKV substrate corresponding to nucleotides 188 to 207 of the NS1 gene. Our CDZ was designed to complimentarily base pair with this target sequence (Carter et al. 2013). In vitro assessment of the activity of CDZ-AuNP in the presence of CHIKV artificial substrate RNAs was performed as in Example 1 (Carter et al. 2013). The synthetic CHIKV substrate (7.5 nM) was combined with a buffered mixture containing 1.0 M NaCl, 10 mM $MgCl_2$, and $2\times10^8$ CDZ-AuNPs (FIG. 9A). The control mix substituted the CDZ-AuNPs with the negative control CDZin-AuNP, which was created through inversion of the catalytic domain to render the DNAzyme catalytically inactive [Auslander et al. (2010)]. Reaction mixes were incubated at 37° C. and monitored for the distinctive red to clear color transition, indicating positive detection of the CHIKV RNA substrate. Aggregation of the CDZ-tethered AuNPs, was evident within the first 5 minutes of incubation. This aggregation event occurred only in the presence of the synthetic substrate and active CDZ-AuNPs, demonstrating a positive test for the presence of CHIKV.

AuNP-conjugated CDZs were analyzed for their ability to target and cleave RNAs derived from CHIKV strain 181/25 in vitro. Viral RNAs were isolated from infected *Ae. albopictus* C6/36 cells, and incubated in a reaction mix containing $2\times10^8$ CDZ-tethered AuNPs for 30 minutes at 37° C. Digestion products were then amplified by RT-PCR, as previously described [Carter et al. 2013], using heterologous and hexamer primers designed to aid in the amplification of CDZ digestion products.

Successful digestion of the CHIKV RNA genome by CDZ was demonstrated by the detection of 2 fragments of approximately 200 and 300 bases in size by RT-PCR (FIG. 9B). Validation of DNAzyme catalytic activity against the CHIKV genome was achieved by the inclusion of the inactive DNAzyme negative control, CDZin.

Assessment of $Mg^{2+}$ Sensitivity

Figure 10:
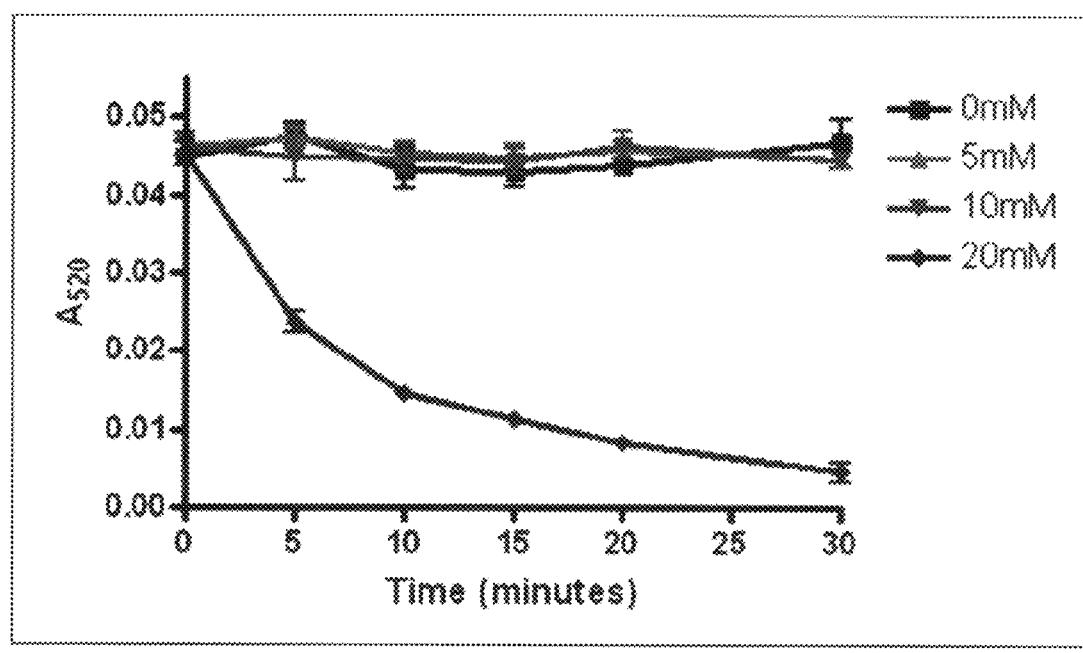
FIG. 10 sets forth an illustration assessing the $Mg^{2+}$ Resistance of CDZ-AuNP Conjugates. CDZ tethered AuNPs were incubated with increasing concentrations of $MgCl_2$ (0 to 20 mM) as described in Methods. Following a 30 minute incubation period at room temperature (~25° C.), UV/Vis spectrophotometry were performed to assess $MgCl_2$ influence on CDZ conjugated AuNPs. These results demonstrate that CDZ-AuNP aggregation is not driven by 10 mM $MgCl_2$, which is used in all detection assays described in this report.

DNAzymes are typically activated in these assays by 10 mM $MgCl_2$. We determined the necessity for $MgCl_2$ on the overall stability of our CDZ conjugated AuNPs by incubating the conjugated nanoparticles in increasing concentrations of $MgCl_2$ (0 mM to 20 mM) at room temperature, and assessed the activity every 5 minutes for up to 30 minutes (FIG. 3) by measuring absorbance at 520 nm. As expected, concentrations equal to or less than 10 mM $MgCl_2$ did not display a detectable effect on the stability CDZ-AuNPs, as previously described for DNAzyme conjugated AuNPs designed to detect dengue viruses [Carter et al. 2013]. Furthermore, magnesium ion concentrations above 10 mM resulted in rapid instability of CDZ-AuNP, leading to aggregation of the CDZ conjugated gold nanoparticles, as evidenced by a rapid decrease in absorbance (FIG. 10).

Determination of Optimal SDS Concentration in CHIKV Detection

The efficiency of our colorimetric CDZ-AuNP assay for detection of CHIKV should be increased substantially by liberating the CHIKV RNA from virions. Sodium dodecyl sulfate (SDS), an effective nonionic detergent for lysing virus particles [Becker et al. (1975)], was previously demonstrated to be an ideal component for our colorimetric detection method [Carter et al. 2013] because it does not require additional manipulations during cell lysis, is non-toxic, low cost, stable in the reaction buffer, and does not interfere with the assay.

Cellular supernatants were added to a buffered reaction mix containing CDZ-AuNPs, 10 mM $MgCl_2$ and SDS at concentrations ranging from 0% (w/v) to 1.0% (w/v) (FIG. 11). Although samples were incubated at 37° C. for 30 minutes positive detection of the CHIKV genome was observed in as little as 5 minutes, in the presence of SDS, resulting in a red to clear/colorless color transition of the sample tubes. This color transition occurred only when both CHIKV and SDS were present in the sample tubes.

Figure 12:
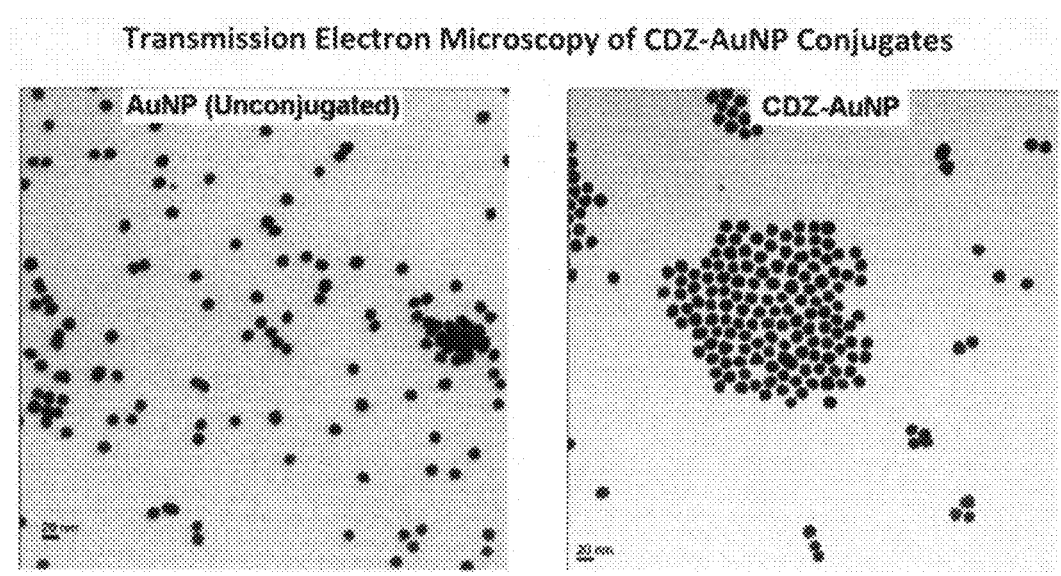
FIG. 12 sets forth an illustration showing Transmission Electron Microscopy (TEM) of CDZ-AuNP Conjugates. TEM of unconjugated and DNAzyme-linked 15 nm AuNPs were performed as described in the Materials and Methods. TEM images were taken of the following samples: Unconjugated AuNPs from the manufacturer (Cytodiagnostics) and CDZ-conjugated AuNPs in reaction buffer containing 1.5 M NaCl. TEM images were taken at 80,000× magnification. The scale bar is 20 nm.

CDZ Conjugated AuNPs Maintain their Spherical Shape in a High Salt Environment Basic morphology of AuNPs can be altered due to the conjugation procedure that is performed when DNAzymes are conjugated to AuNPs. Misshapen AuNPs can compromise the efficacy of virus detection methods that employ conjugated AuNPs. Transmission electron microscopy (TEM) is the best method to determine the structural integrity of spherical AuNPs, whether unconjugated or conjugated, by assessing their overall morphology. Consequently, we assessed the general structural integrity of unconjugated AuNPs and CDZ conjugated AuNPs in the storage buffer described in Materials and Methods, and CDZ conjugated AuNPs in the reaction buffer used in this CHIKV detection assay at 80,000× magnification (FIG. 12). Unsurprisingly, the generally round appearance of the 15 nm unconjugated AuNPs remained unchanged whether these AuNPs are CDZ conjugated or placed in our high salt (1.5 M) or high SDS (0.5%) containing reaction buffer.

Specificity Assay

Patients dually infected with CHIKV and DENV have increased in prevalence in South Asia and Africa [Caron et al. (2012] reflecting the co-incidence of these two viruses in mosquito populations. In light of this, we tested our CDZ-AuNP detection method for its specificity in detecting CHIKV in the presence of DENV (FIG. 13). Cell culture fluids containing $1\times10^6$ CHIKV/mL, $1\times10^6$ Sindbis virus, or $1\times10^6$ DENV-2 NGC/mL, as determined by $TCID_{50}$-IFA, were added to a buffered reaction mixture containing $2\times10^8$ CDZ- or CDZin-tethered AuNP, 10 mM $MgCl_2$, 1.5M NaCl and 0.5% (w/v) SDS. Incubation of samples in the presence of mock infected cell supernatants or the inactive DNAzyme, CDZin, did not result in a red to clear color change. However, this color change was evident in samples containing CHIKV, but not DENV, or Sind. These results validate the specificity of CDZ-AuNP in detecting CHIKV in these virus samples.

Limits of Detection

The sensitivity of our CHIKV detection system was assessed using standardized titers of CHIKV (FIG. 14A). Titers of $10^1$, $10^2$, $10^4$ and $10^6$ $TCID_{50}$ units/ml, as determined by $TCID_{50}$-IFA (FIG. 14B), were assayed along with a mock negative control, or were analyzed with the catalytically-inactive CDZin-AuNPs instead of CDZ-AuNPs. Following the addition of 1.5 M NaCl and incubation at 37° C. for 5 minutes samples, were analyzed by visual inspection.

Positive CHIKV detection was evident after only 5 minutes at 37° C., and demonstrated as little as $10^1$ CHIKV $TCID_{50}$ units/ml could cause a color transition, although the samples containing $10^1$ and $10^2$ transitioned to a very pale purple rather than completely clear. Though it should be noted these concentrations are based on infectious units, and not copies of RNA. Nevertheless, we are greatly encouraged since these results demonstrate we can detect CHIKV approximately 6.5 orders of magnitude below the viremia of patients who present with symptoms of CHIKV infection [Vaughn et al. (2000)].

Although positive detection of CHIKV can be determined by the color change of the sample tubes, the desired full red to clear/colorless color change was not evident for $10^1$/ml or $10^2$/ml, but rather a red to pale purple color change was achieved. Though this color change signifies positive detection of CHIKV, further assessment of the sensitivity of our colorimetric CHIKV detection assay was performed by UV/Vis spectrophotometry using standardized titers of CHIKV (FIG. 15A). Titers of $10^1$, $10^2$, and $10^6$ viruses/ml, as determined by $TCID_{50}$-IFA (FIG. 15 B), and five serial dilutions originating from RNA containing samples isolated from cells possessing $10^1$ CHIKV $TCID_{50}$ units/ml (Dil1 through Dil5) were assessed using our colorimetric CDZ-M-AuNP assay for CHIKV, and analyzed by UV/Vis spectrophotometry at an absorbance setting of 520 nm. Positive detection of CHIKV was evident for each sample that contained CHIKV RNA, demonstrated by a decrease in A520. This resulted in a greater $-\log 10(A_{520})$ value than the negative control, Mock, or DENV-infected samples. Logarithmic interpretation of the resulting spectrophotometric measurements was performed to validate assay reliability. A linear relationship ($R^2=0.93$; FIG. 15A) demonstrated this assay is sensitive and accurate.

Spectrophotometric results also demonstrated our colorimetric CHIKV detection assay is capable of detecting the presence of CHIKV RNA even in very dilute samples (Dil4). Earlier reports have also detected colorimetric change associated with AuNP aggregation in samples containing only femtomole amounts of substrate using spectrophotometry [Liu and Lu (2012)]. The ability to detect a co-circulating Flavivirus, DENV, at such low infectious unit titers may be due to the presence of immature/inactive virions, and RNA species that are not detected by $TCID_{50}$-IFA, or even RT-PCR. For example, DENV and other viruses produce aberrant RNA species called "defective RNAs" [Li et al. (2011); Marriott and Dimmock et al. (2009); van der Schaar et al. (2008)] These RNAs contain defects in the form of intragenic stop codons, nucleotide insertions, or deletions, rendering many virions produced non-infectious [Li et al. (2011)]. Some of the defective RNAs appear to be maintained during natural cycles of transmission, potentially due to complementation with fully functional DENV RNA genomes [Li et al. (2011)]. Our dengue virus and CHIKV colorimetric detection methods, DDZ-AuNP and CDZ-AuNP, take advantage of the presence of immature/inactive virions and aberrant RNA species due to the presence of detergent in the reaction mixture, the catalytic nature of DNAzymes and the effect of this RNA-induced catalysis on AuNP aggregation dynamics [Carter et al. (2013)].

To assess the limits of detection with respect to RNA copy number, supernatants were collected at 4 dpi from C6/36 cells infected with the 181/25 vaccine strain of CHIKV (MOI=0.001) and were serially diluted for qRT-PCR and $TCID_{50}$ assays to determine RNA copy number relative to infectious units (FIG. 16). Negative control qRT-PCR samples consisting of RNA from uninfected cells with and without CHIKV specific primers were included to demonstrate the RNA detected was a product of CHIKV infection [Fronhoffs et al. (2002)]. The results demonstrate an approximate average 2,000:1 ratio of CHIKV RNA to infectious units. Similar ratios were previously demonstrated for CHIKV [Nougairede et al. (2013)] and provide insight into why our RNA-based colorimetric detection method can detect this pathogen at such low uninfectious titers.

Conclusions

Simple and rapid diagnostic methods to screen mosquito and patient samples for the presence of viral pathogens can significantly facilitate prevention, diagnosis, and treatment of virus borne diseases in field environments where sophisticated methods of virus detection are impractical. Ideally virus detection methods must distinguish the target pathogen from other diseases exhibiting similar symptoms (such as malaria, leptospirosis, typhoid, typhus and chikungunya), be highly sensitive during the acute stage of infection, provide rapid results enabling early detection, be cost effective, easy to use, and stable at temperatures greater than 30° C. for use in a field environment, and must show utility in epidemiological surveillance and outbreak prediction [Peeling et al. (2011)].

Example 1 illustrated our efforts to address the need for a more sensitive method to detect dengue virus. We demonstrated the effectiveness of a rapid, portable, low-tech method of virus detection that requires no specialized training, education, or equipment by coupling the RNA targeting ability of a DENV-specific DNAzyme (DDZ) with the aggregation properties of gold nanoparticles (AuNP). The DDZ-AuNP colorimetric DENV detection method is capable of detecting all four DENV serotypes directly from *Aedes albopictus* C6/36 cell culture fluids in a matter of minutes, without RNA isolation procedures [Carter et al. (2013)], and serves as an initial proof of concept for catalytic oligonucleotide tethered AuNP driven technologies that can be applied to the detection of viruses. In this example, we demonstrate the versatility of this method, by changing the oligonucleotide sequence of the 5' and 3' binding arms of the DNAzyme conjugates such that targeting of the CHIKV-specific RNAs would occur by way of complimentary base pairing. Our results suggest that DNAzyme targeting, coupled with non-crosslinking AuNP aggregation, satisfies many of these criteria, and is an attractive method for CHIKV detection.

The 5' and 3' binding arms of the previously described anti-DENV DNAzyme were changed to an oligonucleotide sequence of the 5' and 3' binding arms that would permit complimentary base pairing, allowing targeting of the most conserved region of the CHIKV genomic RNAs encompassing nucleotides 192 to 210, of the NS1 gene [Carter et al. (2013)]. The demonstrated ability of DNAzymes to successfully target small stretches of RNA makes these catalytic oligonucleotides highly useful for targeting conserved regions of virus genomes.

While our CDZ-AuNP colorimetric detection system demonstrates the capacity to target the highly conserved region located within the CHIKV NS1 gene, the utility of these molecules as detection agents requires a minimal subset of anti-CHIKV DNAzymes (CDZs) to be occupied for aggregation of AuNPs to occur. The high tolerance of DNAzymes to mismatched binding of the target oligonucleotides [Santoro and Joyce (1998)] makes DNAzymes ideal for detection of viruses because they will be able to detect many closely related variants. Prior studies have demonstrated aptazymes can detect synthetically produced segments of virus genomes [Cho et al. (2005)]. We have demonstrated that under optimal reaction conditions the genomic CHIKV RNAs can also be detected through the aggregation of CDZ-tethered AuNPs following the interaction of the CDZ component with the CHIKV RNA genome.

Our anti-CHIKV DNAzyme (CDZ), when conjugated with AuNPs, readily detects its cognate target sequence within a synthetic 19 base segment of the CHIKV RNA corresponding to nucleotides 192 to 210 of the NS1 gene.

```
                              (SEQ ID NO: 32)
5' TGCTAGAGCGTTCTCGCAT
```

The aggregation events result from deshielding of AuNPs from sodium ions following CDZ catalysis of the synthesized CHIKV target [Williams et al. (1995)]. The CDZ-AuNP conjugate also detects purified viral RNAs or genomic RNA liberated from cell culture derived CHIKV virions. RT-PCR analysis (FIG. 9) demonstrated that our CDZ DNAzyme, while conjugated to AuNPs, retains the ability to target and cleave CHIKV RNA into 2 fragments, as expected. These results demonstrate the utility of CDZ to target and cleave CHIKV derived RNAs.

CHIKV infected cell culture supernatants were analyzed instead of patient blood samples or infected mosquitoes because it is more convenient to determine optimal experimentation parameters using a less complex cell culture system. These results provide the first confirmation of effective CHIKV detection using our CDZ-AuNP assay, by providing a catalytic nucleotide-based method can be used to detect CHIKV in fluids, and demonstrate the versatility of our colorimetric virus detection method. Though optimizing this system using a cell culture platform was successful, full development will include optimizing procedures for applications with infected patient serum or mosquito tissues.

Sodium dodecyl sulfate (SDS) has proved to be an effective, low cost, detergent for directly lysing virus particles [Becker et al. (1975)]. SDS titration experiments on cell culture fluids containing CHIKV (FIG. 11) demonstrate a concentration of 0.5% (w/v) is sufficient to completely lyse CHIKV particles without interfering with AuNP aggregation, as was previously described [Carter et al. (2013)].

The CDZ-AuNP colorimetric assay is capable of distinguishing between CHIKV and DENV-2 NGC (FIG. 13), two symptomatically related viral pathogens, and indicates the utility of this detection approach in regions of the world that are endemic to both of these viral pathogens CHIKV in regions that are endemic to multiple pathogens that display similar symptoms. The inclusion of the more closely related alphavirus, Sindbis virus (Sind), further establishes the specificity of our colorimetric CHIKV detection method.

Transmission electron microscopy of our CDZ-conjugated AuNPs (FIG. 12) demonstrated structural stability is maintained in the high salt/high SDS content of the reaction buffer used in CDZ-AuNP mediated detection of CHIKV. Structural stability of these conjugated AuNPs was established by the observance of the general spherical shape of the CDZ-conjugated AuNPs. Loss of structural stability could compromise CDZ activity, and thus CHIKV detection. The basic morphology of AuNPs can be altered due to the conjugation procedure that is performed when DNAzymes are conjugated to AuNPs. Misshapen AuNPs, for example, can compromise the efficacy of virus detection methods that employ conjugated AuNPs.

Our CDZ-AuNP system has the ability to detect CHIKV at titers as low as $10^1$/mL, and is consistent with previous reports of RNA detection at sub-femtomole levels using gold nanoparticle detection systems [Bai et al. (2010)]. Moreover though we are detecting in the range of $1\times10^1$ to $1\times10^6$ virus particles, there are substantially more inactive virus particles present in a given sample [Aaskov et al. (2006)]. Consequently adding SDS to lyse CHIKV particles enhances the effectiveness of our colorimetric CDZ-AuNP detection method for real world applications. CHIKV-infected patients exhibit a viral load of $10^9$ or more [Parida et al. (2007)]. Since we can detect 8 orders of magnitude below this, our assay could potentially allow detection of CHIKV in infected patients prior to the manifestation of symptoms. Current CHIKV detection methods lack this feature. Secondly, *Ae. albopictus* mosquito larvae are typically infected with CHIKV at a titer of $10^6$ $TCID_{50}$/larva, well within the sensitivity for this colorimetric CHIKV detection assay, making it potentially ideal for surveillance of CHIKV in mosquito populations [Reiskind et al. (2010); Westbrook et al. (2009)].

The detection of so few infectious units may be attributable to the presence of immature/inactive virions and RNA species that are not detected by $TCID_{50}$-IFA, or even RT-PCR [Rodenhuis-Zybert et al. (2010) van der Schaar et al. (2007); van der Schaar et al. (2008)]. For example, DENV and other viruses produce aberrant RNA species called "defective RNAs" in the form of intragenic stop codons, nucleotide insertions, or deletions, rendering many virions produced non-infectious [Aaskov et al. (2006); Marriott et al. (2009); Wang et al. (2002)]. Our colorimetric method for CHIKV detection, CDZ-AuNP, takes advantage of immature/inactive virions and aberrant RNA species because of the placement of detergent in the reaction mixture, the choice of target sequence, the catalysis promoted by DNAzymes and the effect of this RNA-induced catalysis on AuNP aggregation kinetics.

Prior demonstration of DNAzyme conjugated AuNPs as a sensitive DENV detection method, coupled with the demonstrated ability to detect CHIKV with a similar DNAzyme-AuNP approach further validates the versatility of this method for the potential detection of a number of viruses [Carter et al. (2013)]. The simplicity of these colorimetric assays for virus detection provides distinct advantages over other detection methods. The colorimetric assay for virus detection can be packaged as a pre-mixed reaction solution, and may be performed without any specialized equipment. Furthermore, this assay is inexpensive as compared to serological testing or PCR-based methods. Components for detection are stable for months at room temperature (data not shown), and have displayed stability at temperatures greater than 30° C., making this assay ideal for CHIKV detection in tropical climates.

Further development of these colorimetric detection assays will enable sensitive identification of virus derived RNAs in mosquito and patient samples. Bedside virus detection could allow more effective diagnosis and treatment of infected patients, and more rapid recovery from disease symptoms. Furthermore, the simplicity of colorimetric AuNP-driven detection methods make these approaches optimal in early surveillance to target locations for more effective vector control strategies.

While the preferred embodiments of the invention have been illustrated and described in detail, it will be appreciated by those skilled in the art that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

REFERENCES

All references, patents, or applications cited herein are incorporated by reference in their entirety, as if written herein.
1. Aaskov J, Buzacott K, Thu H M, Lowry K, Holmes E C: Long-term transmission of defective RNA viruses in humans and *Aedes* mosquitoes. Science 2006, 311:236-238.
2. Adalja A A, Sell T K, Bouri N, Franco C: Lessons learned during dengue outbreaks in the United States, 2001-2011. Emerg Infect Dis 2012, 18:608-614.
3. Alvarez D E, Lodeiro M F, Luduena S J, Pietrasanta L I, Gamarnik A V: Long-range RNA-RNA interactions circularize the dengue virus genome. J Virol 2005, 79:6631-6643.
4. Anez G, Heisey D A, Espina L M, Stramer S L, Rios M: Phylogenetic analysis of dengue virus types 1 and 4 circulating in Puerto Rico and Key west, Florida, during 2010 epidemics. AmJTrop Med Hyg 2012, 87:548-553.
5. Apte-Deshpande A, Paingankar M, Gokhale M D, Deobagkar D N: *Serratia odorifera* a midgut inhabitant of *Aedes aegypti* mosquito enhances its susceptibility to dengue-2 virus. PLoS One 2012, 7:e40401.
6. Auslander S, Ketzer P, Hartig J S: A ligand-dependent hammerhead ribozyme switch for controlling mammalian gene expression. Mol Biosyst 2010, 6:807-814.
7. Bai X, Shao C, Han X, Li Y, Guan Y, Deng Z: Visual detection of sub-femtomole DNA by a gold nanoparticle seeded homogeneous reduction assay: toward a generalized sensitivity-enhancing strategy. Biosens Bioelectron 2010, 25:1984-1988.
8. Baum D A, Silverman S K: Deoxyribozymes: useful DNA catalysts in vitro and in vivo. Cell Mol Life Sci 2008, 65:2156-2174.
9. Becker R, Helenius A, Simons K: Solubilization of the Semliki forest virus membrane with sodium dodecyl sulfate. Biochemistry 1975, 14:1835-1841.
10. Cairns M J, King A, Sun L Q: Optimisation of the 10-23 DNAzyme-substrate pairing interactions enhanced RNA cleavage activity at purine-cytosine target sites. Nucleic Acids Res 2003, 31:2883-2889.
11. Cao X, Ye Y, Liu S: Gold nanoparticle-based signal amplification for biosensing. Anal Biochem 2010, 417:1-16.
12. Caron M, Paupy C, Grard G, Becquart P, Mombo I, Nso B B, Kassa Kassa F, Nkoghe D, Leroy E M: Recent introduction and rapid dissemination of chikungunya virus and dengue virus serotype 2 associated with human and mosquito coinfections in Gabon, central Africa. Clin Infect Dis 2012, 55:e45-e53.
13. Carter J R, Keith J H, Barde P V, Fraser T S, Fraser M J Jr: Targeting of highly conserved dengue virus sequences with anti-dengue virus trans-splicing group I introns. BMC Mol Biol 2010, 11:84.
14. Carter, J. R., Balaraman, V., Kucharski, C. A., Fraser, T. S., and Fraser, M. J., Jr. A novel dengue virus detection method that couples DNAzyme and gold nanoparticle approaches. Virol J 10, 201.
15. Chisenhall D M, Vitek C I, Richards S L, Mores C N: A method to increase efficiency in testing pooled field-collected mosquitoes. J Am Mosq Control Assoc 2008, 24:311-314.
16. Cho S, Kim J E, Lee B R, Kim 1H, Kim B G: Bis-aptazyme sensors for hepatitis C virus replicase and helicase without blank signal. Nucleic Acids Res 2005, 33:e177.
17. Cieslak M, Szymanski J, Adamiak R W, Cierniewski C S: Structural rearrangements of the 10-23 DNAzyme to beta 3 integrin subunit mRNA induced by cations and their relations to the catalytic activity. J Biol Chem 2003, 278:47987-47996.
18. Clyde K, Kyle J L, Harris E: Recent advances in deciphering viral and host determinants of dengue virus replication and pathogenesis. J Virol 2006, 80:11418-11431.
19. Cordel, H., Quatresous, I., Paquet, C., and Couturier, E. (2006). Imported cases of chikungunya in metropolitan France, April 2005-February 2006. Euro Surveill 11, E060420 060423.
20. de Oliveira P C, Pavoni D P, Queiroz M H, de Borba L, Goldenberg S, dos Santos C N, Krieger M A: Dengue virus infections: comparison of methods for diagnosing the acute disease. J Clin Virol 2005, 32:272-277.
21. de Silva C, Walter N G: Leakage and slow allostery limit performance of single drug-sensing aptazyme molecules based on the hammerhead ribozyme. RNA 2009, 15:76-84.
22. Effler P V, Pang L, Kitsutani P, Vorndam V, Nakata M, Ayers T, Elm J, Tom T, Reiter P, Rigau-Perez J G, et al: Dengue fever, Hawaii, 2001-2002. Emerg Infect Dis 2005, 11:742-749.
23. Englebienne P: Use of colloidal gold surface plasmon resonance peak shift to infer affinity constants from the interactions between protein antigens and antibodies specific for single or multiple epitopes. Analyst 1998, 123: 1599-1603.
24. Ferapontova E E, Gothelf K V: Effect of serum on an RNA aptamer-based electrochemical sensor for theophylline. Langmuir 2009, 25:4279-4283.
25. Figueiredo L T: Dengue in Brazil. Rev Soc Bras Med Trop 2012, 45:285.
26. Fronhoffs, S., Totzke, G., Stier, S., Wernert, N., Rothe, M., Bruning, T., Koch, B., Sachinidis, A., Vetter, H., and Ko, Y. (2002). A method for the rapid construction of cRNA standard curves in quantitative real-time reverse transcription polymerase chain reaction. Molecular and cellular probes 16, 99-110.
27. Geyer C R, Sen D: Evidence for the metal-cofactor independence of an RNA phosphodiester-cleaving DNA enzyme. Chem Biol 1997, 4:579-593.
28. Geyer C R, Sen D: Lanthanide probes for a phosphodiester-cleaving, lead-dependent, DNAzyme. J Mol Biol 1998, 275:483-489.

29. Goho, A: Gold quantum dots. Science News Sep. 11, 2004, 166(11): 174.
30. Gubler D J: Dengue and dengue hemorrhagic fever. Clin Microbiol Rev 1998, 11:480-496.
31. Hall B, Hesselberth J R, Ellington A D: Computational selection of nucleic acid biosensors via a slip structure model. Biosens Bioelectron 2007, 22:1939-1947.
32. Higgs, S., and Ziegler, S. A. A nonhuman primate model of chikungunya disease. J Clin Invest (2010) 120, 657-660.
33. Jansen, C. C., Prow, N. A., Webb, C. E., Hall, R. A., Pyke, A. T., Harrower, B. J., Pritchard, I. L., Zborowski, P., Ritchie, S. A., Russell, R. C., et al. (2009). Arboviruses isolated from mosquitoes collected from urban and peri-urban areas of eastern Australia. J Am Mosq Control Assoc 25, 272-278.
34. Jeanmougin, F., Thompson, J. D., Gouy, M., Higgins, D. G., and Gibson, T. J. (1998). Multiple sequence alignment with Clustal X. Trends Biochem Sci 23, 403-405.
35. Jing L, Yi Lu: A Highly Sensitive and Selective Catalytic DNA Biosensor for Lead Ions J Am Chem Soc 2006, 122:10466-10467.
36. Kabra S K, Jain Y, Singhal T, Ratageri V H: Dengue hemorrhagic fever: clinical manifestations and management. Indian J Pediatr 1999, 66:93-101.
37. Knudsen S M, Lee J, Ellington A D, Savran C A: Ribozyme-mediated signal augmentation on a mass-sensitive biosensor. J Am Chem Soc 2006, 128:15936-15937.
38. Kuwayama M, Ito M, Takao S, Shimazu Y, Fukuda S, Miyazaki K, Kurane I, Takasaki T: Japanese encephalitis virus in meningitis patients, Japan. Emerg Infect Dis 2005, 11:471-473.
39. Lanciotti R S, Calisher C H, Gubler D J, Chang G J, Vorndam A V: Rapid detection and typing of dengue viruses from clinical samples by using reverse transcriptase-polymerase chain reaction. J Clin Microbiol 1992, 30:545-551.
40. Li D, Lott W B, Lowry K, Jones A, Thu H M, Aaskov J: Defective interfering viral particles in acute dengue infections. PLoS One 2011, 6:e19447.
41. Liu J, Lu Y: Preparation of aptamer-linked gold nanoparticle purple aggregates for colorimetric sensing of analytes. Nat Protoc 2006, 1:246-252.
42. Liu Y, Wu Z, Zhou G, He Z, Zhou X, Shen A, Hu J: Simple, rapid, homogeneous oligonucleotides colorimetric detection based on non-aggregated gold nanoparticles. Chem Commun (Camb) 2012, 48:3164-3166.
43. Macnamara F N: Zika virus: a report on three cases of human infection during an epidemic of jaundice in Nigeria. Trans R Soc Trop Med Hyg 1954, 48:139-145.
44. Marchette N J, Garcia R, Rudnick A: Isolation of Zika virus from *Aedes aegypti* mosquitoes in Malaysia. AmJTrop Med Hyg 1969, 18:411-415.
45. Marriott, A. C., and Dimmock, N. J. Defective interfering viruses and their potential as antiviral agents. Rev Med Virol 20, 51-62.
46. Nawtaisong P, Keith J, Fraser T, Balaraman V, Kolokoltsov A, Davey R A, Higgs 5, Mohammed A, Rongsriyam Y, Komalamisra N, Fraser M J Jr: Effective suppression of dengue fever virus in mosquito cell cultures using retroviral transduction of hammerhead ribozymes targeting the viral genome. Virol J 2009, 6:73.
47. Nougairede, A., De Fabritus, L., Aubry, F., Gould, E. A., Holmes, E. C., and de Lamballerie, X. (2013). Random codon re-encoding induces stable reduction of replicative fitness of Chikungunya virus in primate and mosquito cells. PLoS Pathog 9, e1003172.
48. Ogawa A, Maeda M: Easy design of logic gates based on aptazymes and noncrosslinking gold nanoparticle aggregation. Chem Commun (Camb) 2009, 21:4666-4668.
49. Ogawa A, Maeda M: Simple and rapid colorimetric detection of cofactors of aptazymes using noncrosslinking gold nanoparticle aggregation. Bioorg Med Chem Lett 2008, 18:6517-6520.
50. Ogawa A: RNA aptazyme-tethered large gold nanoparticles for on-the-spot sensing of the aptazyme ligand. Bioorg Med Chem Lett 2011, 21:155-159.
51. Parida, M. M., Santhosh, S. R., Dash, P. K., Tripathi, N. K., Lakshmi, V., Mamidi, N., Shrivastva, A., Gupta, N., Saxena, P., Babu, J. P., et al. (2007). Rapid and real-time detection of Chikungunya virus by reverse transcription loop-mediated isothermal amplification assay. J Clin Microbiol 45, 351-357.
52. Peeling R W, Artsob H, Pelegrino J L, Buchy P, Cardosa M J, Devi S, Enria D A, Farrar J, Gubler D J, Guzman M G, et al: Evaluation of diagnostic tests: dengue. Nat Rev Microbiol 2010, 8:S30-538.
53. Plante K, Wang E, Partidos C D, Weger J, Gorchakov R, Tsetsarkin K, Borland E M, Powers A M, Seymour R, Stinchcomb D T, et al: Novel chikungunya vaccine candidate with an IRES-based attenuation and host range alteration mechanism. PLoS Pathog 2011, 7:e1002142.
54. Qi R F, Zhang L, Chi C W: Biological characteristics of dengue virus and potential targets for drug design. Acta Biochim Biophys Sin (Shanghai) 2008, 40:91-101.
55. Rai M A: Epidemic: Control of dengue fever in Pakistan. Nature 2011, 479:41.
56. Ramos M M, Mohammed H, Zielinski-Gutierrez E, Hayden M H, Lopez J L, Fournier M, Trujillo A R, Burton R, Brunkard J M, Anaya-Lopez L, et al: Epidemic dengue and dengue hemorrhagic fever at the Texas-Mexico border: results of a household-based seroepidemiologic survey, December 2005. AmJTrop Med Hyg 2008, 78:364-369.
57. Randolph S E, Rogers D J: The arrival, establishment and spread of exotic diseases: patterns and predictions. Nat Rev Microbiol 2010, 8:361-371.
58. Reed W, Carroll J, Agramonte A, Lazear J W: The etiology of yellow fever-a preliminary note. Publ Health Pap Rep 1900, 26:37-53.
59. Reiskind, M. H., Westbrook, C. J., and Lounibos, L. P. Exposure to chikungunya virus and adult longevity in *Aedes aegypti* (L.) and *Aedes albopictus* (Skuse). (2010) J Vector Ecol 35, 61-68.
60. Rigau-Perez J G, Clark G G, Gubler D J, Reiter P, Sanders E J, Vorndam A V: Dengue and dengue haemorrhagic fever. Lancet 1998, 352:971-977.
61. Roberts L: Mosquitoes and disease. Science 2002, 298:82-83.
62. Rodenhuis-Zybert, I. A., van der Schaar, H. M., da Silva Voorham, J. M., van der Ende-Metselaar, H., Lei, H. Y., Wilschut, J., and Smit, J. M. Immature dengue virus: a veiled pathogen? PLoS Pathog 6, e1000718.
63. Rueda D, Walter N G: Fluorescent energy transfer readout of an aptazyme-based biosensor. Meth Mol Biol 2006, 335:289-310.
64. Santoro S W, Joyce G F: A general purpose RNA-cleaving DNA enzyme. Proc Natl Acad Sci USA 1997, 94:4262-4266.
65. Santoro S W, Joyce G F: Mechanism and utility of an RNA-cleaving DNA enzyme. Biochemistry 1998, 37:13330-13342.

66. Sato K, Hosokawa K, Maeda M: Non-cross-linking gold nanoparticle aggregation as a detection method for single-base substitutions. Nucleic Acids Res 2005, 33:e4.
67. Shu P Y, Huang J H: Current advances in dengue diagnosis. Clin Diagn Lab Immunol 2004, 11:642-650.
68. Song K M, Cho M, Jo H, Min K, Jeon S H, Kim T, Han M S, Ku J K, Ban C: Gold nanoparticle-based colorimetric detection of kanamycin using a DNA aptamer. Anal Biochem 2011, 415:175-181.
69. Sun, L Q, Cairns, M J, Gerlach, W L., Witherington, C, Wang, L, King, A: Suppression of smooth muscle cell proliferation by a c-myc RNA-cleaving deoxyribozyme. J Biol Chem 1999, 274:17236-17241.
70. Thiboutot, M. M., Kannan, S., Kawalekar, O. U., Shedlock, D. J., Khan, A. S., Sarangan, G., Srikanth, P., Weiner, D. B., and Muthumani, K. Chikungunya: a potentially emerging epidemic? PLoS Negl Trop Dis 4, e623.
71. Thompson K M, Syrett H A, Knudsen S M, Ellington A D: Group I aptazymes as genetic regulatory switches. BMC Biotechnol 2002, 2:21.
72. Tricou V, Vu H T, Quynh N V, Nguyen C V, Tran H T, Farrar J, Wills B, Simmons C P: Comparison of two dengue NS1 rapid tests for sensitivity, specificity and relationship to viraemia and antibody responses. BMC Infect Dis 2010, 10:142.
73. Tsetsarkin, K., Higgs, S., McGee, C. E., De Lamballerie, X., Charrel, R. N., and Vanlandingham, D. L. (2006). Infectious clones of Chikungunya virus (La Reunion isolate) for vector competence studies. Vector Borne Zoonotic Dis 6, 325-337.
74. Tsetsarkin, K. A., McGee, C. E., Volk, S. M., Vanlandingham, D. L., Weaver, S. C., and Higgs, S. (2009). Epistatic roles of E2 glycoprotein mutations in adaption of chikungunya virus to *Aedes albopictus* and *Ae. aegypti* mosquitoes. PLoS One 4, e6835.
75. Van Bortel, W., Dorleans, F., Rosine, J., Blateau, A., Rousset, D., Matheus, S., Leparc-Goffart, I., Flusin, O., Prat, C., Cesaire, R., et al. (2014). Chikungunya outbreak in the Caribbean region, December 2013 to March 2014, and the significance for Europe. Euro Surveill 19.
76. van den Hurk, A. F., Hall-Mendelin, S., Pyke, A. T., Smith, G. A., and Mackenzie, J. S. Vector competence of Australian mosquitoes for chikungunya virus. Vector Borne Zoonotic Dis 10, 489-495.
77. van der Schaar, H. M., Rust, M. J., Chen, C., van der Ende-Metselaar, H., Wilschut, J., Zhuang, X., and Smit, J. M. (2008). Dissecting the cell entry pathway of dengue virus by single-particle tracking in living cells. PLoS Pathog 4, e1000244.
78. van der Schaar, H. M., Rust, M. J., Waarts, B. L., van der Ende-Metselaar, H., Kuhn, R. J., Wilschut, J., Zhuang, X., and Smit, J. M. (2007). Characterization of the early events in dengue virus cell entry by biochemical assays and single-virus tracking. J Virol 81, 12019-12028.
79. Vaughn D W, Green 5, Kalayanarooj S, Innis B L, Nimmannitya S, Suntayakorn S, Endy T P, Raengsakulrach B, Rothman A L, Ennis F A, Nisalak A: Dengue viremia titer, antibody response pattern, and virus serotype correlate with disease severity. J Infect Dis 2000, 181:2-9.
80. Wang, W. K., Lin, S. R., Lee, C. M., King, C. C., and Chang, S. C. (2002). Dengue type 3 virus in plasma is a population of closely related genomes: quasispecies. J Virol 76, 4662-4665.
81. Weill L, Louis D, Sargueil B: Selection and evolution of NTP-specific aptamers. Nucleic Acids Res 2004, 32:5045-5058.
82. Westbrook, C. J., Reiskind, M. H., Pesko, K. N., Greene, K. E., and Lounibos, L. P. Larval environmental temperature and the susceptibility of *Aedes albopictus* Skuse (Diptera: Culicidae) to Chikungunya virus. Vector Borne Zoonotic Dis 10, 241-247.
83. WHO: Dengue and dengue haemorrhagic fever, Fact sheet No 117. Geneva, Switzerland: WHO: Dengue and dengue haemorrhagic fever; 2012.
84. Wieland M, Berschneider B, Erlacher M D, Hartig J S: Aptazyme-mediated regulation of 16S ribosomal RNA. Chem Biol 2010, 17:236-242.
85. Williams DHaF I: Spectroscopic Methods in Organic Chemistry. 5th edition. Blacklick, Ohio, U.S.A: McGraw-Hill; 1995.

---

What is claimed is:

1. A compound consisting of a DNAzyme (DZ) conjugated to a nanoparticle (NP) by a linker (L), designated DZ-NP, wherein said DNAzyme comprises:
a deoxyribonucleic acid (DNA) sequence comprising a 5' Binding Arm (5' BA), a Catalytic Core (CC), and a 3' Binding Arm (3' BA);
wherein said 5' and 3' Binding Arms are complementary to two target sequences on a target region of a ribonucleic acid (target RNA) comprising at least one purine-pyrimidine dinucleotide motif;
wherein said DNAzyme is an RNA-Cleaving DNAzyme selected from the group consisting of a 10-23 DNAzyme and a 8-17 DNAzyme;
wherein said nanoparticle is in a shape selected from a sphere, rod, a polygonal rod, rectangular block, cube, tetrapod, and pyramid;
wherein at least one of two target sequences on a target region of a ribonucleic acid (target RNA) comprising at least one purine-pyrimidine dinucleotide motif is a viral RNA;
wherein said viral RNA is from a virus selected from the group consisting of a mosquito-borne Flavivirus and an Alphavirus;
wherein said Linker (L) is selected from the group consisting of a covalent linker (cL) comprising two or more covalent bonds, and a high-affinity noncovalent linker (hancL) comprising two or more high-affinity noncovalent bonds; and
wherein said nanoparticle is a metallic nanoparticle comprising gold, designated as a gold nanoparticle (AuNP).

2. The compound of claim 1, wherein the DNAzyme (DZ) is linked to said nanoparticle by a linker (L) through two or more covalent bonds, designated a covalent linker (cL).

3. The compound of claim 2, wherein said covalent linker comprises —SH—(CH$_2$)$_6$—.

4. The compound of claim 2, wherein said covalent linker (cL) further comprises one or more compounds selected from the group consisting of Streptavidin fluorescent conjugates, acridine and Azobenzene fluorescent conjugates, Biotin, Biotin Diol Linker, Biotin TEG, Biotin BB, Desthiobiotin TEG, DOTA (1,4,7,10-Tetraazacyclododecane-1,4,7,10-tetraacetic acid), Dual Biotin, Photocleavable (PC) Biotin, Psoralen C2, Psoralen C6, Fluorescein, FITC, TRITC, fluorescent proteins, GFP, YFP, RFP, 2' modified NTPs, 2' fluoro dC (fC), 2' amino and 2' OMe analogs, polyethylene glycol (PEG) transport molecules, acetyl-PEG-amine, and Carboxy-PEG-Amine.

5. The compound of claim 1, wherein the DNAzyme (DZ) is linked to said nanoparticle by a linker through one or more high-affinity noncovalent bonds, designated a high affinity noncovalent linker (hancL).

6. The compound of claim 5, wherein said high affinity noncovalent linker (hancL) comprises biotin.

7. The compound of claim 1, wherein at least one of two target sequences on a target region of a ribonucleic acid (target RNA) that is a viral RNA is within
a target region comprising a viral 5'-3' Cyclization Sequence (CS).

8. The compound of claim 1, wherein said viral RNA is from a mosquito-borne Flavivirus selected from the group consisting of Avian tembusu-related virus, Calbertado virus, Chaoyang virus, Aroa virus, Dengue virus, Japanese encephalitis virus, Kokobera virus, Ntaya virus, Spondweni virus, Zika virus, and Yellow fever virus group.

9. The compound of claim 8, wherein said mosquito-borne Flavivirus is a Dengue virus.

10. The compound of claim 9, wherein the target region of a Dengue virus-specific DNAzyme (DDZ) comprising a viral 5'-3' Cyclization Sequence (CS) is selected from the group consisting of (a) a target region designated DDZ-M comprising the sequence (SEQ ID NO: 15)
         UGCUGAAACGCGAGAGAAA and (b) a target region designated DDZin-M comprising the sequence (SEQ ID NO: 20)
         UGCUGAAACGCGAGAGAAA.

11. The compound of claim 9, wherein the target region of a Dengue virus-specific DNAzyme is selected from the group consisting of DDZ-1, DDZ-2, DDZ-3, and DDZ-4, which is a conserved region, specific to each virus serotype, selected from the group consisting of:

```
DDZ-1
                                        (SEQ ID NO: 16)
UCAAGAAGAAUGGAGCGAU;

DDZ-2
                                        (SEQ ID NO: 17)
AGGCGAGAAAUACGCCUUU;

DDZ-3
                                        (SEQ ID NO: 18)
ACAGCAGGAGUCUUGGCUA;
and DDZ-4
                                        (SEQ ID NO: 19)
UCUGGAAAAAUGAACCAAC;
``` respectively.

12. The compound of claim 9, wherein said catalytic core (CC) is (SEQ ID NO: 13)
         GGCTAGCTACAACGA.

13. The compound of claim 9, wherein said 5' Arm and said 3' Arm are a pair of sequences selected from the group consisting of:

```
                                         (SEQ ID NO: 1)
            TTTCTCTCG
            and (SEQ ID NO: 7)
            GTTTCAGCA;

(SEQ ID NO: 2)
            ATCGCTCCA
            and (SEQ ID NO: 8)
            TCTTCTTGA;

(SEQ ID NO: 3)
            AAAGGCGTA
            and
```

```
                                        (SEQ ID NO: 9)
TTCTCGCCT;

(SEQ ID NO: 4)
TAGCCAAGA
and (SEQ ID NO: 10)
TCCTGCTGT;
and (SEQ ID NO: 5)
GTTGGTTCA
and (SEQ ID NO: 11)
TTTTCCAGA.
```

14. The compound of claim 9, wherein said linker and said DNAzyme designated DDZ-1, DDZ-2, DDZ-3, DDZ-4, DDZ-in-M, are selected from the group consisting of:

```
thiol-DDZ-1
                                        (SEQ ID NO: 22)
5'-SH-(CH₂)₆-d(ATCGCTCCAGGCTAGCTACAACGATCTTCTTGA)-
3' (SH-DDZ-1);

thiol-DDZ-2
                                        (SEQ ID NO: 23)
5'-SH-(CH₂)₆-d(AAAGGCGTAGGCTAGCTACAACGATTCTCGCCT)-
3' (SH-DDZ-2);

thiol-DDZ-3
                                        (SEQ ID NO: 24)
5'-SH-(CH₂)₆-d(TAGCCAAGAGGCTAGCTACAACGATCCTGCTGT)-
3' (SH-DDZ-3);

thiol DDZ-4
                                        (SEQ ID NO: 25)
5'-SH-(CH₂)₆-d(GTTGGTTCAGGCTAGCTACAACGAGTTTCAGCA)-
3' (SH-DDZ-4);
and
thiol-DDZin-M
                                        (SEQ ID NO: 26)
5'-SH-(CH₂)₆-d(TTTCTCTCGAGCAACATCGATCGGGTTTCAGCA)-
3' (SH-DDZin-M),
```
respectively.

15. The compound of claim 1, wherein said viral RNA is from an Alphavirus selected from the taxonomic group consisting of Barmah Forest virus complex, Eastern equine encephalitis complex, Middleburg virus complex, Ndumu virus complex, Semliki Forest virus complex, Venezuelan equine encephalitis complex, Western equine encephalitis complex, unclassified Alphaviruses, and recombinant Alphaviruses thereof.

16. The compound of claim 15, wherein said Alphavirus is a virus in the in the Semliki Forest Virus complex selected from the group consisting of Semliki Forest Virus and Chikungunya virus.

17. The compound of claim 16, wherein the target region of a Chikungunya virus-specific DNAzyme (CDZ) is a conserved region, specific to each virus serotype, which is

```
                                        SEQ ID NO (28)
AAUGCUAGAGCGUUCUCGCAU.
```

18. The compound of claim 16, wherein said catalytic core (CC) is

```
                                        (SEQ ID NO: 13)
GGCTAGCTACAACGA.
```

19. The compound of claim 16, wherein said 5' Arm and said 3' Arm are a pair of sequences selected from the group consisting of:

```
                                        (SEQ ID NO: 26)
ATGCGAGAA;
and (SEQ ID NO: 27)
GCTCTAGCA.
```

20. The compound of claim 16, wherein said linker and said DNAzyme designated CDZ is the compound designated:

```
thiol-CDZ(SH-CDZ)
                                        (SEQ ID NO: 29)
5'-SH-(CH2)6-d(TTTCTCTCGGGCTAGCTACAACGAGTTTCAGC
A)-3'.
```

21. The compound of claim 1, wherein at least one of two target sequences on a target region of a ribonucleic acid (target RNA) is within a viral sequence encoding a polypeptide.

22. The compound of claim 1, wherein at least one of two target sequences on a target region of a ribonucleic acid (target RNA) is within a noncoding viral sequence.

* * * * *